United States Patent
Norton et al.

(10) Patent No.: US 11,547,802 B2
(45) Date of Patent: Jan. 10, 2023

(54) ANGLED SYRINGE PATCH INJECTOR

(71) Applicant: West Pharma. Services IL, Ltd., Ra'anana (IL)

(72) Inventors: Paul H. Norton, St. Augustine, FL (US); Oz Cabiri, Hod Hasharon (IL); Ran Hezkiahu, Herzliya (IL); Richard Brough, Scottsdale, AZ (US)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 285 days.

(21) Appl. No.: 16/720,611

(22) Filed: Dec. 19, 2019

(65) Prior Publication Data

US 2020/0121854 A1 Apr. 23, 2020

Related U.S. Application Data

(63) Continuation of application No. 15/204,542, filed on Jul. 7, 2016, now Pat. No. 10,576,207.
(Continued)

(51) Int. Cl.
*A61M 5/28* (2006.01)
*A61M 5/32* (2006.01)
(Continued)

(52) U.S. Cl.
CPC ............ *A61M 5/28* (2013.01); *A61M 5/3134* (2013.01); *A61M 5/3202* (2013.01);
(Continued)

(58) Field of Classification Search
CPC .... A61M 5/28; A61M 5/3134; A61M 5/3202; A61M 5/3204; A61M 5/14248;
(Continued)

(56) References Cited

U.S. PATENT DOCUMENTS

| 232,432 A | 9/1880 | Allison |
| 1,125,887 A | 1/1915 | Schimmel |

(Continued)

FOREIGN PATENT DOCUMENTS

| CN | 1505535 A | 6/2004 |
| CN | 1747683 A | 3/2006 |

(Continued)

OTHER PUBLICATIONS

U.S. Appl. No. 13/733,516 by Cabiri, filed Jan. 3, 2013.
(Continued)

*Primary Examiner* — Tasnim Mehjabin Ahmed
(74) *Attorney, Agent, or Firm* — BakerHostetler

(57) ABSTRACT

A syringe cartridge including a reservoir part and an extension extending from the reservoir part. The extension defining a fluid path and including a molding and a first needle extending from the molding. The extension turning to a finite angle with respect to an axis of the reservoir part and at least part of the first needle is likewise at the finite angle. At least some of the part of the first needle at the finite angle being enclosed within the molding of the fluid path. A drug delivery device may be used with the cartridge and includes a skin-contacting surface. In use the longitudinal axis of the interior of the cartridge may be disposed substantially parallel to the skin-contacting surface.

12 Claims, 22 Drawing Sheets

Related U.S. Application Data

(60) Provisional application No. 62/281,536, filed on Jan. 21, 2016, provisional application No. 62/284,806, filed on Oct. 9, 2015.

(51) Int. Cl.
| | | |
|---|---|---|
| *A61M 5/31* | (2006.01) | |
| *A61M 5/34* | (2006.01) | |
| *B65D 1/36* | (2006.01) | |
| *B65D 25/10* | (2006.01) | |
| *B65D 5/50* | (2006.01) | |
| *B65D 21/02* | (2006.01) | |
| *A61M 5/142* | (2006.01) | |
| *A61M 5/158* | (2006.01) | |
| *A61M 5/145* | (2006.01) | |

(52) U.S. Cl.
CPC ............ *A61M 5/3204* (2013.01); *A61M 5/34* (2013.01); *B65D 1/36* (2013.01); *B65D 5/503* (2013.01); *B65D 21/0233* (2013.01); *B65D 25/108* (2013.01); *A61M 5/1456* (2013.01); *A61M 5/14248* (2013.01); *A61M 2005/1581* (2013.01); *A61M 2005/312* (2013.01); *A61M 2005/341* (2013.01); *A61M 2205/3306* (2013.01); *A61M 2207/00* (2013.01)

(58) Field of Classification Search
CPC ........ A61M 5/1456; A61M 2005/1581; A61M 2005/312; A61M 2005/341
See application file for complete search history.

(56) References Cited

U.S. PATENT DOCUMENTS

| | | |
|---|---|---|
| 1,321,550 A | 11/1919 | Platt |
| 1,704,921 A | 3/1929 | Nicoll |
| 1,795,530 A | 3/1931 | Cowan et al. |
| 1,795,630 A | 3/1931 | Wilson |
| 2,453,590 A | 11/1948 | Poux |
| 2,589,426 A | 3/1952 | Ogle |
| 2,677,373 A | 5/1954 | George |
| 2,702,547 A | 2/1955 | Glass |
| 2,860,635 A | 11/1958 | Wilburn |
| 3,203,269 A | 8/1965 | Perrine |
| 3,212,685 A | 10/1965 | James et al. |
| 3,585,439 A | 6/1971 | Schneeberger |
| 3,623,474 A | 11/1971 | Heilman et al. |
| 3,705,582 A | 12/1972 | Stumpf et al. |
| 3,708,945 A | 1/1973 | Klettke |
| 3,794,028 A | 2/1974 | Mueller et al. |
| 3,834,387 A | 9/1974 | Brown |
| 3,994,295 A | 11/1976 | Wulff |
| 4,085,747 A | 4/1978 | Lee |
| 4,189,065 A | 2/1980 | Herold |
| 4,195,636 A | 4/1980 | Behnke |
| 4,218,724 A | 8/1980 | Kaufman |
| 4,254,768 A | 3/1981 | Ty |
| 4,273,122 A | 6/1981 | Whitney et al. |
| 4,300,554 A | 11/1981 | Hessberg et al. |
| 4,324,262 A | 4/1982 | Hall |
| 4,403,987 A | 9/1983 | Gottinger |
| 4,425,120 A | 1/1984 | Sampson et al. |
| 4,435,173 A | 3/1984 | Siposs et al. |
| 4,465,478 A | 8/1984 | Sabelman et al. |
| 4,502,488 A | 3/1985 | Degironimo et al. |
| 4,504,263 A | 3/1985 | Steuer et al. |
| 4,549,554 A | 10/1985 | Markham |
| 4,564,054 A | 1/1986 | Gustavsson |
| 4,565,543 A | 1/1986 | Bekkering et al. |
| 4,583,974 A | 4/1986 | Kokernak |
| 4,585,439 A | 4/1986 | Michel |
| 4,599,082 A | 7/1986 | Grimard |
| 4,601,702 A | 7/1986 | Hudson |
| 4,636,201 A | 1/1987 | Ambrose et al. |
| 4,664,654 A | 5/1987 | Strauss |
| 4,685,903 A | 8/1987 | Cable et al. |
| 4,695,274 A | 9/1987 | Fox |
| 4,698,055 A | 10/1987 | Sealfon |
| 4,702,738 A | 10/1987 | Spencer |
| 4,704,105 A | 11/1987 | Adorjan et al. |
| 4,710,178 A * | 12/1987 | Henri ................ A61M 5/31581 401/181 |
| 4,729,208 A | 3/1988 | Galy et al. |
| 4,735,311 A | 4/1988 | Lowe et al. |
| 4,737,144 A | 4/1988 | Choksi |
| 4,772,272 A | 9/1988 | Mcfarland |
| 4,810,215 A | 3/1989 | Kaneko |
| 4,810,249 A | 3/1989 | Haber et al. |
| 4,813,426 A | 3/1989 | Haber et al. |
| 4,840,185 A | 6/1989 | Hernandez |
| 4,850,966 A | 7/1989 | Grau et al. |
| 4,861,341 A | 8/1989 | Woodburn |
| 4,863,434 A | 9/1989 | Bayless |
| 4,867,743 A | 9/1989 | Vaillancourt |
| 4,874,383 A | 10/1989 | Mcnaughton |
| 4,882,575 A | 11/1989 | Kawahara |
| 4,886,499 A | 12/1989 | Cirelli et al. |
| 4,892,521 A | 1/1990 | Laico et al. |
| 4,897,083 A | 1/1990 | Martell |
| 4,900,310 A | 2/1990 | Ogle, II |
| 4,915,702 A | 4/1990 | Haber |
| 4,919,569 A | 4/1990 | Wittenzellner |
| 4,919,596 A | 4/1990 | Slate et al. |
| 4,923,446 A | 5/1990 | Page et al. |
| 4,929,241 A | 5/1990 | Kulli |
| 4,950,241 A | 8/1990 | Ranford |
| 4,950,246 A | 8/1990 | Muller |
| 4,957,490 A | 9/1990 | Byrne et al. |
| 4,964,866 A | 10/1990 | Szwarc |
| 4,994,045 A | 2/1991 | Ranford |
| 4,998,924 A | 3/1991 | Ranford |
| 5,019,051 A | 5/1991 | Hake |
| 5,051,109 A | 9/1991 | Simon |
| 5,062,828 A | 11/1991 | Waltz |
| D322,671 S | 12/1991 | Szwarc |
| 5,088,988 A | 2/1992 | Talonn et al. |
| 5,109,850 A | 5/1992 | Blanco et al. |
| 5,112,317 A | 5/1992 | Michel |
| 5,114,406 A | 5/1992 | Gabriel et al. |
| 5,127,910 A | 7/1992 | Talonn et al. |
| 5,131,816 A | 7/1992 | Brown et al. |
| 5,147,326 A | 9/1992 | Talonn et al. |
| 5,156,599 A | 10/1992 | Ranford et al. |
| 5,190,521 A | 3/1993 | Hubbard et al. |
| 5,217,437 A | 6/1993 | Talonn et al. |
| 5,246,670 A | 9/1993 | Haber et al. |
| 5,254,096 A | 10/1993 | Rondelet et al. |
| 5,267,977 A | 12/1993 | Feeney, Jr. |
| 5,269,762 A | 12/1993 | Armbruster et al. |
| 5,275,582 A | 1/1994 | Wimmer |
| 5,282,593 A | 2/1994 | Fast |
| 5,295,966 A | 3/1994 | Stern et al. |
| 5,298,023 A | 3/1994 | Haber et al. |
| 5,300,045 A | 4/1994 | Plassche, Jr. |
| 5,318,522 A | 6/1994 | D'Antonio |
| 5,338,311 A | 8/1994 | Mahurkar |
| 5,342,313 A | 8/1994 | Campbell et al. |
| 5,348,544 A * | 9/1994 | Sweeney ............. A61M 5/3275 128/919 |
| 5,366,498 A | 11/1994 | Brannan et al. |
| 5,376,785 A | 12/1994 | Chin et al. |
| 5,383,865 A | 1/1995 | Michel |
| D356,150 S | 3/1995 | Duggan et al. |
| 5,415,645 A | 5/1995 | Friend et al. |
| 5,456,360 A | 10/1995 | Griffin |
| 5,478,315 A | 12/1995 | Brothers et al. |
| 5,478,316 A | 12/1995 | Bitdinger et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,624 A | 10/1996 | Righi et al. |

(56) References Cited

U.S. PATENT DOCUMENTS

| | | |
|---|---|---|
| 5,562,686 A | 10/1996 | Sauer et al. |
| 5,593,390 A | 1/1997 | Castellano et al. |
| 5,609,580 A | 3/1997 | Kwiatkowski et al. |
| 5,611,785 A | 3/1997 | Mito et al. |
| 5,616,132 A | 4/1997 | Newman |
| 5,624,400 A | 4/1997 | Firth et al. |
| 5,637,095 A | 6/1997 | Nason et al. |
| 5,643,218 A | 7/1997 | Lynn et al. |
| 5,645,530 A | 7/1997 | Boukhny et al. |
| 5,645,955 A | 7/1997 | Maglica |
| 5,647,853 A | 7/1997 | Feldmann et al. |
| 5,658,256 A | 8/1997 | Shields |
| 5,662,678 A | 9/1997 | Macklin |
| 5,672,160 A | 9/1997 | Oesterlind et al. |
| 5,690,618 A | 11/1997 | Smith et al. |
| 5,697,908 A | 12/1997 | Imbert et al. |
| 5,697,916 A | 12/1997 | Schraga |
| 5,725,500 A | 3/1998 | Micheler |
| 5,728,075 A | 3/1998 | Levander |
| D393,314 S | 4/1998 | Meisner et al. |
| 5,741,275 A | 4/1998 | Wyssmann |
| 5,766,186 A | 6/1998 | Faraz et al. |
| 5,776,103 A | 7/1998 | Kriesel et al. |
| 5,795,675 A | 8/1998 | Maglica |
| 5,800,420 A | 9/1998 | Gross et al. |
| 5,807,375 A | 9/1998 | Gross et al. |
| 5,810,167 A | 9/1998 | Fujii |
| 5,810,784 A | 9/1998 | Tamaro |
| 5,814,020 A | 9/1998 | Gross |
| 5,830,187 A | 11/1998 | Kriesel et al. |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,893,842 A | 4/1999 | Imbert |
| 5,894,015 A | 4/1999 | Rechtin |
| 5,919,167 A | 7/1999 | Mulhauser et al. |
| 5,926,596 A | 7/1999 | Edwards et al. |
| 5,931,814 A | 8/1999 | Alex et al. |
| 5,941,850 A | 8/1999 | Shah et al. |
| 5,944,699 A | 8/1999 | Barrelle et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,989,221 A | 11/1999 | Hjertman |
| 5,993,423 A | 11/1999 | Choi |
| 6,004,296 A | 12/1999 | Jansen et al. |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,045,533 A | 4/2000 | Kriesel et al. |
| 6,064,797 A | 5/2000 | Crittendon et al. |
| 6,074,369 A | 6/2000 | Sage et al. |
| 6,162,197 A | 12/2000 | Mohammad |
| 6,186,979 B1 | 2/2001 | Dysarz |
| 6,186,982 B1 | 2/2001 | Gross et al. |
| 6,189,292 B1 | 2/2001 | Odell et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,270,481 B1 | 8/2001 | Mason et al. |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D461,243 S | 8/2002 | Niedospial, Jr. |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,554,800 B1 | 4/2003 | Nezhadian et al. |
| 6,558,351 B1 | 5/2003 | Steil et al. |
| 6,565,541 B2 | 5/2003 | Sharp |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,685,678 B2 | 2/2004 | Evans et al. |
| 6,689,118 B2 | 2/2004 | Alchas et al. |
| 6,699,218 B2 | 3/2004 | Flaherty et al. |
| 6,719,141 B2 | 4/2004 | Heinz et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,783 B2 | 6/2004 | Hung et al. |
| 6,752,787 B1 | 6/2004 | Causey et al. |
| 6,767,336 B1 | 7/2004 | Kaplan |
| 6,768,425 B2 | 7/2004 | Flaherty et al. |
| 6,786,890 B2 | 9/2004 | Preuthun et al. |
| 6,800,071 B1 | 10/2004 | Mcconnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,907,679 B2 | 6/2005 | Yarborough et al. |
| 6,908,452 B2 | 6/2005 | Diaz et al. |
| 6,960,192 B1 | 11/2005 | Flaherty et al. |
| 6,979,316 B1 | 12/2005 | Rubin et al. |
| 6,997,727 B1 | 2/2006 | Legrady et al. |
| 7,001,360 B2 | 2/2006 | Veasey et al. |
| 7,004,104 B1 | 2/2006 | Kundus |
| 7,004,929 B2 | 2/2006 | Mcwethy et al. |
| 7,025,226 B2 | 4/2006 | Ramey |
| 7,033,338 B2 | 4/2006 | Vilks et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,066,909 B1 | 6/2006 | Peter et al. |
| 7,094,221 B2 | 8/2006 | Veasey et al. |
| 7,097,637 B2 | 8/2006 | Triplett et al. |
| 7,112,187 B2 | 9/2006 | Karlsson |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| RE39,923 E | 11/2007 | Blom |
| 7,291,132 B2 | 11/2007 | Deruntz et al. |
| 7,291,159 B2 | 11/2007 | Schmelzeisen-Redeker et al. |
| 7,303,549 B2 | 12/2007 | Flaherty et al. |
| 7,326,194 B2 | 2/2008 | Zinger et al. |
| 7,344,385 B2 | 3/2008 | Chen |
| 7,364,570 B2 | 4/2008 | Gerondale et al. |
| 7,377,912 B2 | 5/2008 | Graf et al. |
| 7,390,312 B2 | 6/2008 | Barrelle |
| 7,390,314 B2 | 6/2008 | Stutz et al. |
| 7,407,493 B2 | 8/2008 | Cane |

(56) References Cited

U.S. PATENT DOCUMENTS

| | | |
|---|---|---|
| 7,418,880 B1 | 9/2008 | Smith |
| D578,210 S | 10/2008 | Muta et al. |
| 7,442,186 B2 | 10/2008 | Blomquist |
| 7,455,663 B2 | 11/2008 | Bikovsky |
| 7,465,290 B2 | 12/2008 | Reilly |
| 7,468,055 B2 | 12/2008 | Prais et al. |
| 7,488,181 B2 | 2/2009 | Van |
| 7,497,842 B2 | 3/2009 | Diaz et al. |
| 7,500,963 B2 | 3/2009 | Westbye et al. |
| 7,501,587 B2 | 3/2009 | English |
| 7,503,786 B2 | 3/2009 | Kato et al. |
| 7,530,964 B2 | 5/2009 | Lavi et al. |
| 7,540,858 B2 | 6/2009 | Dibiasi |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,611,491 B2 | 11/2009 | Pickhard |
| 7,628,770 B2 | 12/2009 | Ethelfeld |
| 7,628,772 B2 | 12/2009 | Mcconnell et al. |
| 7,628,782 B2 | 12/2009 | Mair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | Mcnichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,903 B2 | 5/2010 | Estes et al. |
| 7,717,913 B2 | 5/2010 | Novak et al. |
| 7,722,574 B2 | 5/2010 | Toman et al. |
| 7,736,333 B2 | 6/2010 | Gillespie, III |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,758,548 B2 | 7/2010 | Gillespie et al. |
| 7,758,550 B2 | 7/2010 | Bollenbach et al. |
| 7,766,867 B2 | 8/2010 | Lynch et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,794,426 B2 | 9/2010 | Briones et al. |
| 7,794,427 B2 | 9/2010 | Estes et al. |
| 7,801,599 B2 | 9/2010 | Young et al. |
| 7,806,868 B2 | 10/2010 | De et al. |
| 7,828,528 B2 | 11/2010 | Estes et al. |
| 7,837,659 B2 | 11/2010 | Bush et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,901,382 B2 | 3/2011 | Daily et al. |
| 7,905,867 B2 | 3/2011 | Veasey et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,976,514 B2 | 7/2011 | Abry et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,002,754 B2 | 8/2011 | Kawamura et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,062,255 B2 | 11/2011 | Brunnberg et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,105,293 B2 | 1/2012 | Pickhard |
| 8,114,046 B2 | 2/2012 | Covino et al. |
| 8,114,064 B2 | 2/2012 | Alferness et al. |
| 8,114,066 B2 | 2/2012 | Naef et al. |
| 8,118,781 B2 | 2/2012 | Knopper et al. |
| 8,121,603 B2 | 2/2012 | Zhi |
| D657,462 S | 4/2012 | Siroky |
| 8,147,446 B2 | 4/2012 | Yodfat et al. |
| 8,151,169 B2 | 4/2012 | Bieth et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinaenen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,177,749 B2 | 5/2012 | Slate et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | Mcgrath et al. |
| 8,308,679 B2 | 11/2012 | Hanson et al. |
| 8,308,695 B2 | 11/2012 | Laiosa |
| 8,323,250 B2 | 12/2012 | Chong et al. |
| 8,348,898 B2 | 1/2013 | Cabiri |
| 8,366,668 B2 | 2/2013 | Maritan |
| 8,372,039 B2 | 2/2013 | Mernoe et al. |
| 8,373,421 B2 | 2/2013 | Lindegger et al. |
| 8,409,141 B2 | 4/2013 | Johansen et al. |
| 8,409,142 B2 | 4/2013 | Causey et al. |
| 8,409,143 B2 | 4/2013 | Lanigan et al. |
| 8,409,149 B2 | 4/2013 | Hommann et al. |
| 8,414,533 B2 | 4/2013 | Alexandersson |
| 8,414,557 B2 | 4/2013 | Istoc et al. |
| 8,425,468 B2 | 4/2013 | Weston |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente et al. |
| 8,475,408 B2 | 7/2013 | Mernoe et al. |
| 8,479,595 B2 | 7/2013 | Vazquez et al. |
| 8,490,790 B2 | 7/2013 | Cocheteux et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,512,295 B2 | 8/2013 | Evans et al. |
| 8,517,987 B2 | 8/2013 | Istoc et al. |
| 8,517,992 B2 | 8/2013 | Jones |
| 8,523,803 B1 | 9/2013 | Favreau |
| 8,551,046 B2 | 10/2013 | Causey et al. |

(56) References Cited

U.S. PATENT DOCUMENTS

| | | |
|---|---|---|
| 8,556,856 B2 | 10/2013 | Bazargan et al. |
| 8,562,364 B2 | 10/2013 | Lin et al. |
| 8,568,361 B2 | 10/2013 | Yodfat et al. |
| 8,574,216 B2 | 11/2013 | Istoc et al. |
| 8,603,026 B2 | 12/2013 | Favreau |
| 8,603,027 B2 | 12/2013 | Favreau |
| 8,603,028 B2 | 12/2013 | Mudd et al. |
| 8,622,966 B2 | 1/2014 | Causey et al. |
| 8,628,510 B2 | 1/2014 | Bazargan et al. |
| 8,647,303 B2 | 2/2014 | Cowe |
| 8,674,288 B2 | 3/2014 | Hanson et al. |
| 8,679,060 B2 | 3/2014 | Mernoe et al. |
| D702,834 S | 4/2014 | Norton et al. |
| 8,690,855 B2 | 4/2014 | Alderete et al. |
| 8,708,961 B2 | 4/2014 | Field et al. |
| 8,721,603 B2 | 5/2014 | Lundquist |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,784,378 B2 | 7/2014 | Woehr |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,858,508 B2 | 10/2014 | Lavi et al. |
| 8,876,778 B2 | 11/2014 | Carrel |
| 8,911,410 B2 | 12/2014 | Ekman et al. |
| 8,915,882 B2 | 12/2014 | Cabiri |
| 8,915,886 B2 | 12/2014 | Cowe |
| 8,920,374 B2 | 12/2014 | Bokelman et al. |
| 8,932,266 B2 | 1/2015 | Wozencroft |
| 8,979,802 B2 | 3/2015 | Woehr |
| 8,986,250 B2 | 3/2015 | Beebe et al. |
| 9,011,164 B2 | 4/2015 | Filman et al. |
| 9,011,387 B2 | 4/2015 | Ekman et al. |
| 9,061,104 B2 | 6/2015 | Daniel |
| 9,061,110 B2 | 6/2015 | Avery et al. |
| 9,072,827 B2 | 7/2015 | Cabiri |
| 9,072,845 B2 | 7/2015 | Hiles |
| 9,089,475 B2 | 7/2015 | Fangrow |
| 9,089,641 B2 | 7/2015 | Kavazov |
| 9,138,534 B2 | 9/2015 | Yodfat et al. |
| 9,149,575 B2 | 10/2015 | Cabiri |
| 9,173,997 B2 | 11/2015 | Gross et al. |
| 9,180,248 B2 | 11/2015 | Moberg et al. |
| 9,205,199 B2 | 12/2015 | Kemp et al. |
| D747,799 S | 1/2016 | Norton et al. |
| 9,233,215 B2 | 1/2016 | Hourmand et al. |
| 9,259,532 B2 | 2/2016 | Cabiri |
| 9,283,327 B2 | 3/2016 | Hourmand et al. |
| 9,308,327 B2 | 4/2016 | Marshall et al. |
| 9,314,569 B2 | 4/2016 | Causey et al. |
| 9,320,849 B2 | 4/2016 | Smith et al. |
| 9,345,834 B2 | 5/2016 | Henley et al. |
| 9,345,836 B2 | 5/2016 | Cabiri et al. |
| 9,350,634 B2 | 5/2016 | Fadell |
| 9,352,090 B2 | 5/2016 | Brereton et al. |
| 9,364,606 B2 | 6/2016 | Cindrich et al. |
| 9,381,300 B2 | 7/2016 | Smith et al. |
| 9,393,365 B2 | 7/2016 | Cabiri |
| 9,421,323 B2 | 8/2016 | Cabiri et al. |
| 9,421,337 B2 | 8/2016 | Kemp et al. |
| 9,427,531 B2 | 8/2016 | Hourmand et al. |
| 9,446,196 B2 | 9/2016 | Hourmand et al. |
| 9,452,261 B2 | 9/2016 | Alon |
| 9,463,280 B2 | 10/2016 | Cabiri |
| 9,463,889 B2 | 10/2016 | Schmitz et al. |
| 9,468,720 B2 | 10/2016 | Mudd et al. |
| 9,474,859 B2 | 10/2016 | Ekman et al. |
| 9,492,622 B2 | 11/2016 | Brereton et al. |
| 9,522,234 B2 | 12/2016 | Cabiri |
| 9,539,384 B2 | 1/2017 | Servansky |
| 9,539,388 B2 | 1/2017 | Causey et al. |
| 9,539,757 B2 | 1/2017 | Ramirez et al. |
| 9,572,926 B2 | 2/2017 | Cabiri |
| 9,572,927 B2 | 2/2017 | Bruggemann et al. |
| 9,579,471 B2 | 2/2017 | Carrel et al. |
| 9,610,407 B2 | 4/2017 | Bruggemann et al. |
| 9,656,019 B2 | 5/2017 | Cabiri et al. |
| 9,656,021 B2 | 5/2017 | Brereton et al. |
| 9,656,025 B2 | 5/2017 | Bostrom et al. |
| 9,707,356 B2 | 7/2017 | Hourmand et al. |
| 9,744,306 B2 | 8/2017 | Cowe |
| 9,775,948 B2 | 10/2017 | Bechmann et al. |
| 9,782,545 B2 | 10/2017 | Gross et al. |
| 9,789,247 B2 | 10/2017 | Kamen et al. |
| 9,814,830 B2 | 11/2017 | Mernoe et al. |
| 9,814,839 B2 | 11/2017 | Eaton |
| 9,849,242 B2 | 12/2017 | Henley et al. |
| 9,862,519 B2 | 1/2018 | Deutschle et al. |
| 9,999,722 B2 | 6/2018 | Yodfat et al. |
| 10,010,681 B2 | 7/2018 | Koch et al. |
| 10,076,356 B2 | 9/2018 | Hadvary et al. |
| 10,143,794 B2 | 12/2018 | Lanigan et al. |
| 10,149,943 B2 | 12/2018 | Bar-El et al. |
| D838,367 S | 1/2019 | Norton et al. |
| 10,166,335 B2 | 1/2019 | Reber et al. |
| 10,207,051 B2 | 2/2019 | Cereda et al. |
| 10,227,161 B2 | 3/2019 | Auerbach |
| 10,232,116 B2 | 3/2019 | Ekman et al. |
| 10,258,740 B2 | 4/2019 | Mcloughlin et al. |
| 10,376,641 B2 | 8/2019 | Hirschel et al. |
| 10,376,647 B2 | 8/2019 | Farris et al. |
| 10,434,262 B2 | 10/2019 | Bendek et al. |
| 10,576,213 B2 | 3/2020 | Gylleby |
| 10,576,220 B2 | 3/2020 | Armes |
| 10,583,260 B2 | 3/2020 | Kemp |
| 10,603,430 B2 | 3/2020 | Shor et al. |
| 10,722,645 B2 | 7/2020 | Kamen et al. |
| 10,842,942 B2 | 11/2020 | Iibuchi et al. |
| 2001/0005781 A1 | 6/2001 | Bergens et al. |
| 2001/0018937 A1 | 9/2001 | Nemoto |
| 2001/0025168 A1 | 9/2001 | Gross et al. |
| 2001/0034502 A1 | 10/2001 | Moberg et al. |
| 2001/0041869 A1 | 11/2001 | Causey et al. |
| 2002/0010423 A1 | 1/2002 | Gross et al. |
| 2002/0016569 A1 | 2/2002 | Critchlow et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0055718 A1 | 5/2002 | Hunt |
| 2002/0065488 A1 | 5/2002 | Suzuki et al. |
| 2002/0107487 A1 | 8/2002 | Preuthun |
| 2002/0120186 A1 | 8/2002 | Keimel |
| 2002/0123740 A1 | 9/2002 | Flaherty et al. |
| 2002/0151855 A1 | 10/2002 | Douglas et al. |
| 2002/0161332 A1 | 10/2002 | Ramey |
| 2002/0169215 A1 | 11/2002 | Meng |
| 2003/0009133 A1 | 1/2003 | Ramey |
| 2003/0014018 A1 | 1/2003 | Giambattista et al. |
| 2003/0050602 A1 | 3/2003 | Pettis et al. |
| 2003/0069518 A1 | 4/2003 | Daley et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0167039 A1 | 9/2003 | Moberg |
| 2003/0171717 A1 | 9/2003 | Farrugia et al. |
| 2003/0199825 A1 | 10/2003 | Flaherty et al. |
| 2003/0216683 A1 | 11/2003 | Shekalim |
| 2003/0236498 A1 | 12/2003 | Gross et al. |
| 2004/0000818 A1 | 1/2004 | Preuthun et al. |
| 2004/0010207 A1 | 1/2004 | Flaherty et al. |

(56) References Cited

U.S. PATENT DOCUMENTS

| | | |
|---|---|---|
| 2004/0049160 A1 | 3/2004 | Hsieh et al. |
| 2004/0049161 A1 | 3/2004 | Sheam |
| 2004/0082911 A1 | 4/2004 | Tiu et al. |
| 2004/0092873 A1 | 5/2004 | Moberg |
| 2004/0116866 A1 | 6/2004 | Gorman et al. |
| 2004/0122359 A1 | 6/2004 | Wenz et al. |
| 2004/0122369 A1 | 6/2004 | Schriver et al. |
| 2004/0127857 A1 | 7/2004 | Shemesh et al. |
| 2004/0135078 A1 | 7/2004 | Mandro et al. |
| 2004/0158172 A1 | 8/2004 | Hancock |
| 2004/0158205 A1 | 8/2004 | Savage |
| 2004/0186419 A1 | 9/2004 | Cho |
| 2004/0186441 A1 | 9/2004 | Graf et al. |
| 2004/0210196 A1 | 10/2004 | Bush et al. |
| 2004/0260233 A1 | 12/2004 | Garibotto et al. |
| 2005/0027255 A1 | 2/2005 | Lavi et al. |
| 2005/0033234 A1 | 2/2005 | Sadowski et al. |
| 2005/0038391 A1 | 2/2005 | Wittland et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0124940 A1 | 6/2005 | Martin et al. |
| 2005/0154353 A1 | 7/2005 | Alheidt |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | Diianni et al. |
| 2005/0245956 A1 | 11/2005 | Steinemann et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0036216 A1 | 2/2006 | Rimlinger et al. |
| 2006/0095010 A1 | 5/2006 | Westbye |
| 2006/0095014 A1 | 5/2006 | Ethelfeld |
| 2006/0122577 A1 | 6/2006 | Poulsen et al. |
| 2006/0124269 A1 | 6/2006 | Miyazaki et al. |
| 2006/0173406 A1 | 8/2006 | Hayes et al. |
| 2006/0173439 A1 | 8/2006 | Thorne et al. |
| 2006/0184154 A1 | 8/2006 | Moberg et al. |
| 2006/0195029 A1 | 8/2006 | Shults et al. |
| 2006/0206054 A1 | 9/2006 | Shekalim |
| 2006/0206057 A1 | 9/2006 | Deruntz et al. |
| 2006/0211982 A1 | 9/2006 | Prestrelski et al. |
| 2006/0229569 A1 | 10/2006 | Lavi et al. |
| 2006/0264888 A1 | 11/2006 | Moberg et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0025879 A1 | 2/2007 | Vandergaw |
| 2007/0049865 A1 | 3/2007 | Radmer et al. |
| 2007/0073228 A1 | 3/2007 | Mernoe et al. |
| 2007/0079894 A1 | 4/2007 | Kraus et al. |
| 2007/0118405 A1 | 5/2007 | Campbell et al. |
| 2007/0167912 A1 | 7/2007 | Causey et al. |
| 2007/0179444 A1 | 8/2007 | Causey et al. |
| 2007/0185449 A1 | 8/2007 | Mernoe |
| 2007/0197954 A1 | 8/2007 | Keenan |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0265568 A1 | 11/2007 | Tsals et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097326 A1 | 4/2008 | Moberg et al. |
| 2008/0097381 A1 | 4/2008 | Moberg et al. |
| 2008/0097387 A1 | 4/2008 | Spector |
| 2008/0108951 A1 | 5/2008 | Jerde et al. |
| 2008/0140006 A1 | 6/2008 | Eskuri et al. |
| 2008/0140014 A1 | 6/2008 | Miller et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215013 A1 | 9/2008 | Felix-Faure |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319383 A1 | 12/2008 | Byland et al. |
| 2008/0319416 A1 | 12/2008 | Yodfat et al. |
| 2009/0012478 A1 | 1/2009 | Weston |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076383 A1 | 3/2009 | Toews et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093763 A1 | 4/2009 | Gonnelli et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0105663 A1 | 4/2009 | Brand et al. |
| 2009/0124977 A1 | 5/2009 | Jensen |
| 2009/0143730 A1 | 6/2009 | De et al. |
| 2009/0143735 A1 | 6/2009 | De et al. |
| 2009/0149830 A1 | 6/2009 | Spector |
| 2009/0182277 A1 | 7/2009 | Carter |
| 2009/0182284 A1 | 7/2009 | Morgan |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299288 A1 | 12/2009 | Sie et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0010455 A1 | 1/2010 | Elahi et al. |
| 2010/0018334 A1 | 1/2010 | Lessing |
| 2010/0030156 A1 | 2/2010 | Beebe et al. |
| 2010/0030198 A1 | 2/2010 | Beebe et al. |
| 2010/0049128 A1 | 2/2010 | Mckenzie et al. |
| 2010/0049144 A1 | 2/2010 | Mcconnell et al. |
| 2010/0057057 A1 | 3/2010 | Hayter et al. |
| 2010/0076382 A1 | 3/2010 | Weston |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0160894 A1 | 6/2010 | Julian et al. |
| 2010/0162548 A1 | 7/2010 | Leidig |

(56) References Cited

U.S. PATENT DOCUMENTS

| | | |
|---|---|---|
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0256486 A1 | 10/2010 | Savage |
| 2010/0264931 A1 | 10/2010 | Lindegger et al. |
| 2010/0268169 A1 | 10/2010 | Llewellyn-Hyde et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0092915 A1 | 4/2011 | Olson et al. |
| 2011/0112504 A1 | 5/2011 | Causey et al. |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0224616 A1 | 9/2011 | Slate et al. |
| 2011/0224646 A1 | 9/2011 | Yodfat et al. |
| 2011/0238031 A1 | 9/2011 | Mair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022496 A1 | 1/2012 | Causey et al. |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041387 A1 | 2/2012 | Brüggemann et al. |
| 2012/0041414 A1 | 2/2012 | Estes et al. |
| 2012/0071828 A1 | 3/2012 | Tojo et al. |
| 2012/0096953 A1 | 4/2012 | Bente et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0109059 A1 | 5/2012 | Ranalletta et al. |
| 2012/0118777 A1 | 5/2012 | Kakiuchi et al. |
| 2012/0123387 A1 | 5/2012 | Gonzalez et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0172817 A1 | 7/2012 | Brüggemann et al. |
| 2012/0184917 A1 | 7/2012 | Bom et al. |
| 2012/0226234 A1 | 9/2012 | Bazargan et al. |
| 2012/0238961 A1 | 9/2012 | Julian et al. |
| 2012/0259282 A1 | 10/2012 | Alderete et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0131589 A1 | 5/2013 | Mudd et al. |
| 2013/0131604 A1 | 5/2013 | Avery |
| 2013/0133438 A1 | 5/2013 | Kow et al. |
| 2013/0172808 A1 | 7/2013 | Gilbert |
| 2013/0190693 A1 | 7/2013 | Ekman et al. |
| 2013/0200549 A1 | 8/2013 | Felts et al. |
| 2013/0204187 A1 | 8/2013 | Avery et al. |
| 2013/0204191 A1 | 8/2013 | Cindrich et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0245604 A1 | 9/2013 | Kouyoumjian et al. |
| 2013/0253419 A1 | 9/2013 | Favreau |
| 2013/0253420 A1 | 9/2013 | Favreau |
| 2013/0253421 A1 | 9/2013 | Favreau |
| 2013/0253434 A1 | 9/2013 | Cabiri |
| 2013/0267895 A1 | 10/2013 | Hemmingsen |
| 2013/0296799 A1 | 11/2013 | Degtiar et al. |
| 2013/0296824 A1 | 11/2013 | Mo et al. |
| 2013/0304021 A1 | 11/2013 | Cabiri et al. |
| 2013/0310753 A1 | 11/2013 | Cabiri |
| 2013/0323699 A1 | 12/2013 | Edwards et al. |
| 2013/0331791 A1 | 12/2013 | Gross et al. |
| 2013/0338584 A1 | 12/2013 | Mounce et al. |
| 2014/0018735 A1 | 1/2014 | Causey et al. |
| 2014/0031747 A1 | 1/2014 | Ardehali |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0121633 A1 | 5/2014 | Causey et al. |
| 2014/0128807 A1 | 5/2014 | Moberg et al. |
| 2014/0128835 A1 | 5/2014 | Moberg et al. |
| 2014/0135692 A1 | 5/2014 | Alderete et al. |
| 2014/0135694 A1 | 5/2014 | Moberg et al. |
| 2014/0142499 A1 | 5/2014 | Moberg et al. |
| 2014/0148784 A1* | 5/2014 | Anderson ............ A61M 5/3202 604/506 |
| 2014/0148785 A1 | 5/2014 | Moberg et al. |
| 2014/0163522 A1 | 6/2014 | Alderete et al. |
| 2014/0163526 A1 | 6/2014 | Cabiri et al. |
| 2014/0171881 A1 | 6/2014 | Cabiri |
| 2014/0174223 A1 | 6/2014 | Gross et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0207104 A1 | 7/2014 | Vouillamoz et al. |
| 2014/0213975 A1 | 7/2014 | Clemente et al. |
| 2014/0214001 A1 | 7/2014 | Mortazavi |
| 2014/0228768 A1 | 8/2014 | Eggert et al. |
| 2014/0236087 A1 | 8/2014 | Alderete et al. |
| 2014/0243786 A1 | 8/2014 | Gilbert et al. |
| 2014/0261758 A1 | 9/2014 | Wlodarczyk et al. |
| 2014/0343503 A1 | 11/2014 | Holmqvist |
| 2015/0005703 A1 | 1/2015 | Hutchinson et al. |
| 2015/0073344 A1 | 3/2015 | Van et al. |
| 2015/0088071 A1 | 3/2015 | Cabiri |
| 2015/0112278 A1 | 4/2015 | Ray et al. |
| 2015/0119798 A1 | 4/2015 | Gross et al. |
| 2015/0157806 A1 | 6/2015 | Knutsson |
| 2015/0202375 A1 | 7/2015 | Schabbach et al. |
| 2015/0374926 A1 | 12/2015 | Gross et al. |
| 2016/0030665 A1 | 2/2016 | Cabiri |
| 2016/0051756 A1 | 2/2016 | Cabiri |
| 2016/0144117 A1 | 5/2016 | Chun |
| 2016/0151586 A1 | 6/2016 | Kemp |
| 2016/0175515 A1 | 6/2016 | Mccullough |
| 2016/0184512 A1 | 6/2016 | Marbet et al. |
| 2016/0193406 A1 | 7/2016 | Cabiri |
| 2016/0199590 A1 | 7/2016 | Schabbach et al. |
| 2016/0213840 A1 | 7/2016 | Schabbach et al. |
| 2016/0228652 A1 | 8/2016 | Cabiri et al. |
| 2016/0296713 A1 | 10/2016 | Schader et al. |
| 2016/0296716 A1 | 10/2016 | Cabiri et al. |
| 2016/0331900 A1 | 11/2016 | Wei |
| 2016/0346478 A1 | 12/2016 | Bar-El et al. |
| 2016/0354553 A1 | 12/2016 | Anderson et al. |
| 2017/0007774 A1 | 1/2017 | Brockmeier |

(56) References Cited

U.S. PATENT DOCUMENTS

| | | |
|---|---|---|
| 2017/0043092 A1 | 2/2017 | Murakami et al. |
| 2017/0058349 A1 | 3/2017 | Levy et al. |
| 2017/0175859 A1 | 6/2017 | Brockmeier |
| 2017/0246399 A1 | 8/2017 | Forlani et al. |
| 2017/0246403 A1 | 8/2017 | Cowe et al. |
| 2018/0028765 A1 | 2/2018 | Waller et al. |
| 2018/0214637 A1 | 8/2018 | Kemp et al. |
| 2019/0022306 A1 | 1/2019 | Gibson et al. |
| 2019/0060578 A1 | 2/2019 | Farris et al. |
| 2019/0071217 A1 | 3/2019 | Brown et al. |
| 2019/0175821 A1 | 6/2019 | Kamen et al. |
| 2019/0224415 A1 | 7/2019 | Dugand et al. |
| 2019/0240417 A1 | 8/2019 | Hostettler et al. |
| 2019/0328968 A1 | 10/2019 | Giambattista |
| 2020/0009323 A1 | 1/2020 | Nair et al. |
| 2020/0215270 A1 | 7/2020 | Ogawa et al. |
| 2020/0297929 A1 | 9/2020 | Zhang |
| 2021/0138157 A1 | 5/2021 | Bar-El et al. |
| 2021/0220551 A1 | 7/2021 | Dowd et al. |

FOREIGN PATENT DOCUMENTS

| | | |
|---|---|---|
| CN | 1863566 A | 11/2006 |
| CN | 101090749 A | 12/2007 |
| CN | 101227943 A | 7/2008 |
| CN | 101448536 A | 6/2009 |
| CN | 101522235 A | 9/2009 |
| CN | 101541362 A | 9/2009 |
| CN | 101641126 A | 2/2010 |
| CN | 201692438 U | 1/2011 |
| CN | 201941304 U | 8/2011 |
| CN | 102186733 A | 9/2011 |
| CN | 102378638 A | 3/2012 |
| CN | 105102025 A | 11/2015 |
| DE | 855313 C | 11/1952 |
| DE | 1064693 B | 9/1959 |
| DE | 19518807 A1 | 12/1995 |
| DE | 19717107 A1 | 11/1998 |
| EP | 0017412 A1 | 10/1980 |
| EP | 0222656 A1 | 5/1987 |
| EP | 0401179 A1 | 12/1990 |
| EP | 0925082 A1 | 6/1999 |
| EP | 1003581 A1 | 5/2000 |
| EP | 1124600 A1 | 8/2001 |
| EP | 1219312 A2 | 7/2002 |
| EP | 1472477 A1 | 11/2004 |
| EP | 1530979 A1 | 5/2005 |
| EP | 1666080 A1 | 6/2006 |
| EP | 1372762 B1 | 2/2007 |
| EP | 1974759 A1 | 10/2008 |
| EP | 2060606 A1 | 5/2009 |
| EP | 2140897 A1 | 1/2010 |
| EP | 2173413 A1 | 4/2010 |
| EP | 2185227 A2 | 5/2010 |
| EP | 2192935 A1 | 6/2010 |
| EP | 2361648 A1 | 8/2011 |
| EP | 2364739 A1 | 9/2011 |
| EP | 2393534 A1 | 12/2011 |
| EP | 2452708 A1 | 5/2012 |
| EP | 2498589 A1 | 9/2012 |
| EP | 2574355 A1 | 4/2013 |
| EP | 2393535 B1 | 3/2015 |
| EP | 2878321 A1 | 6/2015 |
| EP | 2886144 A1 | 6/2015 |
| EP | 1904130 B1 | 3/2016 |
| EP | 2991705 A1 | 3/2016 |
| EP | 3266478 A1 | 1/2018 |
| EP | 2819724 B1 | 3/2019 |
| FR | 2770136 A1 | 4/1999 |
| GB | 2436526 A | 10/2007 |
| JP | 62-112566 A | 5/1987 |
| JP | 01-172843 U | 12/1989 |
| JP | 05-062828 A | 3/1993 |
| JP | 07-194701 A | 8/1995 |
| JP | 3035448 U | 3/1997 |
| JP | 09-505758 A | 6/1997 |
| JP | 11-507260 A | 6/1999 |
| JP | 2000-107289 A | 4/2000 |
| JP | 2000-515394 A | 11/2000 |
| JP | 2001-512992 A | 8/2001 |
| JP | 2002505601 A | 2/2002 |
| JP | 2002-507459 A | 3/2002 |
| JP | 2002-528676 A | 9/2002 |
| JP | 2003-501157 A | 1/2003 |
| JP | 2003-534061 A | 11/2003 |
| JP | 2004-501721 A | 1/2004 |
| JP | 2004-512100 A | 4/2004 |
| JP | 2003-527138 A | 8/2005 |
| JP | 2005-523127 A | 8/2005 |
| JP | 2005-527249 A | 9/2005 |
| JP | 2005-270629 A | 10/2005 |
| JP | 2006-507067 A | 3/2006 |
| JP | 2006-510450 A | 3/2006 |
| JP | 2006525046 A | 11/2006 |
| JP | 2007-509661 A | 4/2007 |
| JP | 2007-306990 A | 11/2007 |
| JP | 2008-534131 A | 8/2008 |
| JP | 2008-220961 A | 9/2008 |
| JP | 2009-502273 A | 1/2009 |
| JP | 2009-101093 A | 5/2009 |
| JP | 2010-501281 A | 1/2010 |
| JP | 2010-540054 A | 12/2010 |
| JP | 2010-540156 A | 12/2010 |
| JP | 2011136153 A | 7/2011 |
| JP | 2012-100927 A | 5/2012 |
| JP | 4947871 B2 | 6/2012 |
| JP | 2013-500811 A | 1/2013 |
| JP | 2013-505433 A | 2/2013 |
| JP | 2013-517095 A | 5/2013 |
| JP | 2013-519473 A | 5/2013 |
| JP | 2013-530778 A | 8/2013 |
| JP | 2013-531520 A | 8/2013 |
| JP | 2013-531540 A | 8/2013 |
| JP | 2014-030489 A | 2/2014 |
| JP | 2014-515669 A | 7/2014 |
| JP | 2014-518743 A | 8/2014 |
| JP | 2014-521443 A | 8/2014 |
| JP | 2014-525339 A | 9/2014 |
| JP | 2015514486 A | 5/2015 |
| JP | 2016-525428 A | 8/2016 |
| JP | 2016-530016 A | 9/2016 |
| WO | 90/09202 A1 | 8/1990 |
| WO | 93/07922 A1 | 4/1993 |
| WO | 94/07553 A1 | 4/1994 |
| WO | 94/15660 A1 | 7/1994 |
| WO | 95/13838 A1 | 5/1995 |
| WO | 96/09083 A1 | 3/1996 |
| WO | 96/32975 A1 | 10/1996 |
| WO | 97/00091 A1 | 1/1997 |
| WO | 97/10012 A1 | 3/1997 |
| WO | 9721457 A1 | 6/1997 |
| WO | 97/33638 A1 | 9/1997 |
| WO | 98/57686 A1 | 12/1998 |
| WO | 9857683 A1 | 12/1998 |
| WO | 99/29151 A1 | 6/1999 |
| WO | 99/38554 A1 | 8/1999 |
| WO | 99/59665 A1 | 11/1999 |
| WO | 00/25844 A1 | 5/2000 |
| WO | 01/30415 A2 | 5/2001 |
| WO | 01/30421 A2 | 5/2001 |
| WO | 200170304 A1 | 9/2001 |
| WO | 01/72357 A2 | 10/2001 |
| WO | 01/87384 A1 | 11/2001 |
| WO | 01/89607 A2 | 11/2001 |
| WO | 01/89613 A1 | 11/2001 |
| WO | 02/02165 A2 | 1/2002 |
| WO | 0204049 A1 | 1/2002 |
| WO | 02/34315 A1 | 5/2002 |
| WO | 02/38204 A2 | 5/2002 |
| WO | 02/56934 A2 | 7/2002 |
| WO | 02/56943 A2 | 7/2002 |
| WO | 02/72182 A1 | 9/2002 |
| WO | 03/62672 A1 | 7/2003 |
| WO | 03/90833 A1 | 11/2003 |

(56) References Cited

FOREIGN PATENT DOCUMENTS

| | | |
|---|---|---|
| WO | 2004/000397 A1 | 12/2003 |
| WO | 2004/032990 A2 | 4/2004 |
| WO | 2004098684 A2 | 11/2004 |
| WO | 2004/105841 A1 | 12/2004 |
| WO | 2005/018703 A2 | 3/2005 |
| WO | 2005/037350 A2 | 4/2005 |
| WO | 2005/072795 A2 | 8/2005 |
| WO | 2005070485 A1 | 8/2005 |
| WO | 2006/018617 A1 | 2/2006 |
| WO | 2006/037434 A1 | 4/2006 |
| WO | 2006/052737 A1 | 5/2006 |
| WO | 2006/069380 A1 | 6/2006 |
| WO | 2006/102676 A1 | 9/2006 |
| WO | 2006/104806 A2 | 10/2006 |
| WO | 2006/121921 A2 | 11/2006 |
| WO | 2007/017052 A1 | 2/2007 |
| WO | 2007/051563 A1 | 5/2007 |
| WO | 2007/056504 A1 | 5/2007 |
| WO | 2007/066152 A2 | 6/2007 |
| WO | 2007/073228 A1 | 6/2007 |
| WO | 2007/119178 A2 | 10/2007 |
| WO | 2008/001377 A2 | 1/2008 |
| WO | 2008/014908 A1 | 2/2008 |
| WO | 2008/057976 A2 | 5/2008 |
| WO | 2008/072229 A2 | 6/2008 |
| WO | 2008/076459 A1 | 6/2008 |
| WO | 2008/078318 A2 | 7/2008 |
| WO | 2009/019438 A1 | 2/2009 |
| WO | 2009022132 A2 | 2/2009 |
| WO | 2009/043564 A1 | 4/2009 |
| WO | 2009/044401 A2 | 4/2009 |
| WO | 2009/046989 A2 | 4/2009 |
| WO | 2009043000 A1 | 4/2009 |
| WO | 2009/069064 A1 | 6/2009 |
| WO | 2009/125398 A2 | 10/2009 |
| WO | 2009/144085 A2 | 12/2009 |
| WO | 2010/078227 A1 | 7/2010 |
| WO | 2010/078242 A1 | 7/2010 |
| WO | 2010/089313 A1 | 8/2010 |
| WO | 2011/075105 A1 | 6/2011 |
| WO | 2011/090955 A1 | 7/2011 |
| WO | 2011/090956 A2 | 7/2011 |
| WO | 2011101378 A1 | 8/2011 |
| WO | WO 2011/101378 A1 | 8/2011 |
| WO | 2011110872 A1 | 9/2011 |
| WO | 2011/124631 A1 | 10/2011 |
| WO | 2011/129175 A1 | 10/2011 |
| WO | 2011/131778 A1 | 10/2011 |
| WO | 2011/131780 A2 | 10/2011 |
| WO | 2011/131781 A1 | 10/2011 |
| WO | 2011/133823 A1 | 10/2011 |
| WO | 2011/156373 A1 | 12/2011 |
| WO | 2012/003221 A1 | 1/2012 |
| WO | 2012/032411 A2 | 3/2012 |
| WO | 2012/040528 A1 | 3/2012 |
| WO | 2012145752 A2 | 10/2012 |
| WO | 2012/160157 A1 | 11/2012 |
| WO | 2012168691 A1 | 12/2012 |
| WO | 2013036602 A1 | 3/2013 |
| WO | 2013058697 A1 | 4/2013 |
| WO | 2013/115843 A1 | 8/2013 |
| WO | 2014/132293 A1 | 9/2014 |
| WO | 2014/179117 A1 | 11/2014 |
| WO | 2014/179774 A1 | 11/2014 |
| WO | 2014/194183 A2 | 12/2014 |
| WO | 2015/048803 A2 | 4/2015 |
| WO | 2015048791 A1 | 4/2015 |
| WO | 2015/078868 A1 | 6/2015 |
| WO | 2015/091758 A1 | 6/2015 |
| WO | 2015/091850 A1 | 6/2015 |
| WO | 2015/114158 A1 | 8/2015 |
| WO | 2015/114428 A1 | 8/2015 |
| WO | 2015118358 A1 | 8/2015 |
| WO | 2015/163009 A1 | 10/2015 |
| WO | 2016/087626 A1 | 6/2016 |
| WO | 2016/087627 A1 | 6/2016 |
| WO | 2016141082 A1 | 9/2016 |
| WO | 2017/022639 A1 | 2/2017 |
| WO | 2017/161076 A1 | 9/2017 |
| WO | 2018/222521 A1 | 12/2018 |
| WO | 2019/224782 A1 | 11/2019 |
| WO | 2020/120087 A1 | 6/2020 |
| WO | 2020/193468 A1 | 10/2020 |

OTHER PUBLICATIONS

U.S. Appl. No. 13/873,335 by Filman, filed Apr. 30, 2013.
U.S. Appl. No. 13/874,017 by Cabiri, filed Apr. 30, 2013.
U.S. Appl. No. 13/874,085 by Cabiri, filed Apr. 30, 2013.
U.S. Appl. No. 13/874,121 by Degtiar, filed Apr. 30, 2013.
U.S. Appl. No. 13/892,905 by Cabiri, filed May 13, 2013.
U.S. Appl. No. 13/964,651 by Gross, filed Aug. 12, 2013.
U.S. Appl. No. 14/193,692 by Gross, filed Feb. 28, 2014.
U.S. Appl. No. 14/258,661 by Cabiri, filed Apr. 22, 2014.
U.S. Appl. No. 14/553,399 by Cabiri, filed Nov. 25, 2014.
U.S. Appl. No. 14/593,051 by Gross, filed Jan. 9, 2015.
U.S. Appl. No. 14/638,525 by Filman, filed Mar. 4, 2015.
U.S. Appl. No. 14/683,193 by Cabiri, filed Apr. 10, 2015.
U.S. Appl. No. 14/715,791 by Cabiri, filed May 19, 2015.
U.S. Appl. No. 14/725,009 by Bar-El, filed May 29, 2015.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
U.S. Appl. No. 29/479,307 by Norton, filed Jan. 14, 2014.
U.S. Appl. No. 60/997,459, filed Oct. 2, 2007.
West Introduces the Daikyo Crystal Zenith RU Prefillable Syringe, Pharmaceutical Online, Jun. 2008, downloaded from webpage: http://www.pharmaceuticalonline.com/article.mvc/west-introduces-prefillab- le-syringe-system, Download date: Jan. 2009, original posting date: Jun. 2008, 2 pages.
Office Action dated Apr. 22, 2016 in CN Application No. 2014102892041.
Office Action dated Apr. 5, 2010 in U.S. Appl. No. 12/244,666 by Gross.
Office Action dated Apr. 5, 2010 in U.S. Appl. No. 12/244,688 by Gross.
Office Action dated Aug. 13, 2015 in U.S. Appl. No. 14/553,399 by Cabiri.
Office Action dated Aug. 14, 2017 in CN Application No. 201410178318.9.
Office Action dated Aug. 15, 2013 in CN Application No. 200880117084.X.
Office Action dated Aug. 26, 2014 in CN Application No. 201180006567.4.
Office Action dated Aug. 6, 2014 in EP Appl. No. 11 707 942.6.
Office Action dated Dec. 1, 2015 in CN Application No. 201410289204.1.
Office Action dated Dec. 10, 2013 in CN Application No. 201180006567.4.
Office Action dated Dec. 15, 2017 in U.S. Appl. No. 15/269,248, by Cabiri.
Office Action dated Dec. 17, 2013 in JP Application No. 2012-529808.
Office Action dated Dec. 4, 2017 in CN Application No. 201410178374.2.
Office Action dated Dec. 9, 2016 in U.S. Appl. No. 14/593,051, by Gross.
Office Action dated Feb. 16, 2017 in CN Application No. 2014101783189.
Office Action dated Feb. 20, 2015 in U.S. Appl. No. 13/521,181 by Cabiri.
Office Action dated Feb. 21, 2012 in U.S. Appl. No. 12/689,249.
Office Action dated Feb. 24, 2015 in U.S. Appl. No. 14/258,661 by Cabiri.
Office Action dated Feb. 24, 2017 in U.S. Appl. No. 13/964,651, by Gross.
Office Action dated Feb. 28, 2014 in CN Application No. 201180006571.0.

(56) References Cited

OTHER PUBLICATIONS

Office Action dated Feb. 4, 2014 in EP Application No. 11 707 942.6.
Office Action dated Jan. 10, 2017 in U.S. Appl. No. 14/193,692, by Gross.
Office Action dated Jan. 30, 2013 in CN Application No. 200880117084.X.
Office Action dated Jan. 8, 2013 in JP Application No. 2010-527595.
Office Action dated Jan. 8, 2014 in U.S. Appl. No. 13/521,167 by Cabiri.
Office Action dated Jul. 13, 2011 in U.S. Appl. No. 12/559,563 by Cabiri.
Office Action dated Jul. 2, 2012 in U.S. Appl. No. 13/272,555 by Cabiri.
Office Action dated Jul. 28, 2020 in Japanese Application No. 2018-538074.
Office Action dated Jul. 3, 2017 in CN Application No. 2014101783742.
Office Action dated Jul. 31, 2015 in U.S. Appl. No. 13/521,181 by Cabiri.
Office Action dated Jul. 7, 2014 in U.S. Appl. No. 12/244,666 by Gross.
Office Action dated Jun. 10, 2016 in U.S. Appl. No. 13/964,651 by Gross.
Office Action dated Jun. 14, 2018 in U.S. Appl. No. 13/874,121, by Degtiar.
Office Action dated Jun. 2, 2016 in CN Application No. 2014101783189.
Office Action dated Jun. 3, 2014 in JP Application No. 2010-527595.
Office Action dated Jun. 4, 2015 in U.S. Appl. No. 13/667,739 by Cabiri.
Office Action dated Jun. 9, 2017 in EP Application No. 14166591.9.
Office Action dated Jun. 9, 2017 in EP Application No. 14166596.8.
Office Action dated Mar. 1, 2018 in EP Application No. 14166592.7.
Office Action dated Mar. 10, 2015 in CN Application No. 201180006567.4.
Office Action dated Mar. 10, 2015 in U.S. Appl. No. 12/244,666 by Gross.
Office Action dated Mar. 10, 2015 in U.S. Appl. No. 13/643,470 by Alon.
Office Action dated Mar. 30, 2018 in U.S. Appl. No. 14/850,450 by Gross.
Office Action dated Mar. 31, 2015 in JP Application No. 2012-550068.
Office Action dated Mar. 5, 2014 in CN Application No. 200880117084.X.
Office Action dated May 1, 2015 in U.S. Appl. No. 14/638,525 by Filman.
Office Action dated May 13, 2015 in CN Application No. 201380025566.3.
Office Action dated May 14, 2018 in EP Application No. 08808111.2.
Office Action dated May 16, 2012 in U.S. Appl. No. 12/615,828.
Int'l Search Report and Written Opinion dated Dec. 15, 2016 in Int'l Application No. PCT/US2016/056258.
Int'l Search Report and Written Opinion dated Dec. 8, 2016 in Int'l Application No. PCT/US2016/056227.
Int'l Search Report and Written Opinion dated Nov. 30, 2016 in Int'l Application No. PCT/US2016/056223.
Int'l Search Report and Written Opinion dated Dec. 2, 2016 in Int'l Application No. PCT/US2016/056210.
Int'l Search Report and Written Opinion dated Nov. 28, 2016 in Int'l Application No. PCT/US2016/056218.
Int'l Search Repport (Partial), dated Dec. 20, 2016 in Int'l Application No. PCT/US2016/056247.
Int'l Search Report and Written Opinion dated Dec. 5, 2016 in Int'l Application No. PCT/US2016/056233.
Int'l Search Report and Written Opinion dated Apr. 21, 2017 in Int'l Application No. PCT/US2016/068367.
Int'l Search Report and Written Opinion dated May 15, 2017 in Int'l Application No. PCT/US2016/068371.
Int'l Search Report and Written Opinion dated Mar. 27, 2017 in Int'l Application No. PCT/US2016/056247.
Int'l Search Report and Written Opinion dated Jan. 26, 2017 in Int'l Application No. PCT/US2016/056213.
European Search Report (Partial) dated Mar. 8, 2017 in EP Application 16193157.1.
Extended Search Report dated Jul. 7, 2017 in EP Application No. 16193157.1.
Office Action dated May 18, 2018 in EP 14166591.9.
Office Action dated May 23, 2014 in U.S. Appl. No. 13/472,112 by Cabiri.
Office Action dated May 24, 2017 in U.S. Appl. No. 13/874,121, by Degtiar.
Office Action dated May 25, 2021 in Japanese Office Action 2018-538073.
Office Action dated May 3, 2012 in CN Application No. 200880117084.X.
Office Action dated May 31, 2016 in U.S. Appl. No. 14/593,051 by Gross.
Office Action dated May 4, 2017 in CN Application No. 2014101836665.
Office Action dated May 5, 2015 in CN Application No. 201180006571.0.
Office Action dated May 7, 2015 in JP Application No. 2012-550069.
Office Action dated Nov. 10, 2016 in U.S. Appl. No. 13/874,121, by Degtiar.
Office Action dated Nov. 13, 2017 in U.S. Appl. No. 14/193,692, by Gross.
Office Action dated Nov. 2, 2014 in CN Application No. 201180006571.0.
Office Action dated Nov. 21, 2014 in U.S. Appl. No. 13/429,840 by Cabiri.
Office Action dated Nov. 21, 2014 in U.S. Appl. No. 13/472,112 by Cabiri.
Office Action dated Nov. 25, 2016 in U.S. Appl. No. 13/874,017, by Cabiri.
Office Action dated Nov. 4, 2013 in EP Application No. 11 709 234.6.
Office Action dated Nov. 5, 2013 in JP Application No. 2010-527595.
Office Action dated Nov. 5, 2014 in U.S. Appl. No. 13/643,470 by Alon.
Office Action dated Nov. 8, 2017 in U.S. Appl. No. 13/874,121, by Degtiar.
Office Action dated Oct. 13, 2020 in Japanese Application No. 2018-538073.
Office Action dated Oct. 2, 2018 in JP Application No. 2018-535062 (Year: 2018).
Office Action dated Oct. 28, 2011 in U.S. Appl. No. 12/615,828.
Office Action dated Oct. 28, 2016 in CN Application No. 2014101783742.
Office Action dated Oct. 5, 2016 in U.S. Appl. No. 13/964,651, by Gross.
Office Action dated Oct. 6, 2017 in U.S. Appl. No. 14/861,478, by Cabiri.
Office Action dated Oct. 9, 2014 in U.S. Appl. No. 13/873,335.
Office Action dated Sep. 18, 2015 in U.S. Appl. No. 13/874,085 by Cabiri.
Office Action dated Sep. 2, 2010 in U.S. Appl. No. 12/244,688 by Gross.
Office Action dated Sep. 2, 2014 in JP Application No. 2012-550068.
Office Action dated Sep. 2, 2014 in JP Application No. 2012-550069.
Office Action dated Sep. 28, 2017 in IN Application No. 2528/DELNP/2010.
Office Action dated Sep. 29, 2013 in CN Application No. 201080040968.7.
Office Action dated Sep. 30, 2010 in U.S. Appl. No. 12/689,250, by Cabiri.
Office Action dated Sep. 30, 2015 in U.S. Appl. No. 13/667,739 by Cabiri.

(56) References Cited

OTHER PUBLICATIONS

Office Action dated Sep. 6, 2011 in U.S. Appl. No. 12/345,818.
Office Action dated Sep. 9, 2015 in U.S. Appl. No. 13/643,470 by Alon.
Office Action dated Aug. 17, 2021 in Indian Application No. 201827027625.
Office Action dated Nov. 6, 2015 in U.S. Appl. No. 14/715,791 by Cabiri.
Office Action dated Oct. 6, 2020 in Japanese Application No. 2018-538527.
Partial European Search Report dated Nov. 24, 2015 in EP Application No. 14166592.7.
Search Report dated Oct. 14, 2016 in CN Application No. 2014101783742.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
U.S. Appl. No. 13/429,840 by Cabiri, filed Mar. 26, 2012.
U.S. Appl. No. 13/472,112 by Cabiri, filed May 15, 2012.
U.S. Appl. No. 13/521,167 by Cabiri, filed Jul. 9, 2012.
U.S. Appl. No. 13/521,181 by Cabiri, filed Jul. 9, 2012.
U.S. Appl. No. 13/643,470 by Alon, filed Oct. 25, 2012.
Communication Pursuant to Rules 161 and 162 dated Apr. 6, 2018 in EP Application No. 16784688.0.
Copaxone(Registered), Innovative Drugs, Teva Pharmaceuticals, downloaded from webpage: http://levapharm.com/copaxone/, Download date: Jan. 2009, original posting date: unknown, 3 pages.
Daikyo Crystal Zenith(Registered) polymer, Manufactured by Daikyo Seiko, Lid. (Jun. 25, 2008).
Definition of Monolithic. In Merriam-Webster's online dictionary. Retrieved from https://www.merriam-webster.com/dictionary/monolithic (Year 2021).
English translation of an Office Action dated Jan. 30, 2013 in CN Application No. 200880117084.X.
English translation of an Office Action dated Mar. 5, 2014 in CN Application No. 200880117084.X.
Extended European Search Report dated Aug. 7, 2014 in EP Application No. 14174774.
Extended European Search Report dated Feb. 12, 2018 in EP Application No. 17191756.0.
Extended European Search Report dated Feb. 13, 2017 in EP Application No. 16171626.1.
Extended European Search Report dated Feb. 23, 2015 in EP Application No. 14166591.9.
Extended European Search Report dated Feb. 23, 2015 in EP Application No. 14166596.8.
Extended European Search Report dated Jul. 3, 2017 in EP Application No. 16190054.3.
Extended European Search Report dated Mar. 27, 2014 in EP Application No. 14154717.4.
Extended European Search Report dated Mar. 8, 2016 in EP Application No. 14166592.7.
Extended European Search Report dated Nov. 10, 2016 in EP Application No. 08808111.2.
Extended European Search Report dated Jul. 28, 2020 in European Application No. 20172466.3.
Extended Search Report dated Aug. 7, 2014 in EP Application No. 14171477.4.
Int'l Preliminary Report on Patentability dated Nov. 22, 2017 in Int'l Application No. PCT/US2016/068371.
Int'l Search Report and Written Opinion dated Jan. 12, 2011 in Int'l Application No. PCT/US2010/048556; Written Opinion.
Int'l Search Report and Written Opinion dated Jul. 6, 2017 in Int'l Application No. PCT/US2017/022966.
Int'l Preliminary Report on Patentability dated Jan. 8, 2018 in Int'l Application No. PCT/US2016/056218.
Int'l Preliminary Report on Patentability dated Apr. 7, 2010 in Int'l Application No. PCT/IL2008/001312.
Int'l Preliminary Report on Patentability dated Aug. 2, 2012 in Int'l Application No. PCT/US2011/021604.
Int'l Preliminary Report on Patentability dated Feb. 7, 2013 in Int'l Application No. PCT/US11/21605.
Int'l Preliminary Report on Patentability dated Jan. 18, 2018 in Int'l Application No. PCT/US2016/056210.
Int'l Preliminary Report on Patentability dated Jan. 18, 2018 in Int'l Application No. PCT/US2016/056213.
Int'l Preliminary Report on Patentability dated Jan. 18, 2018 in Int'l Application No. PCT/US2016/056223.
Int'l Preliminary Report on Patentability dated Jan. 18, 2018 in Int'l Application No. PCT/US2016/056227.
Int'l Preliminary Report on Patentability dated Jul. 16, 2015 in Int'l Application No. PCT/US2013/078040.
Int'l Preliminary Report on Patentability dated May 14, 2015 in Int'l Application No. PCT/US2013/065211.
Int'l Preliminary Report on Patentability dated Nov. 27, 2014 in Int'l Application No. PCT/US2013/039465.
Int'l Preliminary Report on Patentability dated Nov. 30, 2017 in Int'l Application No. PCT/US2016/068367.
Int'l Preliminary Report on Patentability dated Nov. 9, 2018 in Int'l Application No. PCT/US2016/056238.
Int'l Preliminary Report on Patentability dated Oct. 9, 2014 in Int'l Application No. PCT/US2013/033118.
Int'l Preliminary Report on Patentability dated Sep. 1, 2011 in Int'l Application No. PCT/US2010/048556.
Int'l Search Report and Written Opinion dated Apr. 3, 2014 in Int'l Application No. PCT/US2013/078040.
Int'l Search Report and Written Opinion dated Aug. 5, 2013 in Int'l Application No. PCT/US2013/033118.
Int'l Search Report and Written Opinion dated Jan. 7, 2014 in Int'l Application No. PCT/US2013/065211.
Int'l Search Report and Written Opinion dated Jul. 12, 2017 in Int'l Application No. PCT/US2016/056238.
Int'l Search Report and Written Opinion dated Jul. 26, 2013 in Int'l Application No. PCT/US2012/039465.
Int'l Search Report and Written Opinion dated Jul. 31, 2014 in Int'l Application No. PCT/US2014/033598.
Int'l Search Report and Written Opinion dated May 13, 2009 in Int'l Application No. PCT/IL2008/001312.
Int'l Search Report dated Apr. 26, 2010 in Int'l Application No. PCT/US2009/069552.
Int'l Search Report dated Jun. 17, 2011 in Int'l Application No. PCT/US2011/021604.
Int'l Search Report dated Oct. 12, 2011 in Int'l Application No. PCT/US11/21605.
Int'l Search Report dated Sep. 22, 2011 in Int'l Application No. PCT/IL11/00368; Written Opinion.
Int'l Written Opinion dated Jul. 19, 2012 in Int'l Application No. PCT/US11/21605.
International Preliminary Report on Patentability and Written Opinion dated Jul. 5, 2011 in International Application No. PCT/US2009/069552.
Notice of Allowance dated Aug. 24, 2015 in U.S. Appl. No. 29/479,307 by Norton.
Offce Action dated Sep. 21, 2010 in U.S. Appl. No. 12/244,666 by Gross.

* cited by examiner

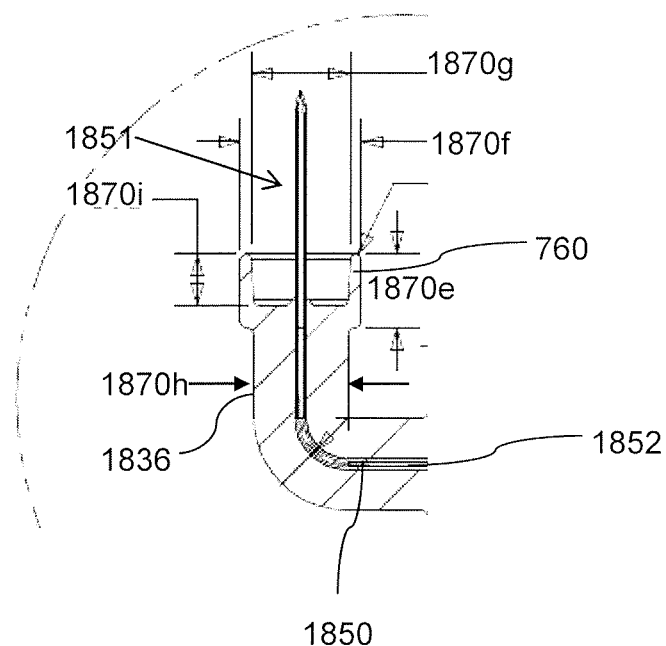
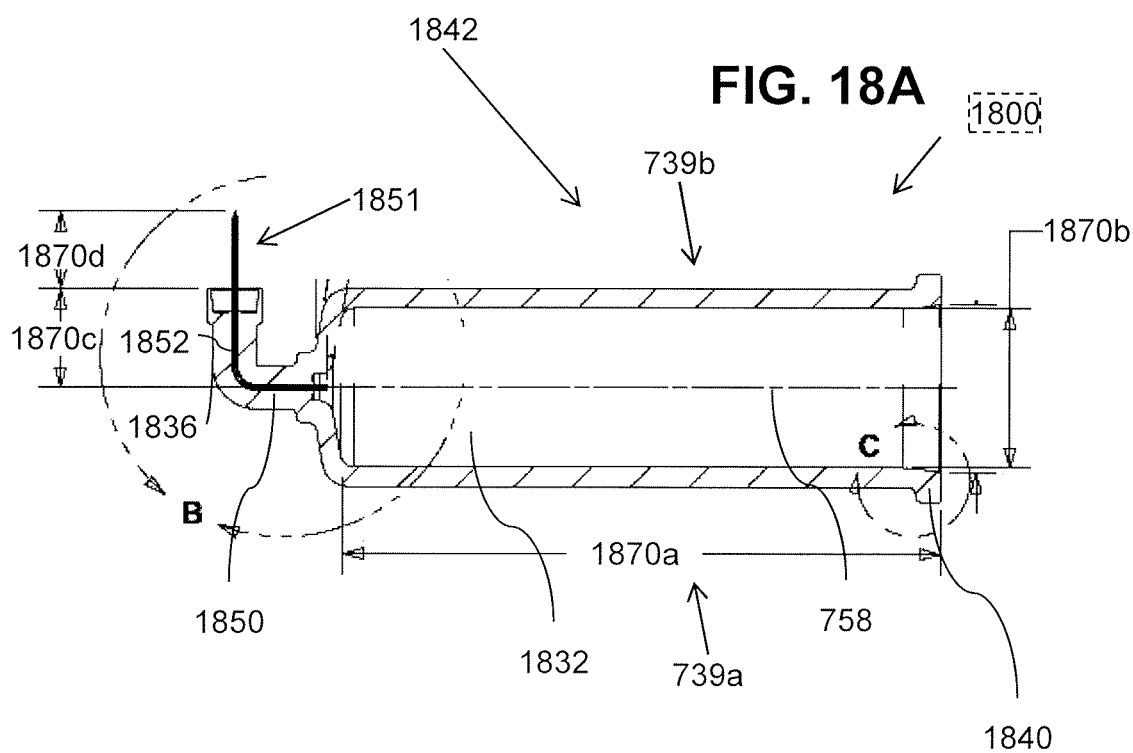
FIG. 18B
FIG. 18A

ANGLED SYRINGE PATCH INJECTOR

CROSS-REFERENCE TO RELATED APPLICATIONS

This application claims the benefit of co-pending U.S. patent application Ser. No. 15/204,542, titled "Angled Syringe Patch Injector", filed on Jul. 7, 2016, which claims the benefit of priority under 35 USC § 119(e) of U.S. Provisional Patent Application No. 62/281,536 filed Jan. 21, 2016 and U.S. Provisional Patent Application No. 62/284,806 filed Oct. 9, 2015, the contents of each of which are incorporated herein by reference in their entireties.

FIELD AND BACKGROUND OF THE INVENTION

The present invention, in some embodiments thereof, relates to an angled syringe and, more particularly, but not exclusively, to a sterile and/or preloaded syringe with an angled tip.

Injections using a standard syringe involve holding a syringe perpendicularly to the skin, inserting a needle through the skin and pushing a plunger. The material to be injected sometimes requires to be inserted into the blood supply and sometimes the material is simply inserted under the skin. The amount of material that can be inserted into the blood supply on finding a suitable blood vessel is larger than the amount that can be inserted under the skin since, without entering the blood circulation, the material injected subcutaneously tends to pool at a single location and causes that location to swell up before any dispersal is able to occur.

Thus, in some cases, it is advantageous to carry out the injection more slowly, say over a time period of ten seconds to three minutes or longer. However, holding a syringe in the same position for over a minute is not easy, and movement may be irritating to the patient. Thus, it has been proposed to provide a means for injecting material into the body that rests on the skin as the injection is carried out.

Examples include U.S. Pat. Nos. 6,500,150, 6,824,529, and 6,843,782, which disclose a drug delivery device having a base member defining a skin-contacting surface, a syringe serving as a reservoir for the drug, and means for expelling drug from the syringe. The syringe is connected to the base member such that the longitudinal axis of the syringe is substantially parallel to the skin surface. A delivery needle is in communication with the syringe. The needle has an angled bend, which directs the tip of the needle substantially perpendicular to the skin-contacting surface. In use, the tip of the needle is adapted to penetrate the skin of the subject.

For such relatively slow release, an automatic expulsion device has also been suggested. U.S. Pat. No. 5,858,001 discloses a liquid drug delivery device adhered to the skin of a subject by a base member defining a skin-contacting surface having an adhesive coating. A columnar cartridge serves as reservoir for the drug and is incorporated in a housing, which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator, which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

If using an injector device then the syringe cartridge may be preloaded and needs to be kept sterile during the process of locating it in the injector. U.S. Patent Publication No. 20140163526 discloses an automated injection device, which may be loaded with a standard type syringe and/or hypodermic needle. Optionally the syringe may be preloaded. The syringe may be loaded into the injector in a sterile state with needle cover in place. The injector includes a fastener, such as an adhesive base. The fastener may assist a user to hold the injector steady on the skin of a patient for an extended period. For example, the injector may be used to give injections of volume ranging between 0.5 and 3.0 ml over a time period ranging between 30 seconds and 10 minutes.

U.S. Pat. No. 1,125,887 relates to providing "a syringe needle with a bendable guard or shield that permits of a needle being safely bent to a desired angle or inclination, without danger of the needle being injured, cracked, or the walls thereof collapsed by the pliers or instrument employed for bending the needle."

U.S. Pat. No. 8,603,028 relates to a "handheld injection device includes a first housing having a first axis and a second housing having a second axis. In one embodiment, the second housing is configured to support a needle. In one embodiment, the first axis and a second axis form an adjustable angle between about 180 degrees and about 90 degrees."

U.S. Pat. No. 8,496,862 relates that, "A collet mechanism that holds a cannula during molding of a syringe includes first and second arms that form an internal cavity. Each arm has a proximal end and a distal end. The first and second arms are in a closed position when the distal ends are moved toward the internal cavity and are in an open position when the distal ends are positioned away from the internal cavity. First and second cannula guides respectively are mounted proximate the distal ends of the first and second arms and extend into the internal cavity. The first and second cannula guides clamp a portion of the cannula to hold the cannula when the first and second arms are in the closed position."

U.S. Pat. No. 8,721,603 relates that, "A prefilled syringe for injecting medicament into a patient includes a barrel constructed of a polymeric material, a cannula and a hub. The barrel has a diameter, a longitudinal axis, a proximal end and a distal end. The cannula has a proximal end and a tip opposite the proximal end. The proximal end of the cannula is fixed to the distal end of the barrel. The cannula is positioned generally coaxially with the longitudinal axis. The hub is integrally formed with the distal end. The hub includes a rib section and a cap. The rib section has a generally cruciform cross-section taken along a rib plane. The rib plane is generally perpendicular to the longitudinal axis. The cap has a generally U-shaped cross-section taken along a longitudinal plane. The longitudinal plane is generally parallel to the longitudinal axis."

Additional background art includes U.S. Pat. No. 6,189,292. U.S. Patent Publication No. 20130253434, U.S. Patent Publication No. 2009/093,792, U.S. Pat. No. 7,967,795.

The existing art suffers from a number of drawbacks, including being difficult to manufacture, or difficult to pre-fill and then keep sterile when fitting in the injector. Furthermore, the fluid path may be made up of a long length of unprotected needle, which is hard to keep sterile for any length of time, especially if the needle has a bend in it.

SUMMARY OF THE INVENTION

According to an aspect of some embodiments of the invention, there is provided a syringe comprising: a body including a reservoir having a longitudinal axis; an extension extending from a distal end of the body, the extension including: an annular sealing ring for a sterile sealing cap the sealing ring having an axis oriented at an angle ranging between 30 to 150 degrees with respect the longitudinal axis of the reservoir, and a fluid path passing through at least a portion of the extension, at least a portion of the path circumscribed by the sealing ring.

According to some embodiments of the invention, the extension is integrally formed with the reservoir.

According to some embodiments of the invention, a first end of the fluid path is in communication with an interior of the reservoir.

According to some embodiments of the invention, the first end is in communication with a distal end of the reservoir.

According to some embodiments of the invention, a second end of the fluid path is in communication with an exterior surface of the extension.

According to some embodiments of the invention, a least a portion of the fluid path passes through a hollow tube embedded in the extension.

According to some embodiments of the invention, the hollow a tube is composed of at least 50% metal.

According to some embodiments of the invention, a portion of the tube protrudes out of the extension.

According to some embodiments of the invention, the portion of the tubes protrudes at substantially the same direction as the axis of the sealing ring.

According to some embodiments of the invention, the extension is insert molded around the tube.

According to some embodiments of the invention, the sealing surface includes a conical section.

According to some embodiments of the invention, the syringe further comprises: a substantially conical section around the fluid path According to some embodiments of the invention, the fluid path includes a bent tube insert molded into the extension.

According to some embodiments of the invention, the extension is rigidly connected to the reservoir to withstand a perpendicular force of a least 5N between the extension and the reservoir with a strain changing the angle by less than 2 degrees.

According to an aspect of some embodiments of the invention, there is provided a syringe cartridge comprising: a reservoir having a longitudinal axis; a molded extension rigidly extending from a distal portion of the reservoir, the extension including standard syringe adapter tip having an axis oriented at an angle of between 30 to 15 degrees with respect the longitudinal axis of the reservoir, and a fluid path passing inside the extension and exiting through the adapter tip.

According to some embodiments of the invention, the extension is integrally formed with the reservoir.

According to some embodiments of the invention, a first end of the fluid path is in communication with an interior of the reservoir.

According to some embodiments of the invention, a second end of the fluid path is in communication with an exterior surface of the extension.

According to some embodiments of the invention, a least a portion of the fluid path passes through a hollow tube embedded in the extension.

According to some embodiments of the invention, the hollow tube is composed of at least 50% metal.

According to some embodiments of the invention, the portion of the hollow tube embedded in the extension is bent.

According to some embodiments of the invention, the tip includes a standard syringe adapter.

According to some embodiments of the invention, the adapter includes at least one fitting selected from the group consisting of a slip lock, a luer adapter, a record adapter, an npt adapter, a three way adapter, a multi-way adapter, a threaded end, a panel mount fitting, a tube fitting, a fistula tip, a fitting for a sterility preserving needle cap and a pomeroy tip.

According to some embodiments of the invention, the extension is molded integrally with the reservoir.

According to some embodiments of the invention, the extension is a separate molding fixably attachable to the reservoir.

According to some embodiments of the invention, the extension is molded around a single length the tube.

According to some embodiments of the invention, the extension is insert molded around the tube.

According to some embodiments of the invention, the fluid path comprises a second needle parallel to the axis of the reservoir part, the tube being at the angle.

According to some embodiments of the invention, the extension is connected to the reservoir part radially away from the axis of the reservoir part.

According to some embodiments of the invention, the angle is selected such that the fluid path crosses an extension of the axis of the reservoir part.

According to some embodiments of the invention, a base wall of the cartridge reservoir part to which the extension is connected is angled towards the extension, the fluid path being within the extension, thereby to allow the reservoir part to be emptied into the fluid path.

According to some embodiments of the invention, an exposed end of the tube at the angle is beveled, the beveling being in a direction towards the reservoir.

According to some embodiments of the invention, the extension comprises a neck aligned with the axis of the reservoir part.

According to some embodiments of the invention, the neck has an "I" shaped profile.

According to some embodiments of the invention, the extension comprises at least one channel to allow the tube to be held during a molding process.

According to some embodiments of the invention, a length of the tube at the angle is exposed, the length being sufficient to accept a standard injection needle safety cover.

According to some embodiments of the invention, the tube includes a first end and a second end and an angle therebetween and/or wherein the angle is including is the at least a portion of the tube that is enclosed inside a molded part of the extension.

According to an aspect of some embodiments of the invention, there is provided a syringe cartridge ready to fill comprising: a sterile empty reservoir having a longitudinal axis and a proximal opening; a tip oriented at an angle of between 30 and 150 degrees with respect to the longitudinal axis of the reservoir, a sterile fluid path passing from a distal end of the reservoir to an opening from a distal portion of the tip; and a sterile sealing cap sealing around the distal portion of the tip.

According to some embodiments of the invention, the tip includes at least one fitting selected from the group consisting of a slip lock, a luer adapter, a record adapter, an npt adapter, a three way adapter, a multi-way adapter, a threaded end, a panel mount fitting, a tube fitting, a fistula tip, a fitting for a sterility preserving needle cap and a pomeroy tip.

According to some embodiments of the invention, the syringe cartridge further includes: a sterile hollow needle extending from the fluid path and a sterility protecting needle cap attached to the tip and protecting the needle.

According to an aspect of some embodiments of the invention, there is provided a method of manufacturing a cartridge for injection of a pharmaceutical substance comprising: supplying a syringe including a reservoir having an open proximal end and a hollow fluid path leading to an angled tip oriented at a finite angle to an axis of the reservoir and covered by a sealing cap; orienting the angled tip to fit into a nest tray of an automatic filling machine; inserting the syringe with the covered tip into the nest tray of an automatic filling machine; and sterilizing the covered syringe while inserted into the nest together with the nest.

According to some embodiments of the invention, the supplying includes: inserting an angled needle having a first end and a second end and an angle therebetween into a mold, the mold defining a reservoir for a pharmaceutical at the first end and a jacket extending from the reservoir beyond the angle towards the second end around the needle and leaving a length of needle exposed for insertion of a needle cap; and inserting molding material into the mold to insert mold the cartridge around the mold.

According to some embodiments of the invention, the method further comprises: filling the reservoir with a pharmaceutical substance in a vacuum; inserting a plunger into the reservoir behind the pharmaceutical substance; and removing the vacuum to seal the pharmaceutical substance with the plunger into the reservoir to form a filled cartridge.

According to some embodiments of the invention, the method further comprises inserting the filled cartridge into an injector.

According to some embodiments of the invention, the method comprises activating the injector when placed along skin of the subject to be injected by aligning a longitudinal axis of the reservoir parallel with a surface of the skin and inserting the angled tip of the fluid path into the skin.

According to some embodiments of the invention, the method comprises operating a motor or a torque spring or push spring in the injector to push the plunger to expel the pharmaceutical substance into the fluid path and around the angle to carry out the injection.

According to some embodiments of the invention, the method further comprises: filling the reservoir with a pharmaceutical substance; inserting a plunger into the reservoir behind the pharmaceutical substance; and forcing the plunger to a liquid level of the pharmaceutical substance while expelling air through a venting tube, thereby to seal the pharmaceutical substance with the plunger into the reservoir to form a filled cartridge.

According to an aspect of some embodiments of the invention, there is provided a syringe cartridge comprising: a reservoir; and an extension extending from the reservoir, the extension including a molded superstructure, a tip oriented at a finite angle with respect to an axis of the reservoir the including an adapter for a sterility preserving cap, the superstructure supported rigidly to the reservoir to resist a force of removing the cap from the tip; and a fluid path passing through the extension from the reservoir to an opening in the tip; at least a portion of the fluid path circumscribed by the adaptor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 18A-18B are perspective views of an alternate syringe with an angled extension in accordance with an embodiment of the present invention;

DESCRIPTION OF SPECIFIC EMBODIMENTS OF THE INVENTION

Figure 1:
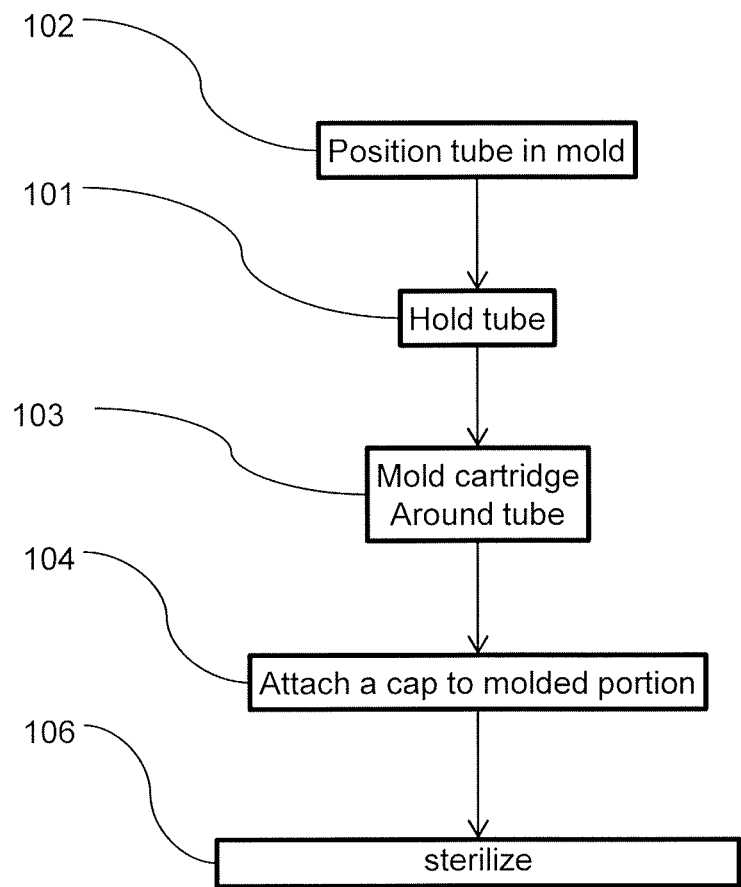
FIG. 1 is a flow chart illustration of a method of manufacturing a syringe with an angled extension in accordance with an embodiment of the present invention.

The present invention, in some embodiments thereof, relates to an angled syringe and, more particularly, but not exclusively, to a sterile and/or preloaded syringe with an angled tip.

An aspect of some embodiments of the present invention relates to a syringe including a cylindrical reservoir with a fluid path extension formed by inserting molding over a hollow tube. Optionally, some or all of the extension and/or fluid path may be curved and/or at a finite angle to the longitudinal axis of the reservoir. In some embodiments, the extension includes a mount for a protective cap. In some embodiments, a needle protrudes from the extension and/or is covered by the cap. Optionally, the protruding needle is an extension of the hollow tube.

In some embodiments, the extension and the reservoir may be formed as an integrally molded unit. Alternatively or additionally, the extension may be molded separately from the reservoir and/or attached thereto. Optionally, the fluid path may include a needle, which is optionally bent. The needle is optionally insert molded into a molded component of the extension and/or the reservoir. For example, the molded component may be made of Daikyo Resin CZ (Crystal Zenith) or other Cyclic Olefin Polymer (COP) or any moldable material suitable to use with drug product. Alternatively or additionally, molded components may be made of, for example, polycarbonate and/or polypropylene and/or other polymers.

In one embodiment, the syringe cartridge or capsule is molded around a hollow tube, which is initially inserted into a mold. Optionally, the tube may be bent.

For example, the tube may be formed (for example bent to shape, treated and/or cleaned) and then inserted into the mold. Optionally, following molding, the bend in the needle is fully and/or partially enclosed by the cartridge. A remaining straight portion is optionally protected by a standard needle cover. The needle may exit the reservoir part eccentrically from the axis of the cartridge and/or cross over the axis. Eccentric mounting optionally facilitates keeping a larger portion of the needle and/or extension within the profile of the reservoir. For example, this may facilitate a smaller protrusion from the profile of the reservoir and/or a longer straight distal part of the extension. A longer extension optionally allows more robust mounting of a cover and/or sterile seal to the extension. For example, a standard needle cover may fit to the extension and/or maintain sterility according to medical standards over the long term (for example for a period ranging from a day to a week and/or a week to a month and/or a month to a year and/or a year to 5 years. Optionally, the tube and/or a needle may exit the molding at an angle substantially equal to the angle of the axis of the cap mount.

In some embodiments, the extension may have openings (for example windows and/or channels) through which guides and/or clamps are inserted during molding to support the tube. Optionally, the cross section of the extension is configured to allow access to the openings and/or the tube. Optionally, structural reinforcements of the extension may be distanced from the tube. For example, the extension may have an I-beam geometry wherein the tube passes through the web of the beam and is accessible via windows while the flange support members are on the periphery of the beam away from the tube.

An aspect of some embodiments of the present invention relates to a drug syringe and/or drug reservoir with an angled outlet and/or tip and/or extension. For example, the outlet may include a mount for a needle cap and/or a mount for a needle and/or a needle. Optionally, a needle protrudes from the outlet at an angle to the axis of the barrel of the syringe. Optionally the outlet and/or extension may include a mount for a needle cap and/or a needle fitting and/or a luer fitting; for example, the extension may be at an angle to the central axis of the barrel of the syringe, or may be offset from the central axis of the barrel of the syringe. Optionally the needle mount is rigidly attached to the reservoir of the syringe such that it does not bend significantly from the stress of pushing on and/or pulling off the needle cap.

In some embodiments, the extension includes a mount adapted to fit a standard needle cap. Optionally the extension may include ribs to stabilize the cap. For example, the ribs may have a full circular cross section and/or a cross-shaped cross section and/or an I-beam cross section. Optionally the extension may have a slip tapered portion and/or a luer lock. The extension optionally includes molding features such as a channel and/or a flange. Alternatively or additionally, a cap may have a non-standard shape and/or may be mounted to the extension and/or the barrel at an angle to a needle.

In some embodiments the extension and/or a distal portion thereof and/or the cap mount and/or the needle tip may be at an angle ranging between 88 and 92 degrees or between 85 and 95 degrees or between 90 and 100 degrees or between 70 and 110 degrees or between 50 and 130 degrees or between 30 and 150 degrees to the axis of the barrel and/or the interior space of the reservoir. Optionally the outlet and/or extension and/or the protruding needle may be rigidly connected to the reservoir. For example, a perpendicular force of 5 N or less (for example between 0 to 2 N and/or between 2 to 5 N) on the on the extension (for example at the base of the needle and/or at the bent portion of the extension and/or at a needle mount of the extension) may change the finite angle by less than 2 degrees. In some embodiments, the extension may protrude beyond the profile of the walls of the reservoir.

In some embodiments, the extension may include a sealing surface. For example, the surface may seal to the inner surface of a protective cap, for example a needle cover. Sealing the cap to the extension optionally protects the tip of the extension from contamination. For example, the sealing surface may have a shape that is substantially a conical section. Optionally the apex angle of the conical section may range between 0-2 degrees and/or between 2-6 degrees and/or between 6-15 degrees Optionally, the diameter of the cap mount may range between 0-3 mm and/or 3-7 mm and/or 7-10 mm and/or 10 to 20 mm. Optionally, the length of the cap mount may range between 0-5 mm and/or 5-15 mm and/or 15-20 mm. Optionally, the distance between the distal end of the cap mount and the distal tip of the extension may range between 4-20 mm as required needle insertion for a specific drug and/or injection target.

In some embodiments, the fluid path may be mounted eccentrically and/or bend around to cross a center line of the reservoir. For example, the path may be configured to balance its weight. For example, the weight may be balanced so that the syringe hangs substantially vertically in a nest and/or tray of a filling machine.

The design of the flow path may reduce the length of a protrusion from the profile of the reservoir (for example to reduce the size of a hole in the nest). For example, protrusions (for example including a needle and/or needle cap) may be limited to less than 10 mm and/or less than 25 mm and/or less than 40 mm from an outer edge of the projection of the cylindrical walls of the reservoir and/or of the outer wall of the reservoir and/or less than less than 25 mm and/or less than 35 mm and/or less than 60 mm a direction perpendicular to the longitudinal axis of the cylindrical reservoir.

An aspect of some embodiments relates to a fluid reservoir with an angled fluid path. Optionally the reservoir may be filled aseptically in a standard syringe filling machine. In some embodiments, the distal end of the syringe may include a novel geometry, for example the angled extension. In some embodiments, the proximal side of the cartridge may be formed like a standard syringe. For example, the proximal portion may be standard enough to fit a standard and/or minimally modified filling machine. For example, the modified syringe may fit into a modified nest, which fits into a conventional filling machine. Optionally the syringe is configured to be pre-filled with a drug using standard syringe filling equipment.

Optionally the extension includes a syringe tip for example having a built in needle and/or a needle mount and/or a mount for a protective cap at an angle to the axis of the barrel of the syringe. Optionally the distal side of the syringe is balanced enough to hang substantially vertically in a nest. For example, the syringe may hang at an angle between 0-1 degree and/or 1-2 degrees and/or 2 to 3 degrees and/or 3 to 5 degrees (for example the "angle of the cartridge may be the angle of the longitudinal axis. Optionally, part of the distal end may bulge and/or protrude outside the cross section of the barrel of the syringe. The bulge and/or protrusion is optionally small enough to fit in an optionally modified syringe nest. For example, the length of a bulge and/or protrusion may be limited to 1-4 mm and/or 4-10 mm and/or 10-20 mm and/or 20 to 40 mm.

In some embodiments, the fluid reservoir may comprise a cartridge for an auto-injector. Optionally the cartridge may be pre-filled in a sterile aseptic environment using standard equipment for filling syringes. Filling is optionally prior to insertion into the injector. Optionally, the injector itself need not be sterile and/or not as strictly sterile as the cartridge.

In some embodiments, a bent fluid path may be produced by plastically bending a hollow tube. The tube is optionally cleaned after bending (for example to remove any particles produced during the bending). Optionally a superstructure is added to the tube. For example, the superstructure may be molded around the tube (for example using techniques of insert molding). Optionally, a portion of the tube may be exposed. For example, one or both ends of the tube may protrude from the superstructure. Optionally or additionally, the superstructure may include a mount for a sterility protecting needle cover.

In some embodiments, the extension is associated with a reservoir. For example, the extension may be integrally formed with a reservoir and/or attached to a reservoir. For example, the reservoir and extension together may be included in a medicine cartridge (e.g. a prefilled syringe and/or a cartridge for a drug delivery device). Optionally, the entire cartridge including the reservoir and/or the extension and/or the cover is sterilized. For example, the cartridge is sterilized as a sealed unit. Optionally the cartridge may be filled and sealed with a stopper. For example, the cartridge may be configured for filling in a conventional and/or minimally modified syringe filling machine.

An aspect of some embodiments of the present invention relates to an elastic and/or super elastic and/or shape changing sterile fluid path. For example, an elastic and/or super elastic and/or shape changing bent fluid path may be straightened and/or partially straightened. Optionally, with the fluid path in its straight form, the fluid path may be capped with a sterility protective covering (for example a needle cap).

Optionally the elastic flow path is associated with a reservoir. For example, the fluid path may be integrally formed with the reservoir and/or attached to a reservoir. For example, the reservoir and fluid path together may constitute a medicine cartridge (e.g. a prefilled syringe and/or a cartridge for a drug delivery device). Optionally, the entire cartridge including the reservoir and/or the flow path and/or the cover is sterilized. Optionally the cartridge may be filled and sealed with a stopper. For example, the cartridge may be configured for filling in a conventional and/or minimally modified syringe filling machine. Before use, the flow path is optionally restored to its bent form.

An aspect of the present invention relates to an asymmetric syringe with reduced dead space. In some embodiments, a plunger seal may be shaped to drive fluid from the center axis of the syringe barrel towards an off center fluid outlet fluid path. For example, the plunger seal may be configured to contact a central portion of the distal inner wall of the reservoir before contacting a peripheral portion of the wall from which the fluid path exits the barrel.

For example, the distal inner wall of the reservoir may be conical and/or concave while the plunger seal may be conical and/or convex with a sharper opening angle than the opening angle of the distal inner wall of the syringe. Optionally the inner distal wall of the syringe may be angled with respect to the plunger seal and/or the axis of the barrel. For example, the distal inner wall of the barrel may be angled to contact the plunger seal on a side opposite the outlet fluid path before contacting the plunger seal on the side of the fluid outlet. The plunger seal optionally has a round cross section. For example, the plunger seal may be made of Chlorobutyl coated with PTFE layer, and/or Bromobutyl or EPDM or other suitable sealing material and/or material suitable for use with a drug product and the syringe over the product shelf life.

In order to improve drainage into the eccentrically located needle, the distal wall of the reservoir may be angled slightly towards the edge containing the needle.

DETAILED EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Manufacturing a Syringe

FIG. 1 is a flow chart illustration of a method of manufacturing a syringe with an angled extension in accordance with an embodiment of the present invention. The extension and/or a hollow needle may be oriented at an angle of for example between 30 to 150 degrees to the longitudinal axis of a cylindrical internal cavity of the barrel of the syringe. A fluid path may be molded into the syringe between an internal cavity of the barrel and the extension and/or needle. Optionally, the syringe may be filled in an aseptic environment and/or the sterility of a needle may be protected by a cap. In some embodiments, the syringe may be filled using conventional and/or a minimally modified filling machine.

In some embodiments, a method of manufacturing the cartridge for pharmaceutical substance may involve inserting 102 an angled tube into a mold. For example the angled tube may include a needle having an angle or bend along its length. The mold may define a reservoir for holding a pharmaceutical, For example, the reservoir may be located at one end of the tube. Optionally a jacket extends from the reservoir along the tube to a location beyond the bend and towards the far (distal) end of the tube. Optionally, the jacket leaves a length of tube exposed.

In some embodiments, molding material may be inserted into the mold. For example, the cartridge may be molded 103 around the angled needle. Optionally, during molding 103 the tube may be held 101 in place. Optionally, one or both ends of the tube may be held and/or protected from blockage during molding. For example, an end may be held and/or protected during molding 103 by an end mount. Optionally the end mount may include a collet and/or a pin to hold 101 an end of the tube and/or prevent molding material from entering and/or blocking the tube. In some embodiments, one or more locations along the length of the tube may be held 101. For example, a gripper 101 may be used to hold the tube. Optionally, the mold may include openings to allow insertion of a gripper into the mold and/or through the molding resin. For example, the gripper may to stabilize the tube during molding 103.

In some embodiments, the molded cartridge will include a mount for a needle cap. For example, a standard needle cap may be mounted 104 to the molded portion of the cartridge. Optionally the cap seals over a tip of the cartridge and/or seal around an exposed portion of a needle. The cartridge with the needle cap mounted 104 over the needle is optionally sterilized 106 as one assembly. Optionally, the cap is removably attached 104 to the mount. For example, before use, a user may remove the cap. In some embodiments, after use of the device, the cap may be returned to protect the needle. Alternatively or additionally, the cap may be discarded after removal.

Filling a Syringe

Figure 2:
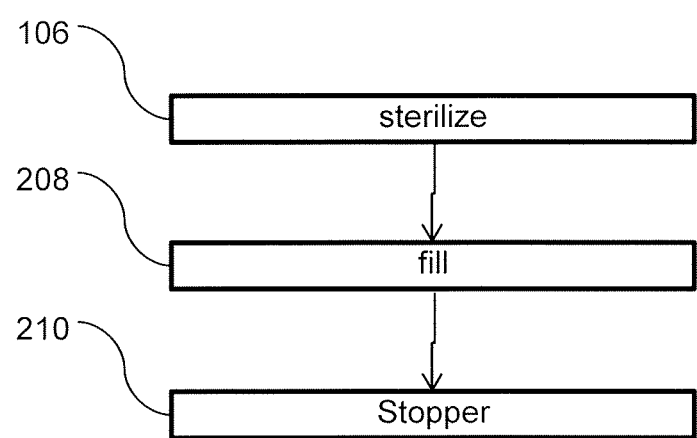
FIG. 2 is a flow chart illustration of a method of filling a cartridge in accordance with an embodiment of the present invention.

FIG. 2 is a flow chart illustration of a method of filling a syringe in accordance with an embodiment of the current invention. In some embodiments, following sterilization 106, a cartridge may be placed in a standard filling plant. Optionally the cartridge includes a protective cap. The reservoir is optionally filled 208 with a pharmaceutical substance. After filling the syringe may be stoppered 210.

Optionally filling 208 and/or stoppering 210 are performed under a vacuum. For example, after filling 208 a stopper is inserted into the reservoir under vacuum. As an alternative, the reservoir is simply filled 208 and/or stoppered 210 without using a vacuum. For example, a venting tube may be inserted during stoppering 210.

In some embodiments, the cartridge may be molded 103 with protrusions to allow standard equipment (for example a robot arm) to grab, hold and/or manipulate the cartridge. A plunger is optionally inserted into the reservoir behind the pharmaceutical substance. For example, the stopper may be inserted into a proximal opening of the reservoir. Optionally the vacuum is removed. In some embodiments, pressure behind the stopper will drive the stopper into the reservoir to the location of the pharmaceutical substance. For example, the stopper may seal the pharmaceutical substance and/or the reservoir to form a filled cartridge.

Optionally the sterility of the cartridge and/or the pharmaceutical substance may be preserved and/or guaranteed for lengthy periods of time. In the event of using the venting tube, the plunger is simply pushed to the liquid level of the inserted pharmaceutical, with air being expelled through the venting tube. Then the venting tube is removed and the plunger is sealed in position. During filling, the needle may be oriented horizontally or vertically as appropriate.

In some embodiments, a syringe may be molded 103 with a cylindrical internal cavity and/or an extension and/or a hypodermic needle. The extension and/or the hypodermic needle are optionally oriented at an angle between 30 to 150 degrees to a longitudinal axis of the internal cavity of the syringe. A fluid path may connect between the internal cavity and the extension and/or needle. Optionally the fluid path may be included inside the hollow of the needle. For example the fluid path may be bent. Optionally the syringe may be molded 103, for example, from polymer. The bent fluid path optionally, passes through the polymer.

Optionally, the cylindrical space may have a circular and/or non-circular cross section (for example an oval cross-section). The fluid path may also be a connection between two or more tubes, and/or may include an additional sealing process and/or joining piece for a joint between the tubes.

In some embodiments, the fluid path may be formed by insert molding 103 a tube (for example a bent needle) into the molded component. For example, the needle may be hollow. One end of the needle is optionally in fluid communication with the internal cavity of the syringe and/or a second end of the needle optionally projects from the syringe. For example, the second end of the needle may project at an angle of between 30 and 150 degrees to an axis of the barrel of the syringe. Optionally the second end of the needle may be configured for insertion through the skin of a subject, for example, the second end of the needle may be sharpened and/or beveled. Optionally, the needle may project from an extension.

For example, the extension may include a mount for a needle cap. Alternatively or additionally, the second end of the embedded needle may lead to the extension. For example, the extension may have a mount for a hypodermic needle.

In some embodiments, the exposed length of the needle may be suitable for performing an injection. For example, the exposed length of the needle may be suitable for intradermal injection and/or have gauge ranging for example between 24 G to 30 G and/or length ranging for example from 7-10 mm and/or the exposed length of the needle may be suitable for subcutaneous injection and/or have gauge ranging for example between 23 G to 28 G and/or length ranging for example from 9-28 mm and/or the exposed length of the needle may be suitable for intramuscular injection and/or have gauge ranging for example between 18 G to 23 G and/or length ranging for example from 24-40 mm and/or the exposed length of the needle may be suitable for intraveneous injection and/or have gauge ranging for example between 15 G to 22 G and/or length ranging for example from 24-40 mm.

In some embodiments, the exposed part of the needle may be covered with a sterile sealing needle cap. For example, the extension may include a mount for the needle cap. For example, the mount may include a sealing surface to seal tightly to the cap and/or preserve sterility. Optionally the sealing surface may have an annular form and/or a form of a conic section. Optionally the mount may include a physical connector to hold the cap rigidly inhibiting movement of the cap with respect to the extension.

For example, the cap may be held stably sealed to the extension when exposed to forces of up 1 kg and/or between 1-2 kg and/or between 2 to 5 kg. For example, the force may be applied in any direction and/or at any location (for example producing a torque).

In some embodiments, during the molding 103 process, the needle may be supported at one or more points. For example, the needle may be supported on a middle section and/or on a projecting end and/or on an end connecting to the internal cavity of the syringe. For example, an end of the needle may be supported by an end mount. For example, the end mount may include a collet and/or a pin. Optionally, for a hollow needle, the end mount may prevent the hollow end of the needle from being blocked by the molded material. Optionally the needle may be supported along the flow path, for example as will be explained herein below.

Once the syringe has been molded 102, it is optionally capped 104 with a cap. For example, the cap may seal the distal end of the syringe and/or preserve its sterility. In some embodiments, the extension may have a standard cap mount and/or the cap may fit over the protruding part of a needle. Optionally the cap may include a standard needle cap.

In some embodiments, a rigid cap may be rigidly mounted on the end of the extension. The cap optionally covers the needle and/or the end of the extension. Alternatively or additionally, the cap and/or the extension may be flexible and/or articulated. Optionally the needle cap protects the needle from contamination and/or physical damage. For example, the needle cap may seal over the end of the extension and/or the needle. The cap is optionally oriented at the same angle as the needle and/or the tip of the extension. Optionally the end of the extension is beveled and/or oriented to allow the needle cap to be pushed onto the extension and/or pulled off in the orientation direction of the extension for example between 30 and 150 degrees from the angle of the axis of the barrel of the syringe.

Optionally, the cap will be compliant with national and/or international standards for example for protective and/or sterile needle caps for example International Standards Organization, ISO 8537:2007, ISO 594-1:1986, ISO 7864: 1993, ISO 9626, ISO 7864:1993 standards and/or other standards such as those of the US National Institutes of Health (NIH) and/or US Food and Drug Administration (FDA) and/or US National Institute of Standards and Technology (NIST). For example a needle cap may include a flexible needle shield (FNS) and/or a rigid needle shield (RNS) and/or a thermoplastic elastomer rigid needle shield (TERNS). Examples of commercial needle shields include West 7025/55 and 7025/65 and Datwyler FM 27 and Stelmi 4800 GS.

In some embodiments, a non-standard needle cap may be used. For example, the cap may be mounted at a different angle than the extension orientation and/or the needle. For example, a needle cap may fit over the distal end of the syringe (for example the barrel of the syringe) and/or cover the extension and/or needle. Optionally the cap may be pushed onto the syringe and/or removed from the syringe in a direction parallel to the axis of the syringe barrel.

In some embodiments, the cap may cover a needle and/or the extension of the syringe, but may leave clear the proximal end of the syringe and/or a proximal opening of the syringe. For example, the cap may only cover a small portion of the distal side of the syringe. For example, the cap may cover between 0.01 to 2% of the syringe and/or between 2 to 5% and/or between 5 to 20% and/or between 20 to 50% and/or between 50 to 90% of the surface of the syringe and/or of the length of the syringe including the extension. Optionally, the cap covers the entire portion of the needle protruding from the syringe.

In some embodiment, the syringe and/or the needle and/or the needle cap may be sterilized 106. Optionally they may be assembled and then sterilized 106 as a single unit. Alternatively or additionally, the syringe and/or the extension may be sterilized 106 separately from the needle and/or the needle cap. Optionally, the syringe and/or the extension may be sterilized 106 while supported on a support tray and/or while enclosed in a closed and/or sealed tub.

In some embodiments, the syringe may be filled 208. For example, the syringe may be filled 208 with a drug in a standard and/or a minimally modified aseptic filling machine. Optionally the syringe may be filled while the needle in place on the syringe and/or with a needle cap attached. Optionally the drug may be a liquid. Optionally a drug is introduced into the internal cavity of the reservoir through a proximal opening of the syringe. Optionally the proximal opening is stoppered 210. For example, stoppering may include sealing the proximal opening of the syringe with a plunger seal for example after filling.

In some embodiments, the cartridge is inserted into a drug discharge device, for example an injector device. Optionally, cartridge is loaded into the injector in a filled and/or sterile state. The loading action is typically carried out with the needle cap in place. For example, the injector may not be guaranteed to be sterile to the same degree as the contents of the syringe. The injector device may then be supplied to the patient. The needle cap may optionally be removed for use by the patient and/or a medical helper and/or a doctor and/or a pharmacist.

In some embodiments, a cartridge may be installed to the delivery device before assembly of the device and/or before shipping the device to a retailer and/or a health provider and/or a user. Alternatively or additionally, the cartridge may be installed into the drug delivery device by a user, for example a health provider (for example a nurse and/or a pharmacist and/or a doctor and/or a health aid) and/or a subject of the injection (e.g. a patient receiving the drug) and/or a caretaker.

In some embodiments, an assembled injector, with the cartridge installed, may be supplied to a user. Optionally as supplied to the user, the cartridge and/or extension and/or the needle may be sterile and/or covered with the protective cap. Optionally, the injector may have a needle shield latch. For example, while the needle cap is in place the needle shield latch may be in an open position, allowing the access to the needle cap. For example, when the needle shield latch is in the open position there may be space for the cap and/or a cap remover to protrude out of the injector. For example, in the open position, the needle shield latch may retract. In some embodiments the needle shield latch may pivot and/or slide from one position and/or state to another. Alternatively or additionally, the cartridge and/or the injector may be supplied to the user separately and/or may be assembled by the user.

Figure 3:
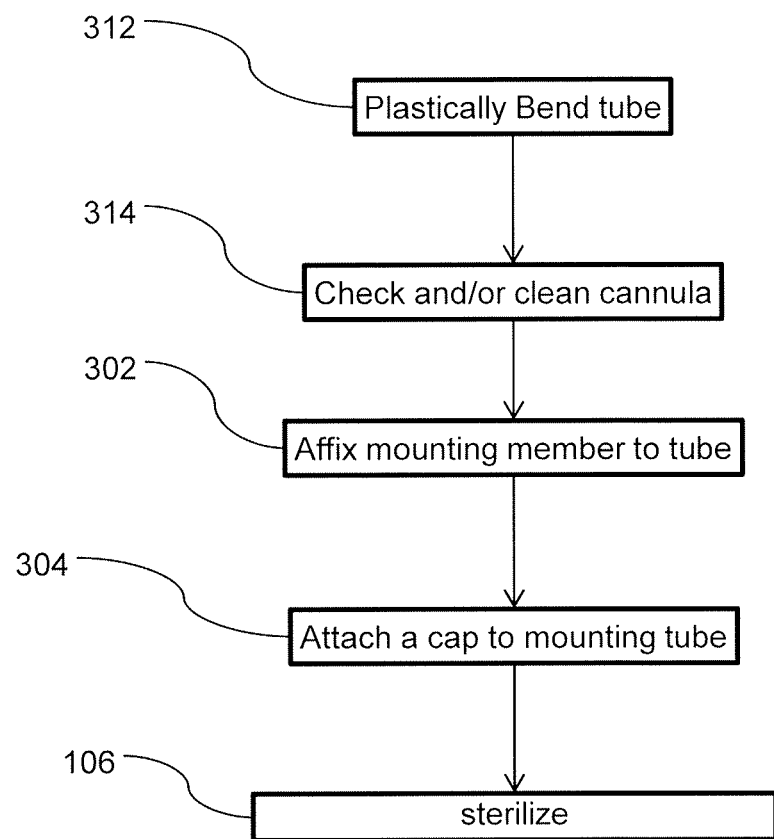
FIG. 3 is a flow chart illustration of a method of manufacturing a syringe with an angled needle in accordance with an embodiment of the present invention.

FIG. 3 is a flow chart illustrating manufacture of a syringe with an angled tip in accordance with an embodiment of the present invention. The syringe is optionally configured to enable one or more kinds of injections of fluid at one or more preset directions and/or to support needle insertion at one or more directions into the skin. Optionally a flow path is connected to the distal wall of a reservoir. In some embodiments, a tube (for example a hollow needle) is bent 312 to form a flow path.

For example, a proximal portion of the flow path may be parallel to and/or at an angle of between 0 to 30 degrees to a longitudinal axis of a reservoir. Additionally or alternatively, a distal portion of the flow path may be at an angle between 30 to 150 degrees to the axis of the reservoir.

In some embodiments, the tube is cleaned 314 after bending, for example to remove particles that were formed in the bending process. Optionally, cleaning is preformed prior to molding. In some embodiments, the needle may not be cleaned after bending. The needle may also inspected visually for example to identify tip damage and/or checked for example with airflow for example to identify cases of partial and/or full occlusion.

In some embodiments, a mounting member is optionally affixed 302 to the tube. Optionally the mounting member is integral to and/or attached to the reservoir. A cap is optionally attached 304 to the mounting member.

In some embodiments, the tube may be cleaned 314 before being attached 302 to the reservoir and/or mounting member. Alternatively or additionally, the reservoir and/or tube and/or mounting member may be cleaned 314 as a unit. Optionally, cleaning 314 is performed before attaching 304 the protective cap. The cap may surround an exposed portion of the tube and/or protect sterility of the part of the tube and/or part of the mounting member. The capped tube and/or mounting member and/or reservoir are optionally sterilized 106 together.

In some embodiments, the mounting member may be integral to and/or rigidly attached to the reservoir. Alternatively or additionally, the mounting member may be flexibly attached to the reservoir. Alternatively or additionally, a mounting member and/or the cap may be directly connected to the needle.

An Elastic Extension

Figure 4:
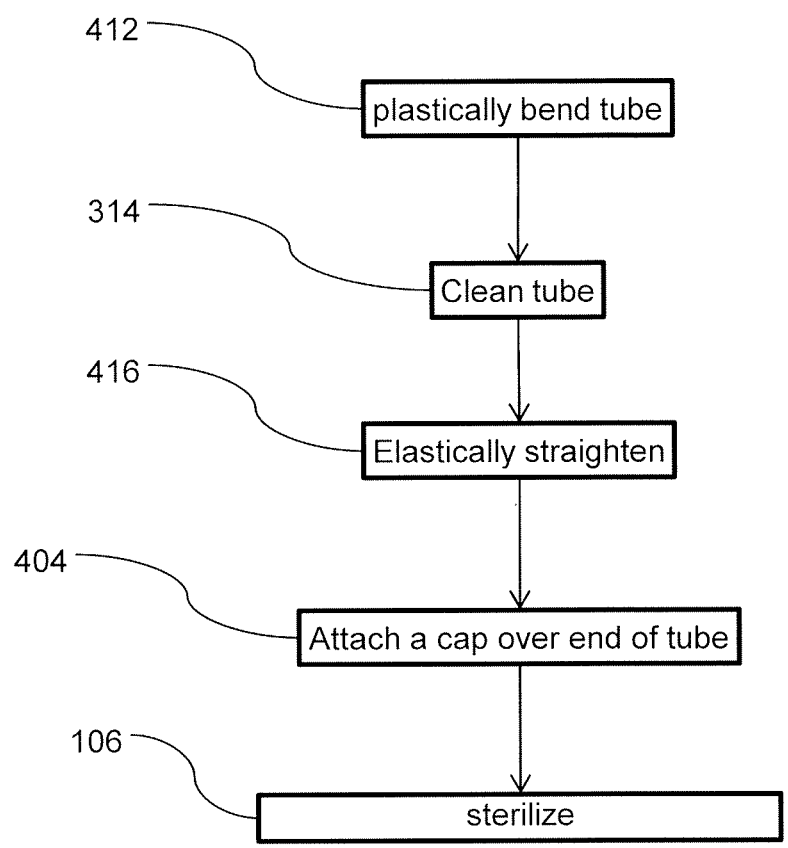
FIG. 4 is a flow chart illustration of a method of manufacturing a syringe with an angled elastic needle in accordance with an embodiment of the present invention.

FIG. 4 is a flow chart illustration of a syringe with an angled tip in accordance with an embodiment of the present invention. In some embodiments, a tube may be made of a super elastic and/or shape memory material. Optionally the tube will be plastically bent 412 to form an angled extension. The tube is optionally elastically straightened 416 and capped 404. The capped syringe is optionally sterilized 106 and/or filled. Prior to and/or during use, the device is uncapped and/or the needle restored to its bent shape.

Exemplary Cartridges

Figure 5:
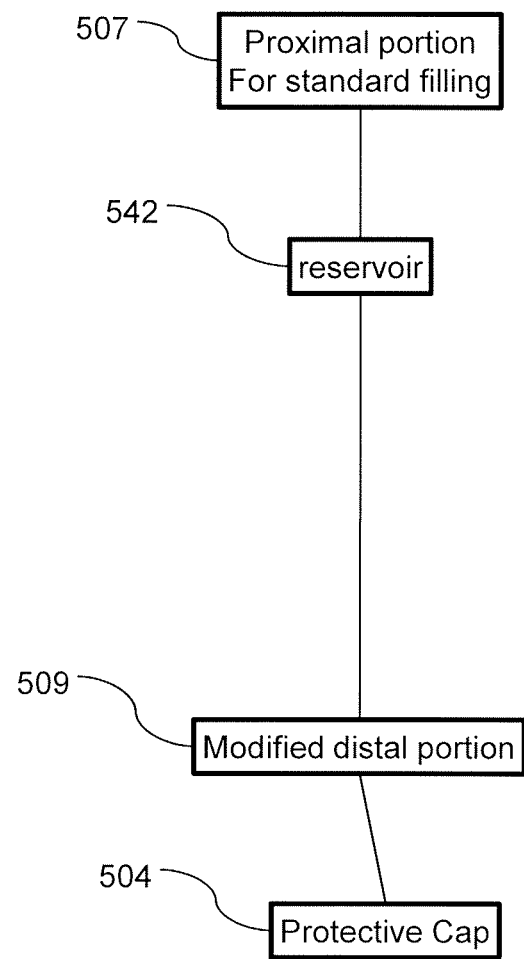
FIG. 5 is a block diagram illustration of a medicine cartridge in accordance with an embodiment of the present invention.

FIG. 5 is a block diagram of a syringe cartridge with a modified distal end in accordance with an embodiment of the current invention. In some embodiments, an injector cartridge may have a proximal portion 507 that is similar to a conventional syringe. For example, a proximal portion may include a flange and a proximal opening. Optionally the proximal portion is configured for handling by a conventional and/or minimally modified automated syringe filling machine. Optionally, a distal portion 509 of the cartridge may have features that are customized for use in a drug delivery device. The modifications in the distal portion cartridge may be configured to avoid interfering with filing of the cartridge.

In some embodiments, a cartridge may include a reservoir 542. The reservoir optionally includes an approximately cylindrical cavity. For example, the cavity may fit a syringe plunger. Optionally the proximal end of the reservoir may include a flange. For example, the flange may be configured to hold the reservoir to a nest tray of the filling machine. The flange optionally includes modifications, for example for helping to orient the cartridge during filling.

In some embodiments, a distal end of reservoir 542 may include modifications for an automated drug delivery device. For example, the distal end of the reservoir may include an angled extension and/or an angled needle. Optionally, part of the distal portion may protrude beyond a silhouette of the cartridge. The distal portion of the cartridge may be designed to reduce a length of the protrusion. For example, an angled extension is optionally offset and/or set back to reduce the size of a protrusion.

Alternatively or additionally, a protrusion may be balanced. For example, reducing a size of a protrusion may facilitate fitting of one or more cartridges into a nest of a filling machine. For example, balancing a protrusion may improve the angle at which a cartridge hangs in a filling next and/or may facilitate automatic handling of the cartridge.

Figure 6:
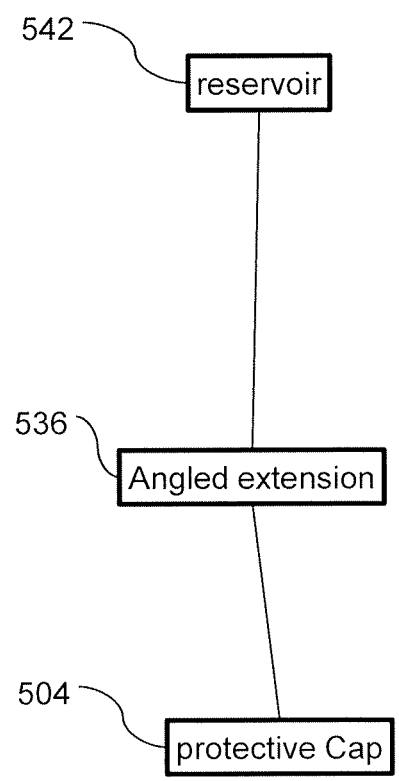
FIG. 6 is a block diagram illustration of a medicine cartridge with an angled extension in accordance with an embodiment of the present invention.

FIG. 6 is a block diagram of a syringe cartridge with an extension 536 in accordance with an embodiment of the present invention. In some embodiments, a distal portion of the extension has a longitudinal axis at a finite angle of between 30 to 150 degrees to the axis of the reservoir. In some embodiment, the cap may protect a distal portion of the extension and/or a protruding needle from contamination and/or from physical disruption. Optionally, cap 504 may be placed on angled extension 536.

For example, cap 504 may protect and/or cover a portion of angled extension 536 (for example a distal portion thereof) and/or a needle protruding therefrom. For example, while covering and/or protecting the distal portion of extension 536, needle cap 504 may leave part and/or all of reservoir 542 exposed. For example, cap 504 may leave a proximal opening of reservoir 542 exposed. For example, the proximal opening of reservoir 542 may be used to fill the reservoir while the distal end of extension 536 is protected by cap 504.

In some embodiments, cap 504 may act as a physical barrier to contamination of a distal portion of an extension. For example, cap 504 may reliably maintain container closure integrity over the cartridge shelf life with the defined storage conditions for the drug. In some embodiments, cap 504 may act as a shield against physical damage to a distal portion of an extension. For example, cap 504 may withstand forces without significant moving and/or without bending a protected needle and/or without breaking a sterility seal. For example, forces may include forces occurring during transportation, vibration and/or drop (for example dropping between 0 to 1 m and/or 1 to 3 m and/or 3 to 5 m) that may apply the acceleration and/or force to the syringe body, the extension and/or the cap.

In some embodiments, cap 504 may be reversibly connected to extension 536. For example, cap may be removable from extension 536 by linearly pulling away from extension 536. For example, the pulling force may range between 3N-10N. Alternatively or additionally, cap 504 may be threadably connected to extension 536.

In some embodiments, the distal portion of extension 536 may include an opening to a fluid path. The fluid path may connect the opening to a distal wall of reservoir 542. Additionally or alternatively, extension 536 may include a molded portion. For example, the molded portion of extension 536 may include the mount for protective cap 504. Optionally, a needle may protrude from the molded portion of extension 536. For example, the protruding portion of the needle and/or the mount of needle cap 504 may be oriented at the finite angle with respect to the axis of the reservoir.

In some embodiments, a distal portion of extension 536 may be oriented at the finite angle to the axis of reservoir 542. For example, the distal portion of extension 536 may include a needle mount and/or a straight portion of the protruding part of a needle. For example, a cap 504 may fit to the needle mount of the molded may cover and/or surround and/or protect a distal portion of extension 536 and/or a protruding portion of a needle. For example, cap 504 may surround the entire protruding portion of the needle. Optionally, while the cap 504 is covering and/or protecting the distal portion of extension 536, a proximal opening of reservoir 542 may remain uncovered. For example, leaving open the proximal opening of the reservoir may facilitate filling of the reservoir while the needle remains covered. Optionally, the entire protruding portion of the needle may be straight.

In some embodiments, a reservoir may include, for example, a bore with a cylindrical cavity. For example, the cylindrical cavity may be in a proximal portion of the bore. Optionally, the axis of the reservoir may be defined as the longitudinal axis of the cylindrical cavity.

Syringe with Off Centered Angled Extension

Figure 7A:
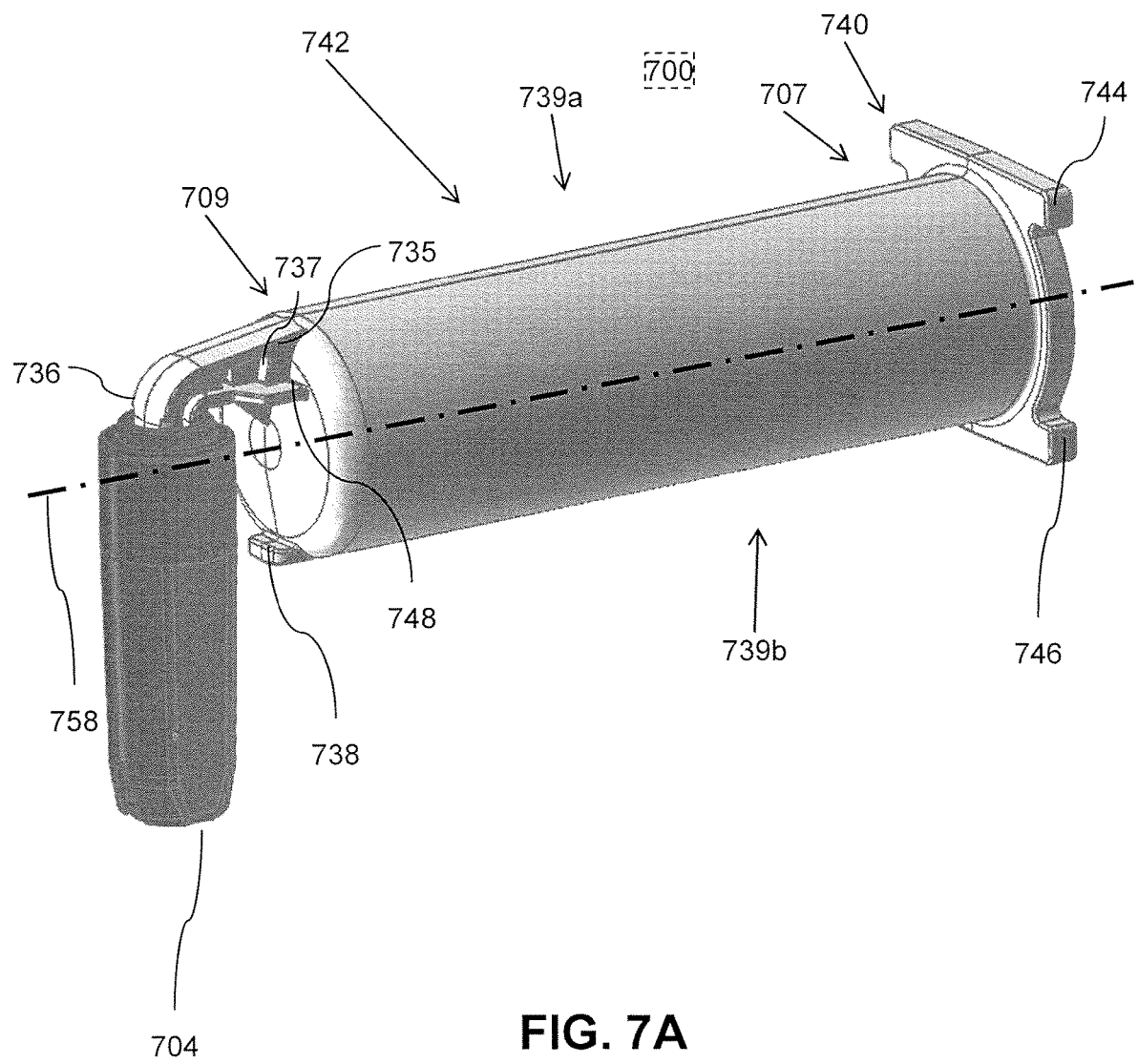
FIGS. 7A-7C are perspective views of a syringe with an angled extension mounted off center in accordance with an embodiment of the present invention.
Figure 7B:
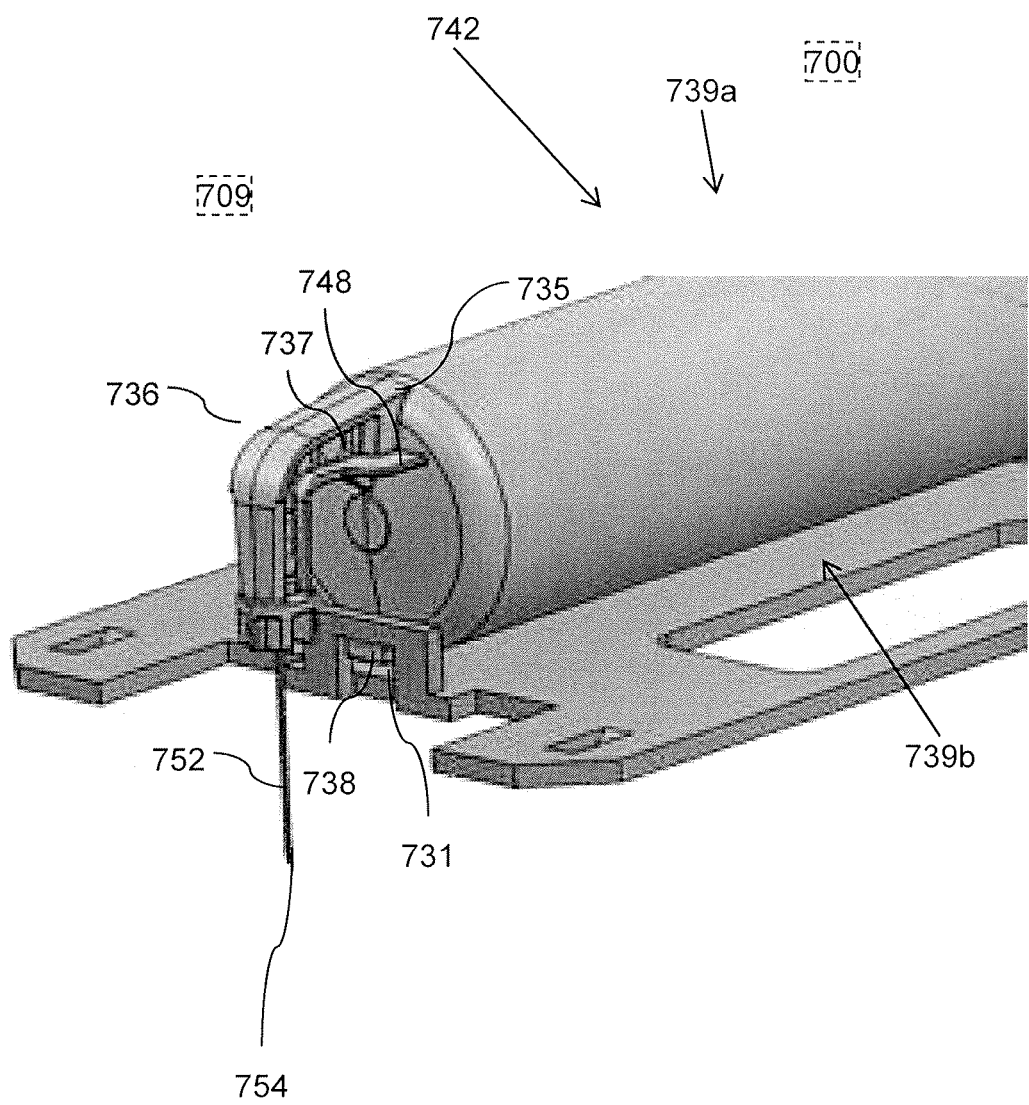
Figure 7C:
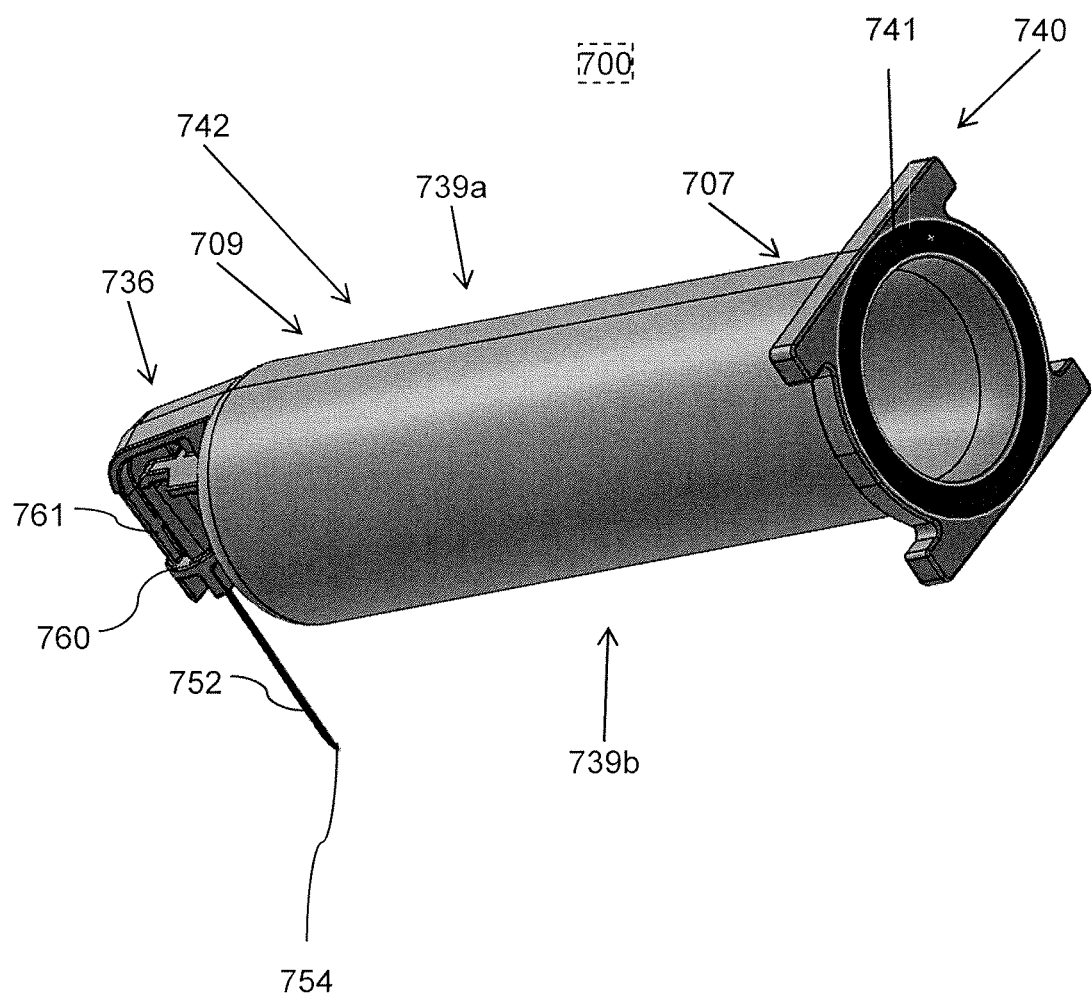

FIGS. 7A, 7B and 7C are perspective views of a syringe 700. Syringe 700 optionally includes a reservoir for a drug delivery device. Optionally, syringe 700 includes an angled extension 736 mounted on a bent arm off the center axis 758 of a cylindrical cavity 732 of a barrel 742 in accordance with an embodiment of the present invention. Optionally a fluid path connects to the cavity of the barrel and/or passes through extension 736. Optionally the bent arm is molded and/or formed in one piece with barrel 742. For example, extension 736 projects from a distal end 709 of barrel 742. Optionally the connection between the extension and the barrel is biased toward a side of the barrel. In some embodiments, a needle cap 704 is mounted on extension 736. Optionally, the extension bends back and/or crosses the profile of the reservoir.

In some embodiments, a flange 740 may be supplied on the proximal end 707 of syringe 700. For example, flange 740 may be used to hang barrel 742 from a support tray of an automatic filling machine. Optionally, features of the syringe including the flange may facilitate connection to a drug delivery device.

In some embodiments syringe 700 may include asymmetric features. For example, the fluid path may be connected non-centrically to the distal end of barrel 742. For example, extension 736 projects from a distal end 709 of barrel 742. Optionally the connection between extension 736 and barrel 742 is biased to the dorsal side 739a of barrel 742. In some embodiments, a needle cap 704 is mounted on extension 736 at an approximately right angle to axis 758. For example, cap 704 faces towards the ventral side 739b of barrel 742. Optionally extension 736 and/or the mount for cap 704 is set back from a ventral side 739b of barrel 742. For example setting back extension 736 and/or the mount for cap 704 may facilitate designing a device with a lower profile (for example because the length of the mounting does not add to the profile of the device).

For example, the end of the extension may be set back between 0 and 1 mm from the ventral edge of the reservoir and/or between 1 and 3 mm and/or between 3 and 10 mm and/or more than 10 mm from the ventral edge of the barrel. Alternatively or additionally, the extension may protrude beyond the edge of the ventral wall of the barrel.

For example, the end of the extension may protrude between 0 and 1 mm beyond the ventral edge of the reservoir and/or between 1 and 3 mm and/or between 3 and 10 mm and/or more than 10 mm beyond the ventral edge of the reservoir and/or barrel. In some embodiments, a cap mount may have a width (for example a diameter) ranging for example between 0 to 5 mm and/or between 5 to 10 mm and/or between 10 to 20 mm. In some embodiments, a width (for example a diameter) of a drug reservoir may range between 5 to 20 mm and/or between 10 to 14 mm and/or between 14 to 20 mm.

In some embodiments, syringe 700 may include a fitting. Optionally a snap and/or a fitting may be molded into a syringe. For example, a fitting may include a plastic snap, a rivet, a pin, a cut out, an indentation, a protuberance, a snap clamp, a catch, a ball fitting, a latch, a barb etc. For example, a tab 738 and/or an indentation and/or a protuberance (for example tab 738, and/or protuberance 744 and/or 746) may be included in a syringe. For example, a fitting may facilitate attachment of syringe 700 to a drug delivery device (for example an auto-injector).

In some embodiments, an indentation and/or a protuberance may be used to position syringe 700 and/or a cartridge in a delivery device. For example tab 738 and/or protuberance 744, 746 may interact with an interlocking part of an injection device, for example a protuberance and/or indentation and/or catch and/or hole in the delivery device, to position the cartridge in the delivery device. For example, tab 738 may facilitate positioning the distal end 709 of cartridge 700 into alignment with the delivery device. For example as illustrated in FIG. 7B tab 738 may fit into a slot 731. Optionally a fitting may include a snap connector. For example, an indentation and/or protuberance could interlock to a pin and/or a matching hole. A bevel and and/or cutout and/or tab 748 may optionally interact with a complementary part in a delivery device (for example clips and/or snaps and/or a hole in the delivery device for example, as illustrated in FIG. 7B).

In some embodiments a fluid path connecting between cavity 732 of barrel 742 and extension 736 may pass through and/or be molded integrally to a syringe 700. For example, the fluid path may pass through a molded extension of the reservoir. Optionally (for example as illustrated in FIG. 17B), a metal tube (for example needle 752) forms a portion of fluid path 750 (for example as shown in FIG. 17B). Optionally, dead space in fluid path 750 is reduced. For example, dead space may be reduced by include most and/or all of the fluid path inside needle 752, thus avoiding dead space in the plastic mold. For example, an embedded portion 753 of needle 752 forms a bent fluid path 750 to a protruding portion 751. Protruding portion 751 optionally protrudes straight out of extension 736 at substantially a right angle to axis 758 of the cavity 732 and/or the axis of barrel 742.

The protruding end of needle 752 is optionally beveled and/or sharpened to facilitate insertion through the skin of a subject.

In some embodiments, a beveled needle tip 754 is oriented to avoid obstruction of needle 752. For example, the opening of beveled needle tip 754 is directed distally. In the case where needle tip 754 is inserted into a subject by pivoting around the proximal end of the syringe and/or tends to plow proximally as it is inserted into the subject, facing the opening distally may prevent needle obstruction.

Figure 15:
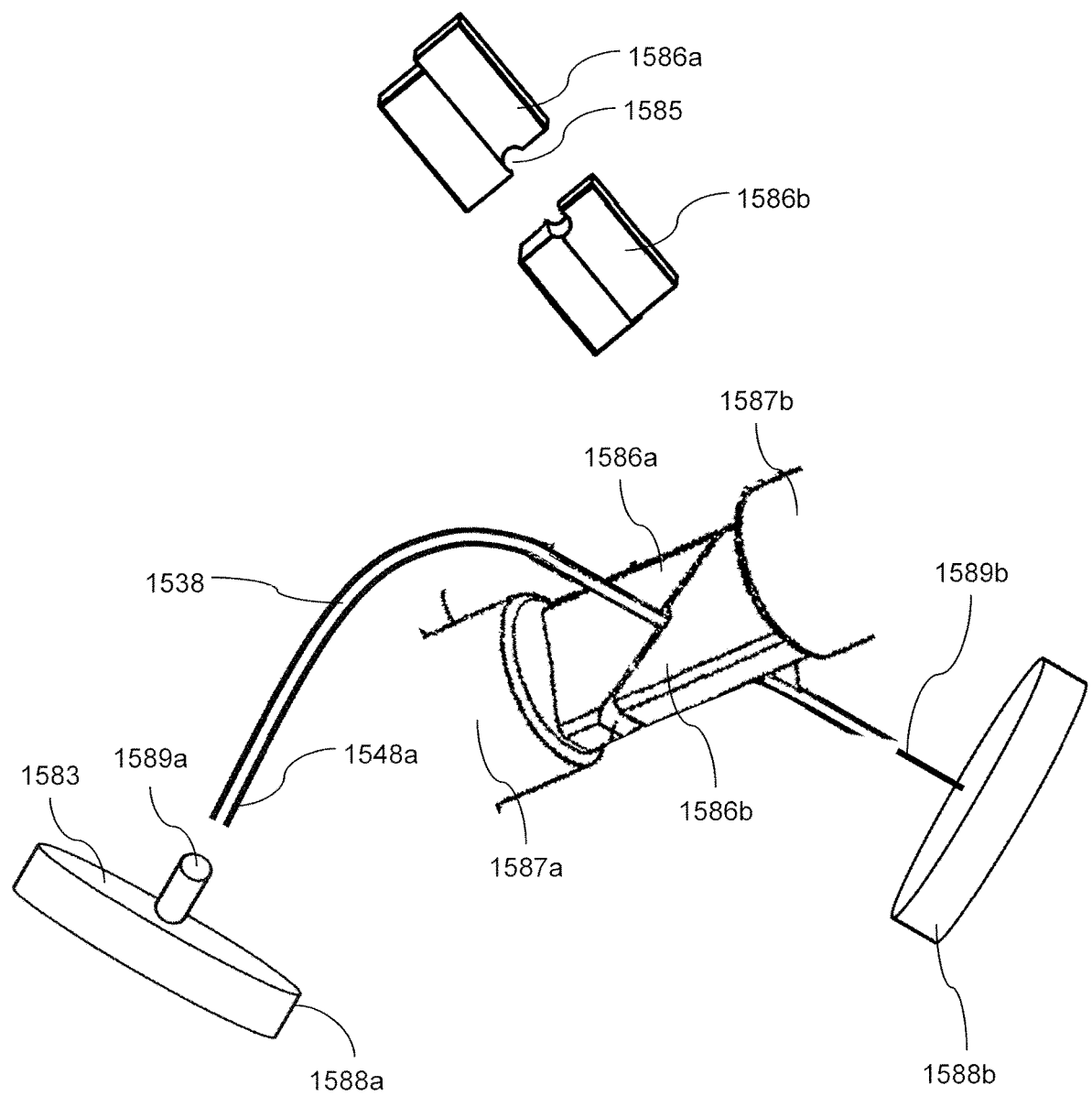
FIG. 15 is a perspective view of a molding a cartridge in accordance with an embodiment of the current invention.
Figure 16:
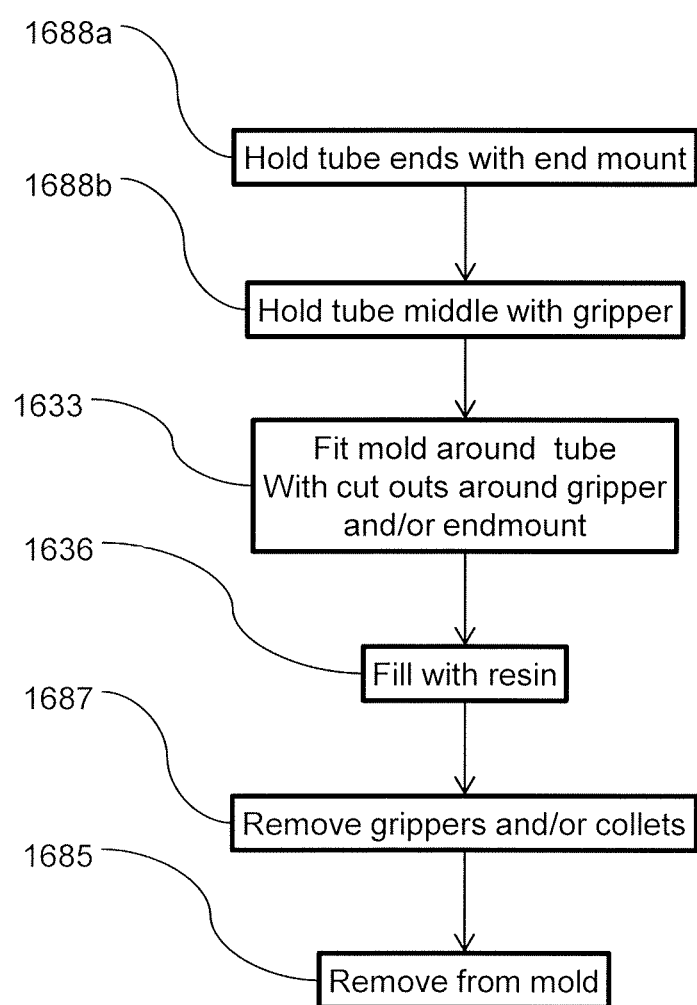
FIG. 16 is a flow chart illustrating a method of a molding system for a cartridge in accordance with an embodiment of the current invention.

Optionally a needle 752 may be supported during molding. For example, an end of the needle may be supported by an end mount. For example, an inner section of the needle may be supported by a gripper (for example as illustrated in FIGS. 15 and 16). For example, a space 756 left by a collet end mount in the molded syringe can be seen in FIGS. 17B and 19. During molding, the end mount optionally blocks the hollow portion of needle 752, for example preventing the needle from being obstructed by the molded material. Optionally, a gripper may leave a channel and/or be inserted through a channel in the overmolded material (for example channel 737).

In some embodiments, an extension may have a non-uniform cross section. For example in the center section of extension 736 windows or channels 737 are formed. Optionally holding channels 737 are formed around needle supports that hold the needle during the molding process. Optionally, the needle supports are subsequently removed, leaving behind the empty channels 737. For example, extension 736 has an I-beam cross section. Optionally ribs 735 are offset from the fluid pathway. For example, the offset is sufficient to leave space for channels 737 around fluid path 750 and/or between ribs 735. Channels 737 are optionally formed in the molded part of a syringe. For example, channels 737 may allow the needle to be held during the insert molding process.

In some embodiments, the end of extension 736 includes a mount for needle cap 704. For example, the mount may include a sealing ring 760 and/or a tapered section 761. For example, sealing ring 760 may seal against the inside of cap 704. In some embodiments, this may isolate the distal end of the extension optionally including a protruding section 751 of needle 752. For example, the cap may protect the distal end of extension 736 and/or protruding section 751 of needle 752 from contamination.

In some embodiments, a cap mount may include a tapered portion that physically holds the cap. For example, tapered portion 761 may be formed in ribs 735. In some embodiments, tapered section 761 may hold cap 704 rigidly to extension 736. Cap 704 may optionally be connected and/or disconnected from extension 736 by pulling and/or pushing cap 704 along the axis of extension 736 and/or along the axis of protruding section 751 of needle 752.

In some embodiments, a cartridge may be designed to reduce dead space. For example, a plunger may be user to drive fluid out from the reservoir. For example, the plunger may drive fluid towards a distal wall of the reservoir. Optionally fluid may pass through an opening in the distal wall to the fluid path of the extension. Optionally the plunger may be designed to initially contact the distal wall first far from opening. For example, as the plunger moves distally after first contacting the wall an increasing surface of the wall may contact the plunger. For example as the contact surface increases fluid may be driven along the distal wall towards the opening.

For example, at the end of travel of the plunger towards the distal wall of the cylinder under a force of ranging between 0-5 N and/or between 10-15 N and/or between 15-25 N the dead space between the plunger and the distal wall of the cylinder may range between 0.01 to 0.05 and/or 0.05 to 0.1 and/or between 0.1 to 0.5 ml. Optionally, the volume of the fluid path between the reservoir and the exit opening of the fluid path in a distal section of the extension may be small. For example, the internal volume of the fluid path from the reservoir to the opening of the extension may range between 0 to 0.01 and/or 0.01 to 0.03 and/or 0.03 to 0.06 and/or 0.06 to 0.1 and/or 0.1 to 0.5 ml.

FIG. 7C illustrates a proximal perspective view of a cartridge in accordance with an embodiment of the current invention. For example, a contact surface may be provided sized and/or shaped to facilitate connection to a filling machine. For example, a contact surface may include an annular surface 741. Optionally the annular surface 741 may have a width of 5 mm-20 mm For example surface 741 may facilitate connection to a vacuum device, for example for inserting a plunger into the reservoir. Alternatively or additionally, a size and shape of the cartridge may be fit for an automatic filling machine.

For example, the proximal portion of the cartridge may include gripping fittings such as a surface sized and shaped for an automated syringe holder and/or a flange 740. In some embodiments, the size of a flange and or contact surface may be non-uniform. Alternatively or additionally, a flange or gripping surface may have a uniform size and/or shape. The maximum width of the flange may range for example 5-20 mm. The minimum width of the flange may range for example 5-20 mm. Optionally, the width of the flange may be greater for a larger syringe and smaller for a smaller syringe. For example, the thickness of the flange may range 1-3 mm.

In some embodiments, a mount for a needle and/or a cap may include for example a tapered luer and/or a slip luer and/or a luer lock.

Fitting a Cartridge to a Filling Machine

Figure 8A:
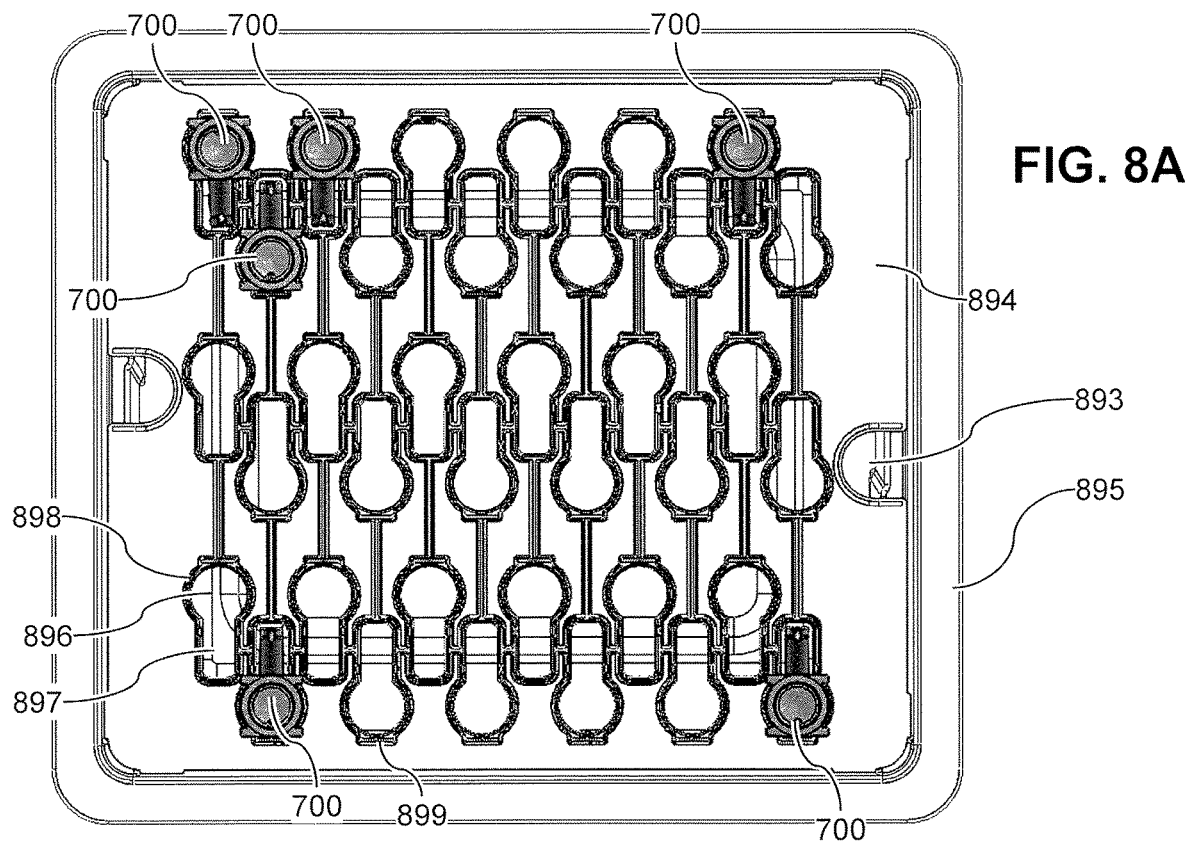
FIGS. 8A-8C are views of cartridges in a support tray that may be presented to an automated filling machine in accordance with an embodiment of the current invention.

FIG. 8A is a perspective view of a support tray for an irregularly shaped syringe in accordance with an embodiment of the current invention. For example, support tray 894 supports an angled hub syringe 700. Optionally, tray 894 includes one or more spaced-apart openings. Optionally, the openings are arranged to save space and/or fit more cartridges in the tray.

For example, the openings may be staggered and/or the orientation of the openings may alternate. In some embodiments, each opening may include an orifice 896 and/or one or more extensions 897. An opening is optionally shaped and/or sized to allow a first portion of syringe 700 to pass through the opening. The tray is optionally shaped and/or sized to support a second portion (for example a proximal flange 740) of a syringe. For example, the openings may allow a distal portion of syringe 700 to pass through while the tray supports a proximal portion of the syringe (for example a proximal flange 740). Tray 894 is optionally sized and/or shaped to fit an automated syringe-filling machine and/or to orient one or more irregular syringes 700 for filling by the automated syringe-filling machine. For example, tray 894 and/or syringes 700 may fit a standard automated syringe-filling machine.

In some embodiments, tray 894 and/or an opening therethrough may include a collar 898. Optionally, collar 898 extends upward from the face of tray 894. For example, collar 898 supports syringe 700. Alternatively or additionally, a collar may extend downwards from and/or at a non-right angle to the face of the tray. Optionally a collar may completely and/or partially surround an opening (for example opening orifice 896 and or extension 897. Optionally a collar may have a uniform and/or non-uniform height and/or thickness.

In some embodiments, openings and/or collars 898 are arranged in a series of staggered rows and/or columns. Additionally or alternatively, openings and/or collars 898 are arranged in a series of uniformly spaced rows and/or columns. Optionally, tray 894 includes cutout portions 893 for example for lifting and/or easily gripping and/or orienting tray 894 during various processing and filling operations.

In some embodiments tray 894 is positioned in a tub 895. Tub 895 optionally includes a stepped portion supporting tray 894.

Figure 8B:
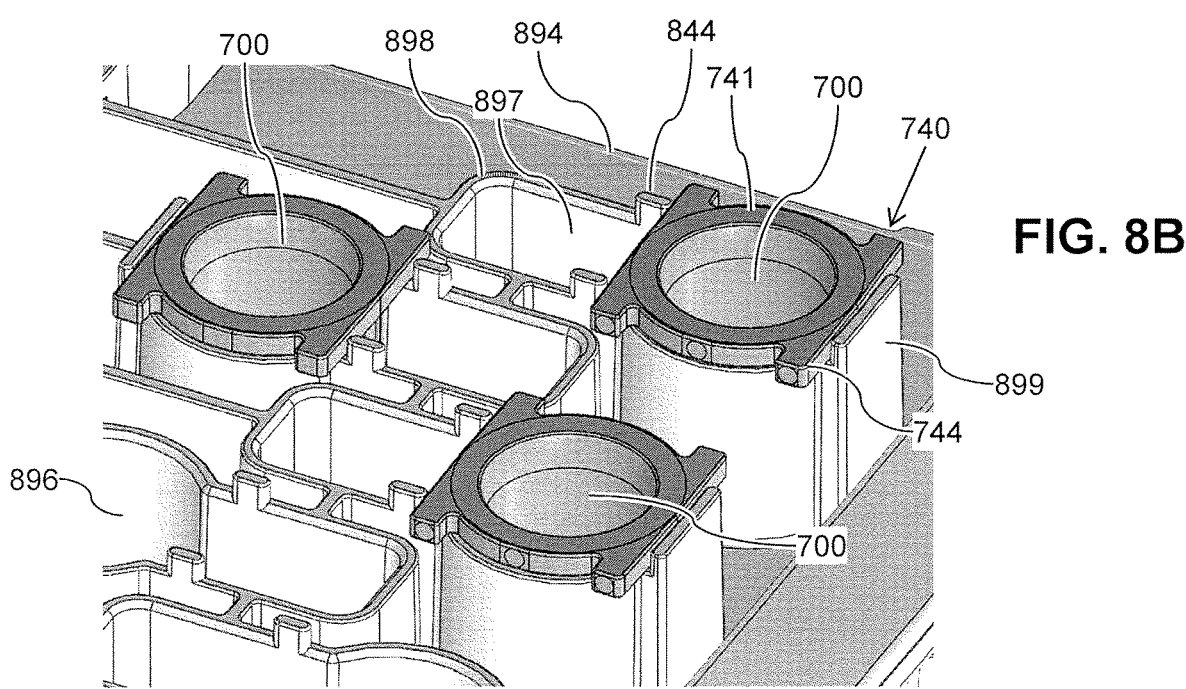

FIG. 8B is a perspective view of supporting an angled needle syringe hanging from a support tray in accordance with an embodiment of the current invention. Optionally holes in tray 894 are sized and shaped to fit a distal portion of an irregularly shaped syringe and/or allow the distal portion to fit through the hole. For example, a hole may allow a distal portion of syringe 700 to pass therethrough.

In some embodiments, extension 897 is thinner than orifice 896 and/or radiates outward from orifice 896 for example giving the hole a keyhole shape. For example orifice 896 may be sized and shaped to allow a syringe barrel to fit through the opening (for example with a tolerance of less than 0.01 mm and/or ranging between 0.01 to 0.1 mm and/or between 0.1 to 0.5 mm and/or ranging between 0.5 to 2 mm and/or more than 2 mm). For example, orifice 896 fits a barrel of syringe 700. Optionally, extension 897 is sized and shaped to allow a protruding portion of the syringe to pass through (for example with a tolerance of less than 0.01 mm and/or ranging between 0.01 to 0.1 mm and/or between 0.1 to 0.5 mm and/or ranging between 0.5 to 2 mm and/or more than 2 mm). For example, extension 897 fits the protruding portion of syringe 700. For example, extensions 897 allow a protruding portion of needle 752 and/or a needle cap, for example needle cap 704 to pass through.

In some embodiments, a collar and/or a hole may be shaped to orient the syringe and/or reservoir. For example a rear protrusion 899 on some or all of the holes of tray 894 orients barrel 742 of syringe 700 around the axis of its internal cylindrical space and/or orients a protruding portion of the syringe (for example needle cap 704). For example a front protrusion 844 on some or all of the holes of tray 894 orients barrel 742 of syringe 700 around the axis of its internal cylindrical space and/or orients a protruding portion of the syringe (for example needle cap 704). For example tray 894 orients alternating caps 704 in the opposite directions. Alternatively or additionally, syringes may be oriented in the same and/or varying directions.

In some embodiments, a collar and/or the sides of an opening in a tray may support a proximal portion of a syringe and/or cartridge. For example, collar 898 and/or the sides of holes in tray 894 may support and/or orient barrel 742 (for example, the proximal portion thereof for example a proximal flange 740 thereof). Alternatively or additionally, a tray may have other protrusions, holes and/or indentations for supporting and/or stabilizing the syringe. For example, a tray may have a pin that passes through a hole in a proximal flange of the syringe and/or a hole through which passes a pin on a proximal flange of the syringe.

An opening, hole, indentation, protrusion and/or a pin may be tapered and/or beveled. The dimensions of the tray are optionally configured so that the ends of the syringe barrels are spaced from bottom wall of tub 895. In other embodiments, the distal ends of syringes may contact the bottom wall of tub 895. Alternatively or additionally, a tray may have a hanger on its bottom side and/or a single syringe may be connected to the tray at more than one location. Alternatively or additionally, other geometries are possible within the spirit of the invention. For example, a syringe may have a needle connected to a flexible tube.

Optionally the tube and needle may be strapped to the side of the syringe and fit into a orifice and extension and/or the needle and/or tube may string back through the extension and sit on top of the tray and/or the needle and tube may string back through the extension and hang through a second hole in the tray and/or the needle and tube may string back hang from a hook on the bottom of the tray and/or the needle and tube may sit on the bottom of the tub etc.

In some embodiments, tub 895 may be enclosed in a sealed plastic bag or wrapper, for example before or after filling the syringes. In some embodiments, protective layer of sheet material, such as polyethylene, foam or other plastic, may be positioned to cover tray 894 and/or syringes. Optionally, the sheet is substantially the same size as tray 894. A closure or cover sheet optionally seals over tub 895 to completely enclose the array of syringe barrels. For example, the cover sheet may include a thermoplastic material that is heat-sealed to a flange on tub 895 to form a complete seal. For example a cover sheet may be made of a gas-permeable material such as a spun bonded polyolefin sold under the trademark TYVEK by E.I. DuPont & Co.

In some embodiments, this allows the syringe barrels to be gas sterilized, if desired, while they are in the sealed tub 895. In further embodiments, the syringe barrels can be sterilized by radiation and/or another means.

Figure 8C:
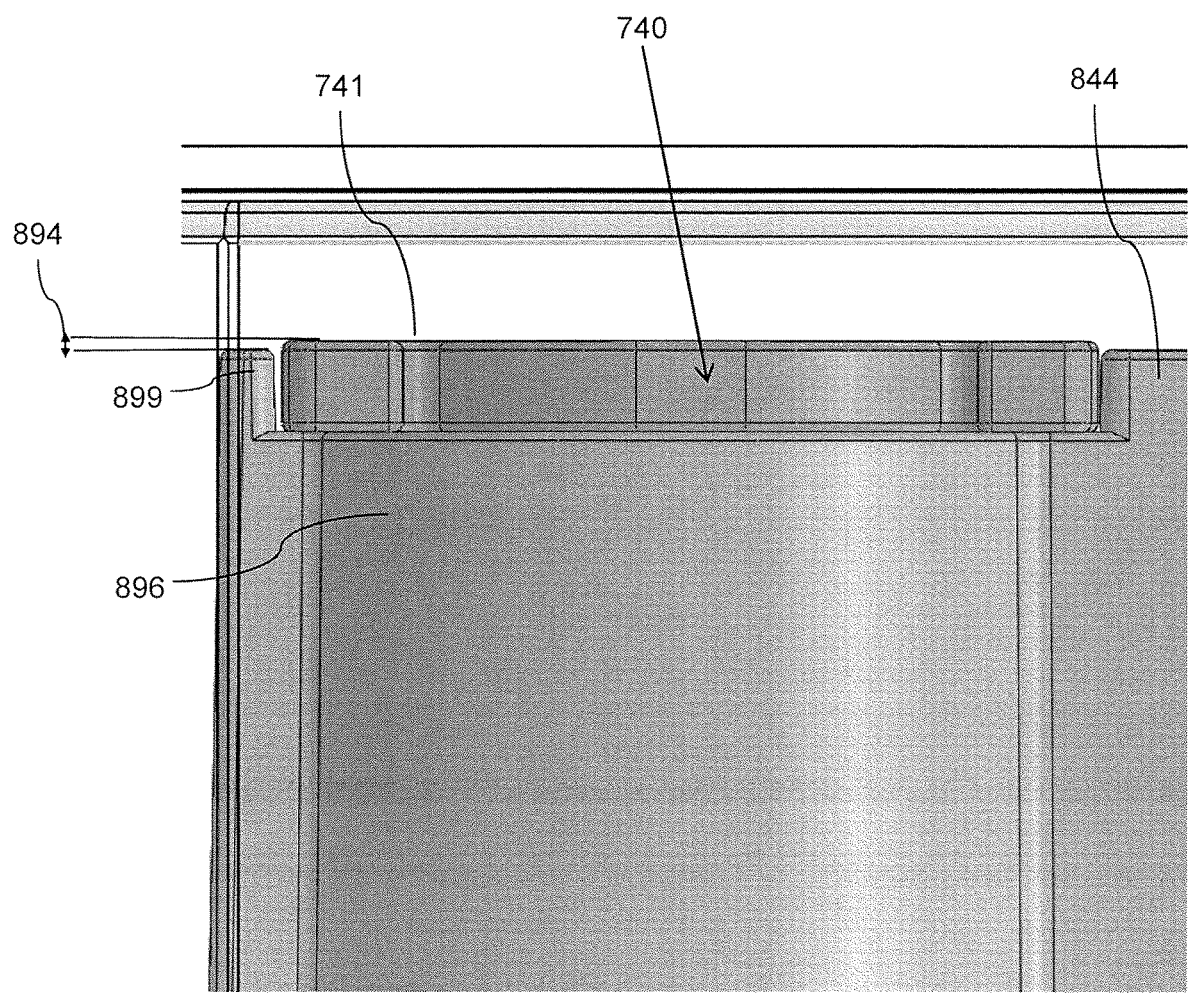

FIG. 8C illustrates a clearance for a contact surface in accordance with an embodiment of the current invention. In some embodiments, a contact surface of a syringe may clear a portion of a filling tray. For example, contact surface 741 may clear a protrusion (e.g. protrusion 899 and/or 844) of a filling tray by extending beyond the protrusion by a clearance 894. Optionally the clearance facilitates access to the proximal end of the syringe, for example by a vacuum stopper inserter. For example, clearance 894 may equal the difference between the thickness of flange 740 and the height of protrusion 844 and/or 899. Optionally, clearance 894 may range between 0.5-2 mm. For example, the thickness of flange 740 may range between 1-3 mm. For example, the height of protrusion 844 and/or 899 may range between 0.5-2 mm.

Syringe with an Angled Extension

Figure 9:
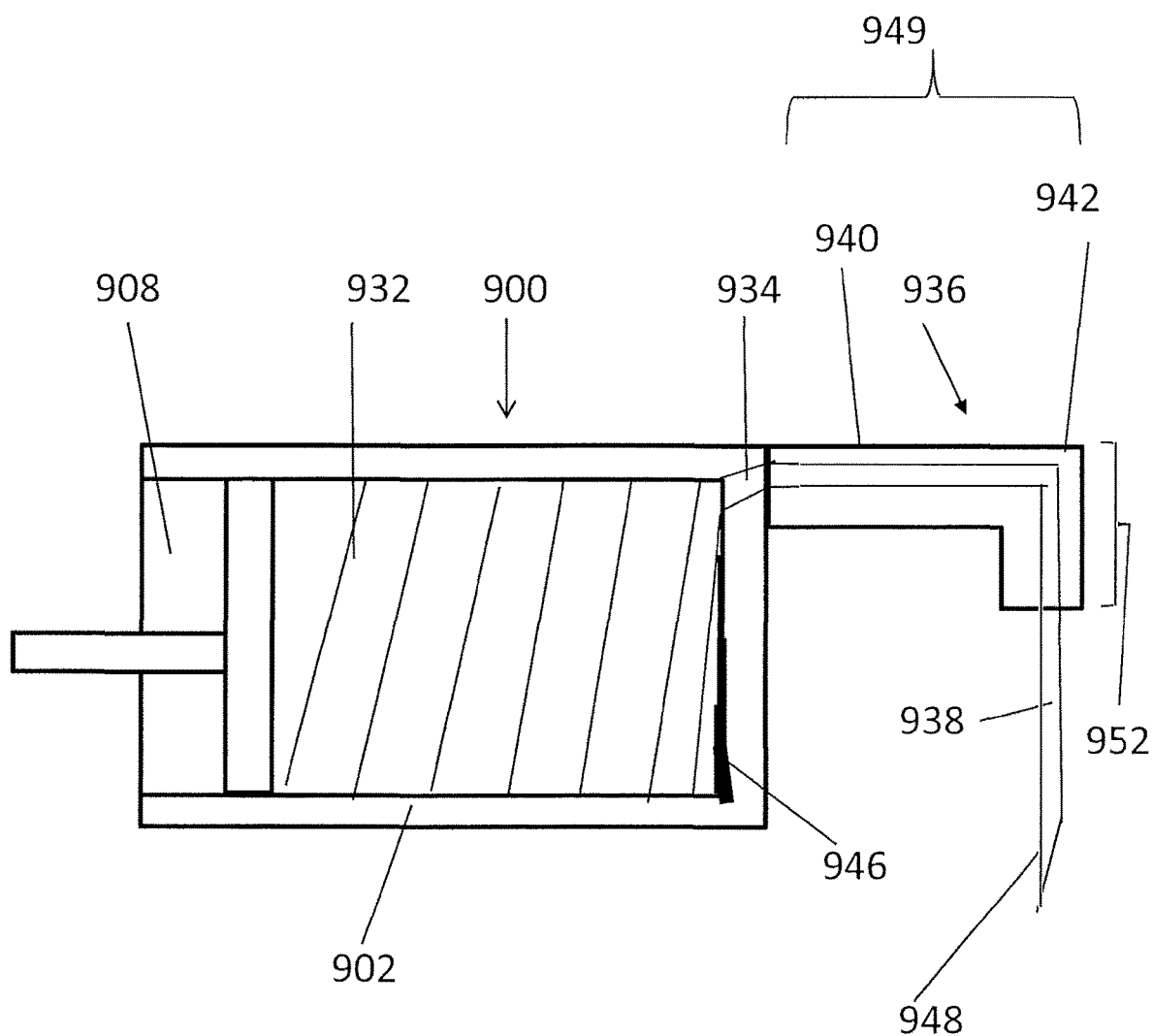
FIG. 9 is a schematic diagram of an alternative syringe with an angled extension in accordance with an embodiment of the present invention.

FIG. 9 is a block diagram of a syringe cartridge 900 with an angled extension 936 in accordance with an embodiment of the present invention. Optionally the syringe 900 may be formed by molding. For example, the syringe 900 may be molded of a polymer resin. For example, a single unitarily molded piece may include a barrel or reservoir part 902 having a cylindrical interior space 932. Extending from the barrel or reservoir part 902 is an angled extension 936, and a fluid path 934 may reach through extension 936 from cylindrical interior 932. Cylindrical interior 932 may have a proximal opening 908. Optionally extension 936 may extend from a distal end of the barrel.

Thus, syringe cartridge 900 comprises the reservoir part 902 and the extension 936 extending from the reservoir part. The extension, optionally, defines a fluid path along an interior hollow, typically through hollow interior of needle 938. In some embodiments, the extension 936 comprises a molding 940 and at least some of needle 938 extends beyond molding 940. Extension 936 optionally, turns to a finite angle with respect to the axis of the reservoir part at bend 942, and the exposed part of needle 938 is optionally at the same finite angle. Furthermore, in some embodiments, some of the needle at the finite angle—that is beyond bend 942, is enclosed within the molding 940.

The extension 936 may be molded integrally with the reservoir part 902. As an alternative, the extension 936 may be a separate molding that can be connected to the reservoir part 902.

As shown in the exemplary embodiment, the extension 936 is molded around a single length of angled needle 938. The extension 936 may be insert molded around the angled needle, for example, by inserting the needle in the mold and then injecting plastic into the mold around the needle.

In some embodiments fluid path 934 between extension 936 and cylindrical interior 932 may be bent. Optionally fluid path 934 may include a needle. For example, a hollow metal needle may be insert molded into the syringe. Optionally one end of the embedded needle may project out of the extension. For example, the projecting end of the embedded needle may have a sharpened tip. Optionally the projecting end of the embedded needle may be substantially straight. Alternatively or additionally, the projecting end of the embedded needle may be bent, curved and/or angled.

The molding 940 of the extension 936 may include a neck part 949 that is parallel with the axis of the reservoir part and/or bend 942. Molding 940 optionally includes a further length 952 of molding that goes beyond bend 942. For example, further length 952 may be angled with respect to the axis of the reservoir part.

Figure 10:
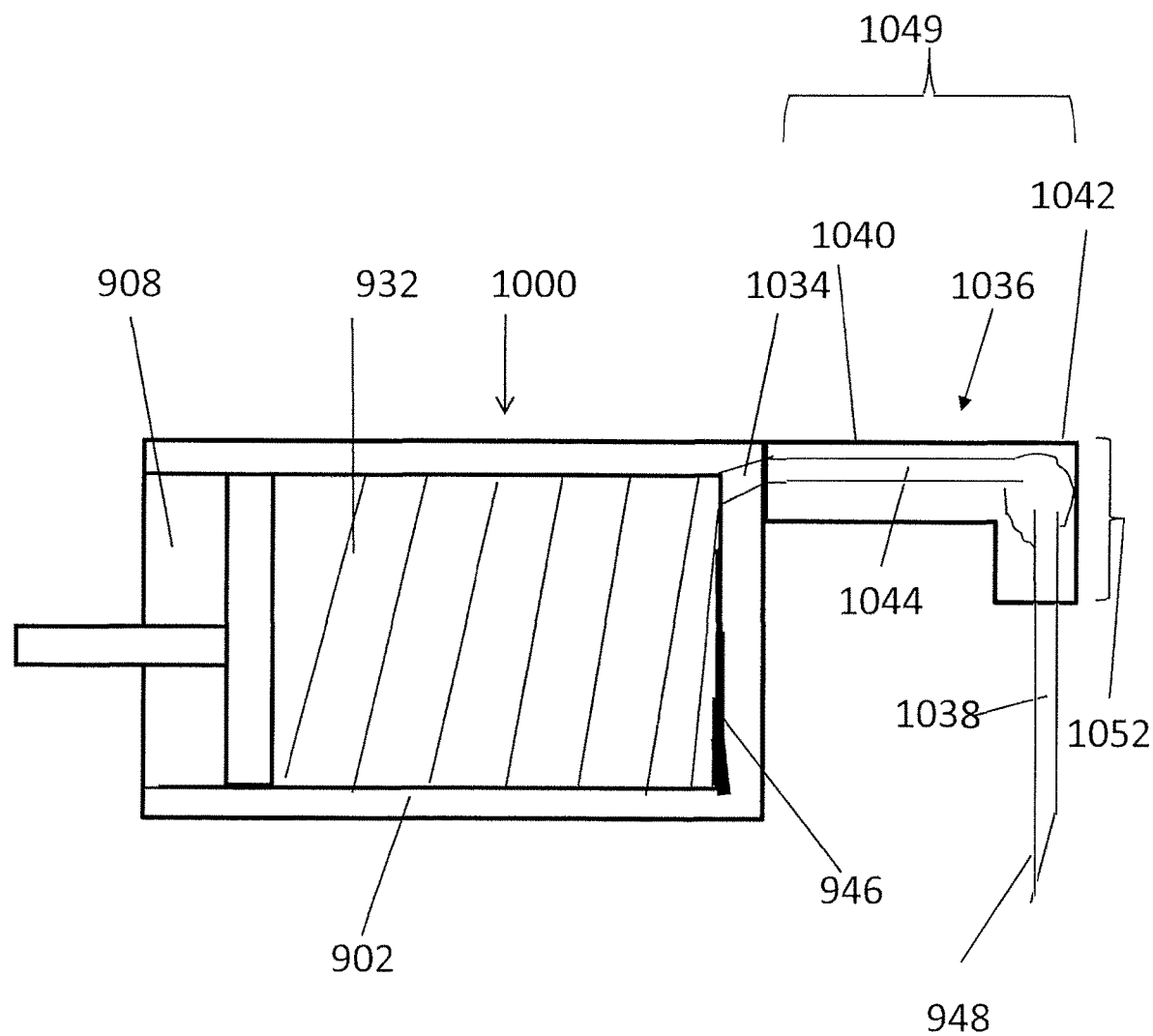
FIG. 10 is a schematic diagram of an alternative syringe with an angled extension in accordance with an embodiment of the present invention.

Reference is now made to FIG. 10, which shows an alternative construction of the extension 1036 of a syringe 1000. Parts that are the same as in FIG. 9 are given the same reference numerals and are not described again except as needed for an understanding of the present embodiment. The fluid path 1034 comprises a second needle or tube 1044 parallel to the axis of the reservoir part. The second tube 1044 is connected to a first needle 1038 being at the finite angle. For example, the junction between tube 1044 and needle 1038 may occur at bend 1042.

As shown for example in FIGS. 9 and 10, extension 936 and/or 1036 may be connected to the reservoir part 902 radially away from the central axis of the reservoir part 902, that is to say eccentrically. While this is not essential, it provides the exposed needle with an extra few millimeters along the diameter of the reservoir part so as to be long enough to accept a standard needle cover without excessively protruding from the profile of the barrel of the cartridge.

With the eccentric connection, the finite angle is optionally selected in a plane that crosses the axis of the barrel of the syringe. For example, the fluid path crosses an extension of the axis of the reservoir part, so that the needle crosses the diameter of the barrel and injects the user at a side of the cartridge diametrically opposite to the exit of the extension from the reservoir part.

A base wall 946 of the cartridge reservoir part 902, which is the wall from which the extension exits, may be angled towards the extension, to help drain fluid fully into the fluid path 934.

Tip 948 of the exposed part of needle 938 may be beveled, and the beveling may be in a direction towards the reservoir part 902 of the cartridge 900.

The molding 1040 of the extension 1036 may include a neck part 1049 that is parallel with the axis of the reservoir part, bend 1042 and/or a further length 1052 of molding that goes beyond bend 1042.

The extension 936 and/or 1036, when viewed end on, may have an "I" shaped profile. The "I" shaped profile is shown for example in perspective in FIG. 7A, which will be referred to hereinbelow. Alternatively or additionally, it may have a "T" shaped profile and/or a cross-shaped profile and/or another shaped profile.

Regarding the finite angle, in general a convenient angle is a right angle so that the cartridge may be placed against the skin and then the injection may be carried out under the skin. However, not all parts of the body allow for a sufficient area of skin. For example, dental injections may demand different angles of the needle as the dentist attempt to follow the angles of the gum. The bend in extension 936 and/or 1036 may thus oriented at an angle between 30 and 150 and/or between 10 and 140 degrees and/or between 60 and 120 degrees and/or between 85 and 95 degrees of the axis of the barrel of the reservoir, and in particular at a right angle.

In some embodiments, a needle protruding from an extension may be rigidly mounted to the extension. Optionally, a protruding portion of the needle may be straight and/or the axis of the needle may be oriented in the same direction as distal portion (e.g. portion 952 and/or 1052) of the extension. Optionally a needle cap may be rigidly mounted to the extension. The needle cap may be straight and/or the axis of the needle cap may be oriented in the same direction as the extension (for example a distal portion thereof). As discussed, the mount may fit a standard needle cap. For example, the mount may be configured to seal to the needle cap protecting the needle from contamination and/or protecting the sterility of the needle.

Alternatively or additionally, a needle and/or a needle cap may be directed at an angle to the extension and/or may be partially or completely mounted on a portion of the syringe not included in the extension.

In some embodiments, the syringe may be configured for automatic filling. For example the syringe may be sized and shaped to fit a standard and/or minimally modified filling machine, for example a standard filling machine with a custom syringe support tray. For example, the syringe may have a proximal flange for supporting the syringe on the support tray or for gripping by a robot arm. The flange may be round and/or may have non-circular features. Optionally the non-circular features may fit the support tray and/or determine the orientation of the syringe on the support tray. When the syringe is supported on the support tray, proximal opening 908 may be facing upward.

Figure 11:
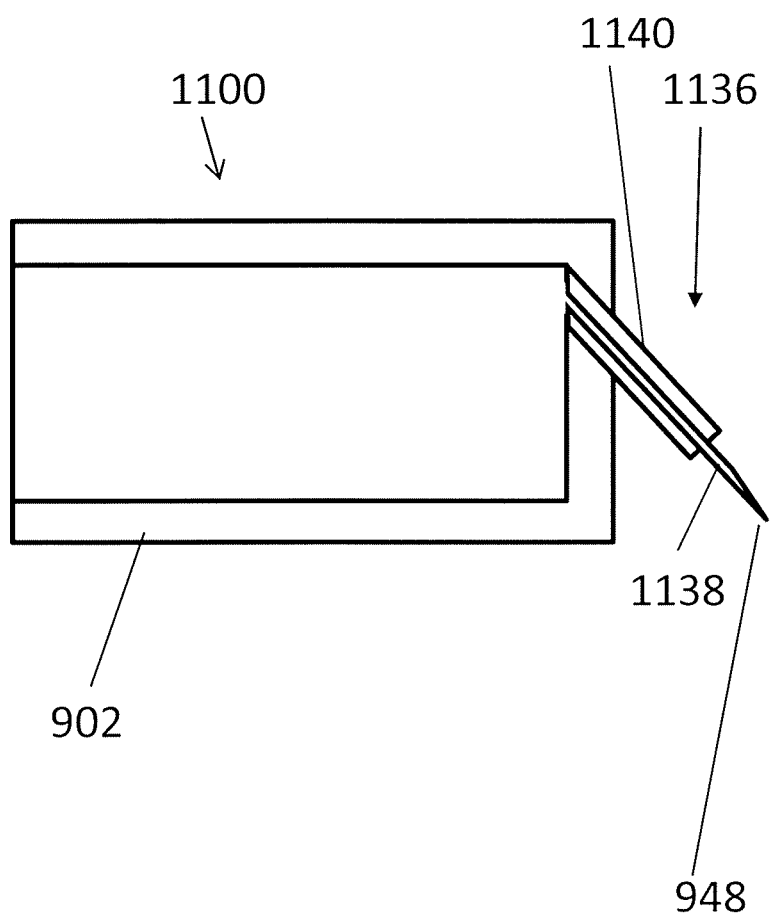
FIG. 11 is a schematic diagram of an alternative syringe with an angled extension in accordance with an embodiment of the present invention.

FIG. 11 illustrates a syringe 1100 with a straight extension 1136 at an angle to a reservoir part 902 in accordance with an embodiment of the invention. For example, straight extension 1136 may include a molded part 1140. Optionally, a straight needle 1138 is insertion molded into molded portion 1140. For example, extension 1136 may include a mount for a needle cap.

Figure 12:
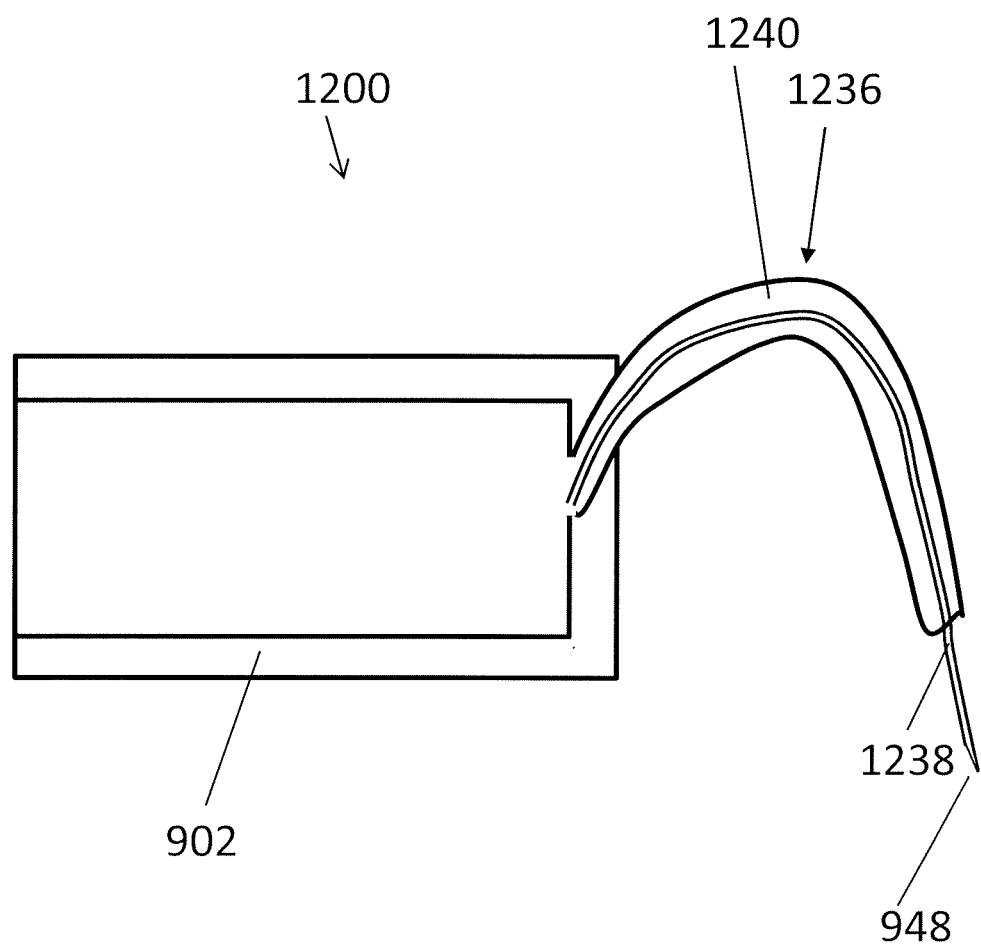
FIG. 12 is a schematic diagram of an alternative syringe with an angled extension in accordance with an embodiment of the present invention.

FIG. 12 illustrates a syringe 1200 with a curved extension 1236 at an angle to a reservoir part 902 in accordance with an embodiment of the current invention. For example, curved extension may include a molded part 1240. Optionally, a curved needle 1238 is insert molded into molded portion 1240. For example, extension 1236 may include a mount for a needle cap.

In some embodiments, an extension may protrude on over beyond more than one boundary of a reservoir in accordance with an embodiment of the current invention. For example extension 1236 extends upward (dorsally) beyond the dorsal limit of reservoir 902 and also downward (ventrally) below the ventral limit of reservoir 902. For example, having an extension protrude on opposing sides of the reservoir may balance a syringe and/or reduce the amount that the extension protrudes on one or the other side.

Figure 13A:
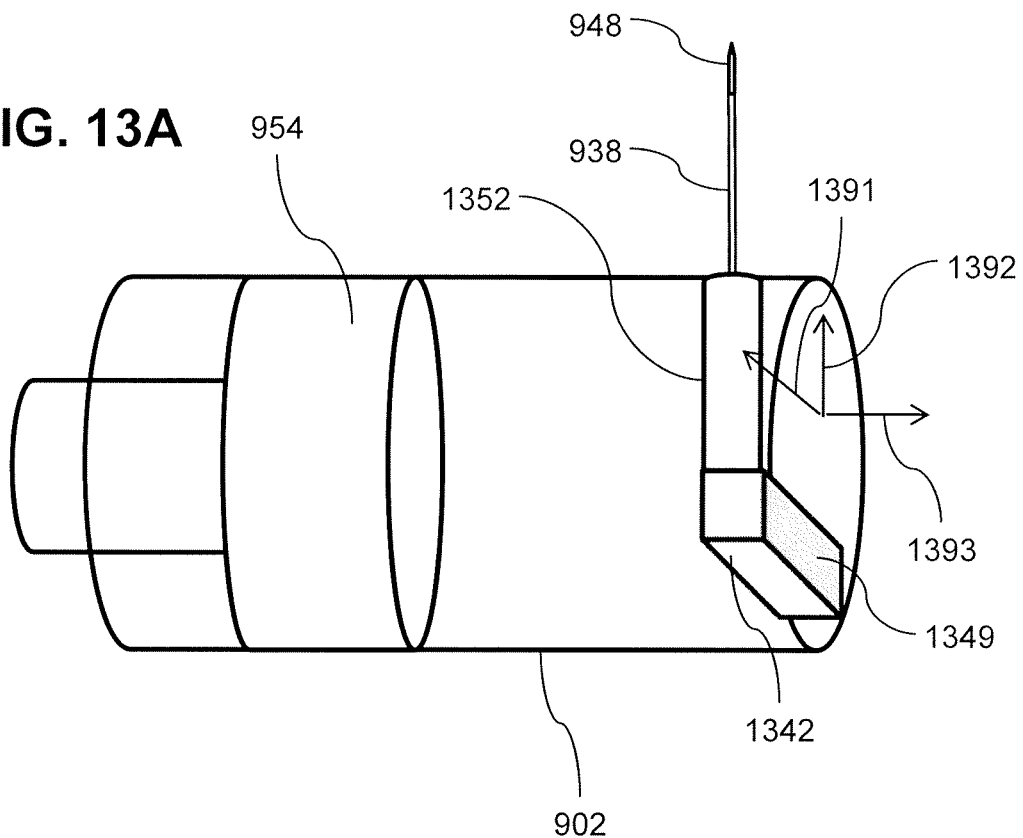
FIGS. 13A-13B are a schematic diagram of an alternative syringe with an angled extension in accordance with an embodiment of the present invention.
Figure 13B:
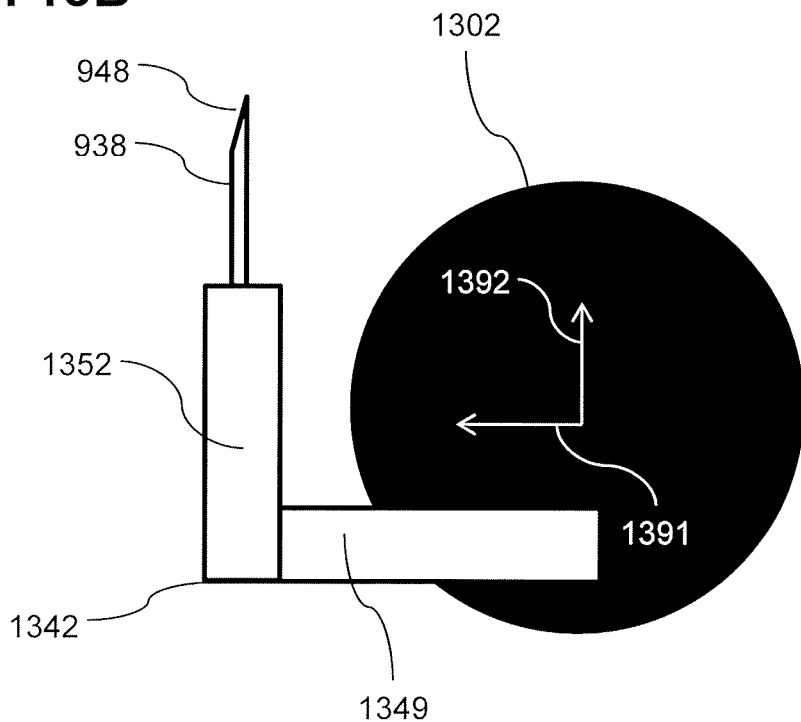

FIGS. 13A and 13B illustrate an extension that extends and bends beyond a lateral edge of a reservoir in accordance with an embodiment of the current invention. For example, an extension may include a portion that extends in a lateral direction outward and/or a section that returns toward the longitudinal axis of the reservoir. For example, an extension may have a bend 1342 and/or have an angle outside a transverse Silhouette of the reservoir. For example, a needle and/or a cap mount may be oriented along a line that does not intersect a transverse Silhouette of the reservoir.

In some embodiments, an extension extends and/or bends outside an edge and/or transverse silhouette of a reservoir. For example, an inner (proximal) portion 1349 of an extension may extend laterally outward (for example in and/or at an acute angle to a lateral direction 1391) from a transverse silhouette 1302 of a reservoir 902. An outer (distal) portion 1352 may return back, for example towards the longitudinal axis 1393 of the reservoir and/or towards a median direction 1392 of the reservoir and/or parallel to a median direction 1392 and/or towards the azimuthal direction in a radial coordinate system having the longitudinal axis 1393 of the reservoir as its height axis.

In some embodiments, a times bent needle may be used to generate another dimension flexibility. For example, in the exemplary embodiment of FIG. 13A, needle 938 may be inserted to the user by rotating the cartridge around longitudinal axis 1393.

Stabilizing a Tube During Insert Molding

Figure 14:
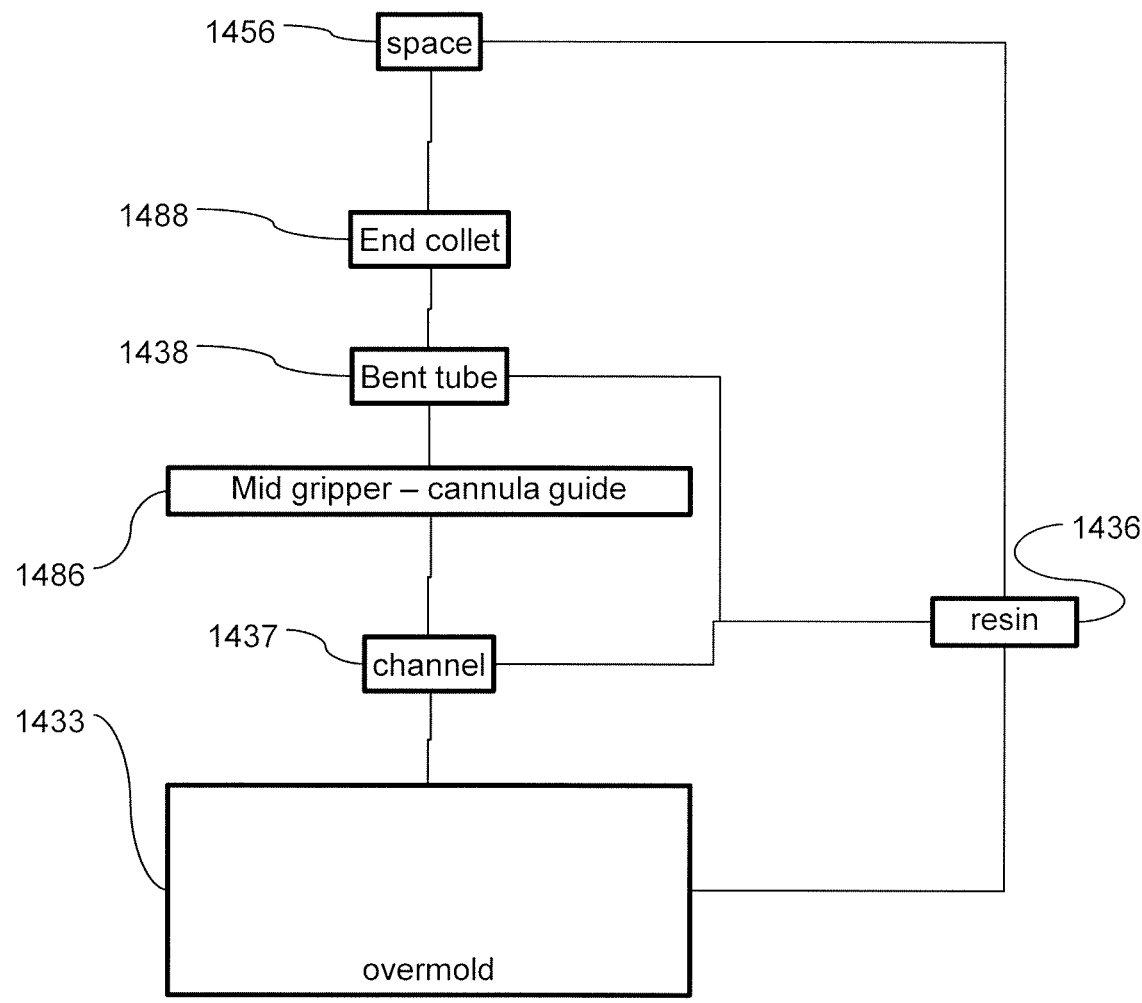
FIG. 14 is a block diagram of a molding system for a cartridge in accordance with an embodiment of the current invention.

FIG. 14 is a block diagram illustrating a system for stabilizing a tube. Optionally, during insert molding a tube will be held in place by an end mount and/or a gripper. For example and end mount may hold an end of the tube. For example, a gripper may hold a non-terminal section of the tube. Optionally, an end mount may prevent molding material from entering and/or clogging the tube.

In some embodiments, a bent tube 1438 may be held at three or more points during insert molding. For example, bent tube 1438 may be insert molded into a molded extension of a syringe. Optionally, the tube will be stabilized by holding it. For example, tube 1438 may be held at one or both ends by collets 1488. Additionally and/or alternatively, tube 1438 may be held at one or more interior sections by a gripper 1486.

For example, a gripper may include two parts that guide and/or grasp the tube. For example the two parts may be mounted to move between an engaged position where gripping surfaces of the two parts press against the tube from opposing sides and a disengaged position in which at least one of the grippers is distanced from the tube. Alternatively or additionally, a gripper may include a guide space that at least partially surrounds a tube and/or limits movement of the section of the tube in at least one direction. An end mount optionally includes a collet and/or a cavity shaped to fit an end of the tube, for example fitting snugly around the end of the tube to inhibit lateral and/or longitudinal movement of the end of the tube with respect to its axis.

Alternatively or additionally an end mount may include a pin that is inserted into a hollow of the end of the tube. In some embodiments, the pin fits snugly into the hollow to inhibit lateral and/or longitudinal movement of the end of the tube with respect to its axis. For example, the pin may be tapered.

In some embodiments, a tube may be held at a section which is within the molded area and/or surrounded by molded material. For example, a gripper and/or end mount may access the tube through a channel and/or a space during molding. Optionally, mold 1433 may include a channel 1437 and/or a space 1456 fitting gripper 1486 and/or end mount 1488. In some embodiments, a gripper and/or end mount may take up space inside the mold. The mold 1433 can be filled with resin 1436. After the resin hardens, the gripper and/or end mount is optionally removed leaving, for example a channel (for example channel 1437) and/or a space (for example space 1456).

FIG. 15 is a perspective illustration of a bent tube, an end mount and a gripper in accordance with an embodiment of the current invention.

In some embodiments a gripper may include two parts (for example grippers 1586a and 1586b). Grippers 1586a and/or 1586b may be mounted to move together and/or independently to grasp a tube. For example, a gripper 1586a and/or 1586b may be mounted on an actuator (for example actuator 1587a and/or 1587b). Actuators 1587a and 1587b optionally are controllable to push grippers 1586a and 1586b together (for example to grasp a tube 1538 for example as illustrated in FIG. 15) and/or to pull grippers 1586a and 1586b apart (for example to release a tube 1538). Optionally, a gripper may include a shape fitting and/or a guide for a tube for example a cut out 1585.

In some embodiments an end mount may include a holder for an end of a tube. For example an end mount 1588a may include a hollow 1589a that fits around an end 1548a of a tube. Alternatively or additionally, an end mount 1588b may include a pin 1589b that fits into a hollow of tube. Optionally the pin may be beveled and/or inserted into tightly enough into the tube to prevent material from leaking into the tube during molding. Alternatively or additionally, and end mount may include a contact surface. For example a contact surface 1583 may be at right angles to an axis of a pin and/or a hollow 1589a for example to fit a flat end 1548a of tube 1538.

FIG. 16 is a flow chart illustration of a method of insert molding a tube into a syringe. Optionally the tube is held 1688a, 1688b in place with one or more holders (for example an end mount and/or a gripper). For example a mold is fit 1633 around the holders and filled 1636 with resin. Optionally the interior of the mold has the form of a syringe. Optionally the mold has channels through which the holders protrude. Optionally the resin is allowed to harden and then the holders are removed 1687 and/or the mold is removed 1685. The resin and tube optionally form a syringe with an embedded tube and/or channels and/or hollows where the holders were located.

Further Syringe Details and Alternatives

Figure 17A:
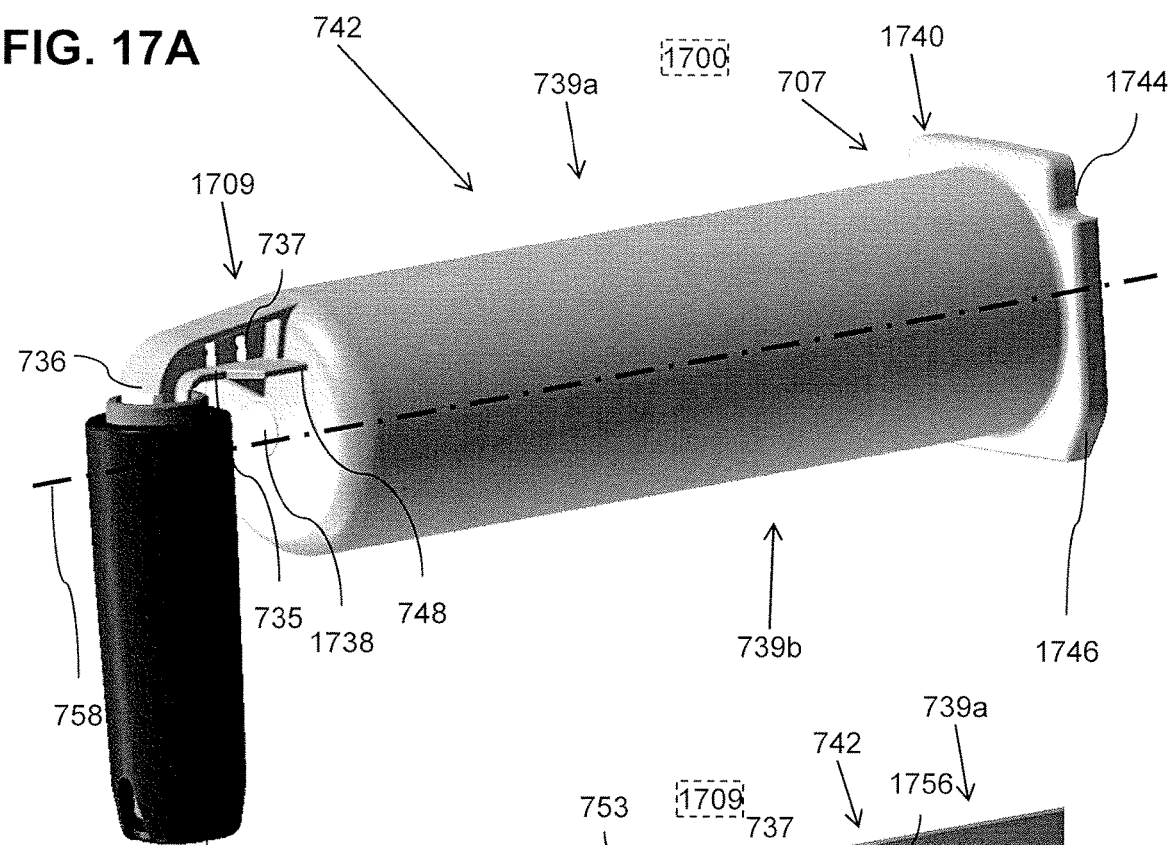
FIGS. 17A-17B are perspective views of an alternate syringe with an angled extension mounted off center in accordance with an embodiment of the present invention.
Figure 17B:
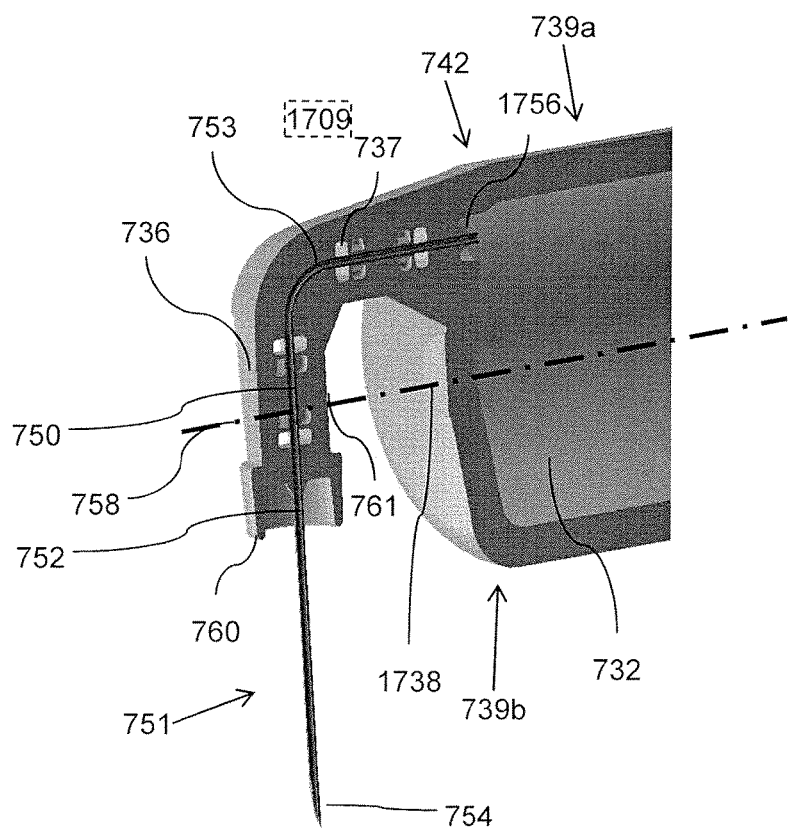

FIGS. 17A and 17B are perspective and cross sectional views respectively of a cartridge in accordance with an embodiment of the current invention.

In some embodiment, an indentation and/or a protuberance may be used to position syringe 1700 in a delivery device. For example, indentation 1738 is conical and may interact with a protuberance and/or indentation in the delivery device to position the distal end 1709 of the cartridge into alignment with the delivery device. For example, an indentation and/or protuberance could include a pin and/or a matching hole. In some embodiments, a bevel and/or a cut out may optionally interact with a complementary part in a delivery device (for example clips and/or snaps in the delivery device). For example a flange 1740 may include a bevel 1746 and and/or cutout 1744 and/or tab 748. For example, a conical and/or cylindrical pin may fit into a conical hole such that as the pin is inserted itself aligns.

In some embodiments, the size of the end mount holding the end of needle 752 in cavity 732 is made small to reduce the dead space 1756 left over after molding. Optionally, an end mount may include a pin and/or a collet. For example, a collet may have a concave and/or conical inner face that grasps the end of needle 752. Alternatively or additionally, a pin may have a convex and/or conical face that fits into the hollow of needle 752 and/or is self-aligning as it is inserted. For example, a pin may include an inner convex portion that fits into the needle 752 and/or an outer concave portion that positions needle 752. Before molding, the outer concave portion of the pin may position needle 752 in order to insert the inner convex portion of the pin into the hollow of needle 752. Then the outer concave portion may be retracted before molding. Optionally during molding only the inner portion of the pin remains in the mold. After molding the inner pin is optionally removed leaving a reduced dead space when a drug is discharged from the syringe.

FIGS. 18A and 18B are schematic cross-sectional views of a syringe 1800, which includes a reservoir for a drug delivery device and/or has an angled extension in accordance with an embodiment of the present invention. Optionally, syringe 1800 1836 has a fluid path passing through a bent arm center mounted on a cylindrical cavity 1832 of a barrel 1842. Optionally the bent arm is molded and/or formed in one piece with barrel 1842. For example, a fluid path 1850 between internal cavity 1832 and extension 1836 makes an approximately 90 degree bend such that extension 1836 is directed towards the ventral side 739b of barrel 1842. Barrel 1842 optionally includes a proximal flange 1840.

In some embodiments barrel 1842 may have a length 1870a ranging for example between 70 to 180 mm. In some embodiments an internal cylindrical space 1832 of a barrel 1842 may have an average width 1870b ranging for example between 10 to 15 mm. Optionally, a reservoir may have a circular cross section such that width 1870b is the diameter of the circle. In some embodiments extension 1836 may have a straight end portion with a length 1870c ranging for example between 6 and 9 mm. In some embodiments straight portion 1851 of a needle 1852 extending out of an extension 1836 may have a length 1870d ranging for example between 5 and 7 mm. In some embodiments extension 1836 may have sealing ring 760 for a needle cap.

Sealing ring 760 may have a length 1870e ranging for example between 1 to 3 mm. In some embodiments sealing ring 760 may have an internal cavity with a length 1870i ranging for example between 0.2 and 0.6 mm and/or between 0.6 and 1.5 mm and/or between 1.5 and 2.5 mm. In some embodiments sealing ring 760 may have an external average width 1870f which also may be an average outer diameter ranging for example between 0.5 to 2 mm and/or 2 to 5 mm and/or between 5 to 7 and/or 7 to 15 mm. In some embodiments sealing ring 760 may have an internal average width 1870g which may also be an average inner diameter ranging for example between 0.3 to 2 mm and/or 2 to 5 mm and/or between 5 to 7 and/or 7 to 14 mm.

In some embodiments, an extension 1836 may have a neck with an average width not including sealing ring 760 indicated by 1870h which may range for example between 0.5 to 2 mm and/or 2 to 5 mm and/or between 5 to 7 and/or 7 to 15 mm. Optionally the neck may have a non-uniform cross section, for example, an I beam or cross-shaped cross section or a tapered cross section. For a non-uniform cross section, an average outer width may be defined as the width of the smallest oval that can enclose the neck averaged over the length of the neck. Alternatively the same dimensions may apply to a syringe with an off center mounted fluid path for example as in the embodiments of FIGS. 7A-7C, 17A-17B and 19.

Plunger with Reduced Dead Space

FIG. 16 is a cross-sectional view of a distal section 1909 of a syringe in accordance with an embodiment of the present invention. Optionally, a syringe includes an angled inner distal wall 1978 and/or an angled extension 736 mounted off center on a cylindrical cavity 732. For example, the fluid path may connect to cavity 732 of barrel 742 at an off centered space 756.

In some embodiments, a distal face of a plunger seal 1970 may have a convex substantially conical shape with an opening angle 1968. In some embodiments, an inner distal wall 1978 of a cylindrical cavity 732 may have a substantially concave conical shape with an opening angle 1966. Optionally opening angle 1968 of the distal face of plunger seal may be sharper than opening angle 1966 of the inner distal wall 1978 of cylindrical cavity 732. For example, the difference in angles may range between 0 to 0.5 degrees and/or between 0.5 to 1 degree and/or between 1 to 5 degrees and/or between 5 to 15 degrees.

Optionally plunger seal 1970 is deformable (for example elastic) such that as it is pushed against wall 1978 it takes that shape of wall 1978 pushing fluid from the center towards the edges. Optionally inner distal wall 1978 of a cylindrical cavity 732 may be angled with respect to the distal face plunger seal 1970. For example, wall 1978 space 756 may be inclined away from plunger seal 1970 such that as plunger seal 1970 is pushed progressively towards wall 1978, seal 1970 progressively contacts more of wall 1978, progressively pushing fluid towards space 756. In order to better show molded features, an optional needle 752 forming a boundary of fluid path 750 is not shown in FIG. 19.

In some embodiments, features may be configured to avoid fluid getting trapped in dead space between the distal face plunger seal 1970 and the inner distal wall 1978 of cylindrical cavity 732. For example, the shape of the distal face of plunger seal 1970 and/or the distal inner wall of cavity 732 may be configured to push fluid towards the opening of fluid path 750 as plunger seal 1970 approaches the inner distal wall of cavity 732. For example in some embodiments, where the fluid path 750 connects to cavity 732 near an outer edge of cavity 732, opening angle 1968 of the distal face of plunger seal may be sharper than opening angle 1966 of the inner distal wall 1978 of cylindrical cavity 732.

Figure 19:
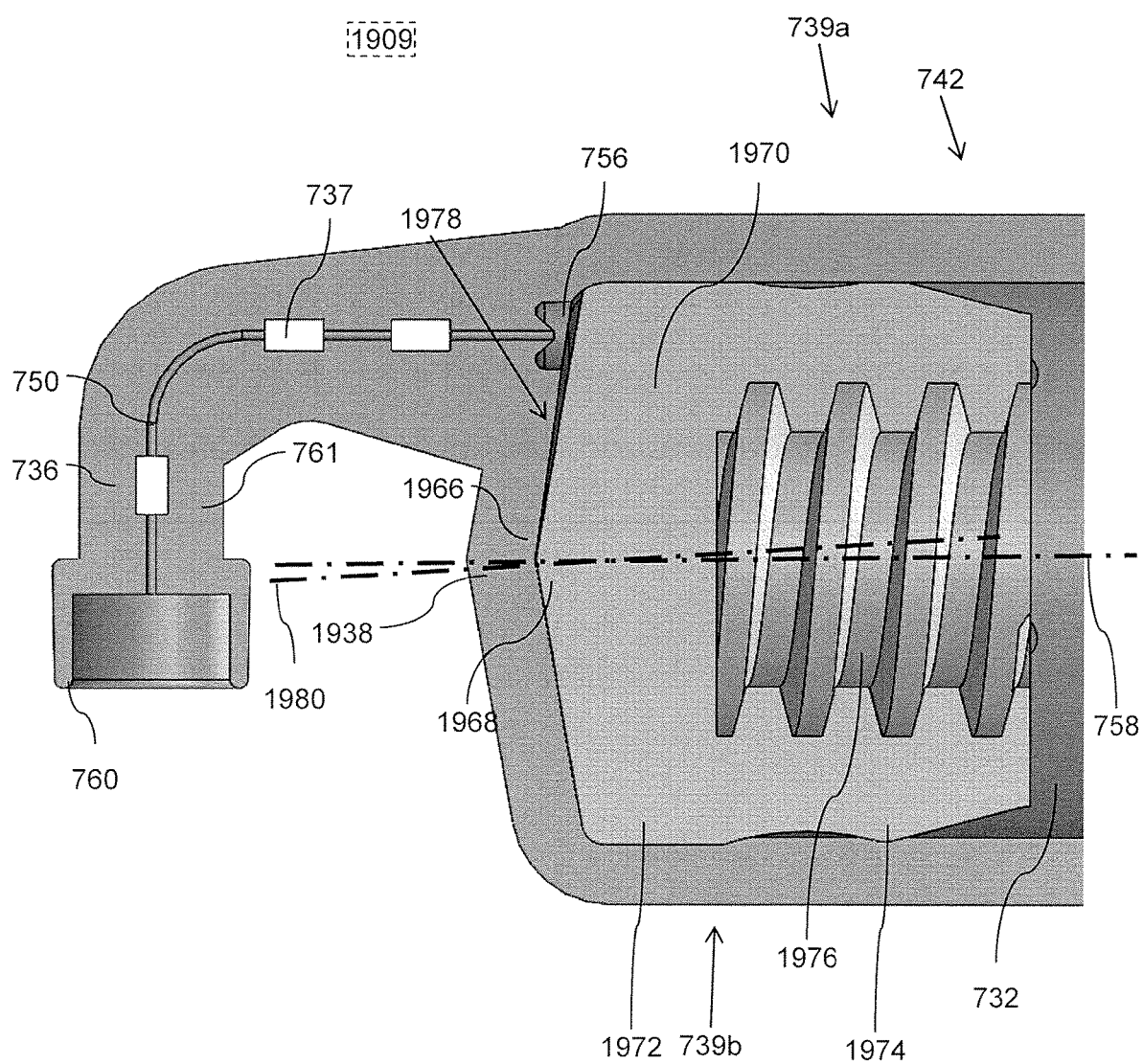
FIG. 19 is perspective views of a distal portion of an alternate syringe with an angled extension mounted off center in accordance with an embodiment of the present invention.

For example the opening angle of the distal face of plunger seal 1970 may range between 0 to 1 degree less and/or between 1 to 3 degree less and/or between 1 to 5 degree less and/or between 5 to 10 degree less and/or between 10 to 30 degree less than the opening angle of distal wall 1978 of cavity 732. Alternatively or additionally, in some embodiments, where the fluid path 750 connects to cavity 732 near the axis 758 of cavity 732 (for example as illustrated in FIG. 19), opening angle 1968 of the distal face of plunger seal may be less sharp than opening angle 1966 of the inner distal wall 1978 of cylindrical cavity 732.

In some embodiments, where the fluid path 750 connects to cavity 732 near an outer edge of cavity 732, the inner distal wall 1978 of a cylindrical cavity 732 connecting to fluid path 750 may be angled away from the distal face plunger seal 1970. For example, plunger seal 1970 and/or the distal face thereof may be aligned with axis 758 of cylindrical cavity 732 while an axis 1980 of the conical distal inner wall 1978 is at an angle of between 0 to 0.1 degree and/or between 0.1 to 1 degree and/or between 1 to 3 degrees and/or between 3 to 10 degrees and/or between 10 to 30 degrees of axis 758 and/or an axis of plunger seal 1970 and/or an axis of a conical face of plunger seal 1970.

Alternatively or additionally distal inner wall 1978 may not be right conical and/or or may not be conical and/or may not be symmetrical. For example, fluid path 750 may connect to inner distal wall 1978 between the center and the outer edge and/or the portion of inner distal wall 1978 connecting to path 750 may be indented slightly distally with respect to the rest of inner distal wall 1978. For example, in some embodiment fluid path 750 may connect near the dorsal side 739a of cavity 732. In such a case, the axis of inner distal wall 1978 may optionally be tipped at a positive angle with respect to axis 758 and/or an axis of a conical face of plunger seal 1970.

In some embodiments, when inserted into cavity 732, plunger seal 1970 may be substantially symmetric around axis 758. For example, plunger seal 1970 may have a sealing surface 1972 and/or a stabilizing surface 1974 in contact with the inner side walls of cavity 732. Optionally, plunger seal 1970 may include a plunger driver mount 1976. Plunger driver mount 1976 is optionally coaxial to cavity 732.

In an alternative embodiment, for an off center fluid path, the distal face of a plunger seal 1970 may have a concave substantially conical shape, and an inner distal wall 1978 of a cylindrical cavity 732 may have a substantially convex conical shape. Optionally in the alternative case, the opening angle of the distal face of plunger seal may be less sharp than opening angle of the inner distal wall 1978 of cylindrical cavity 732.

In an alternative embodiment, for an off center fluid path, the distal face of a plunger seal 1970 may have a concave substantially conical shape, and an inner distal wall 1978 of a cylindrical cavity 732 may have a substantially convex conical shape. Optionally in the alternative case, the opening angle of the distal face of plunger seal may be less sharp than opening angle of the inner distal wall 1978 of cylindrical cavity 732.

In some embodiments, an indentation and/or a protuberance may be used to position syringe 1700 in a delivery device. For example, protuberance 1938 is conical and may interact with a protuberance and/or indentation in the delivery device to position the distal end 1709 of the cartridge into alignment with the delivery device. For example, an indentation and/or protuberance could include a pin and/or a matching hole.

Exemplary Dimensions of a Drug Delivery Device

In some embodiments the payload of a reservoir (for example a syringe) may include, for example between 0.5 and 2 ml and/or between 2 and 7 ml and/or between 7 and 6 ml and/or between 7 and 10 ml of a drug and/or more. In some embodiments, the injector may discharge the entire payload as a single dose. A drug delivery device may include, for example, a patch injector, and/or an internally powered driver to drive the plunger and/or discharge the payload.

For the sake of this application, an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example, the driver may be designed to discharge the payload over a time period ranging between 20 and 120 seconds and/or between 120 and 600 seconds and/or between 600 seconds and an hour and/or between an hour and a day and/or longer.

In some embodiments, the apparatus may be preprogrammed to wait a fixed time delay ranging between 2 to 20 minutes and/or 20 minutes to an hour and/or an hour to 6 hours and/or 6 hours to 2 days after activation before beginning delivery of the substance. Optionally the length of the time delay may be an estimated time for a temperature sensitive component of the apparatus to reach a preferred working temperature. For example, the temperature sensitive component may include the drug and/or a battery.

In general, discharge may be driven by a driver. An internally powered driver may be powered by various mechanisms including for example a motor as discussed, including for example a DC motor, an actuator, a brushless motor, and/or a transmission including for example a telescoping assembly and/or a threaded element and/or a gear and/or a coupling and/or an elastic mechanism (for example a spring and/or a rubber band) and/or an expanding gas and/or a hydraulic actuator).

A drug delivery device in accordance with some embodiments of the present invention may include a reservoir part as discussed. For example, a reservoir may include a medicine container and/or a syringe. Optionally a syringe may be preloaded with medicine using standard equipment and/or in an aseptic room. A preloaded syringe may optionally include a proximal opening. A plunger may optionally seal the proximal opening and/or protect the sterility of the contents of the syringe. A sterile needle, typically hollow, may optionally be connected to the syringe barrel. For example, the hollow of the needle may be in fluid communication with the interior of the barrel.

The needle may optionally be rigidly attached to the extension at the distal end of the barrel. The sterility of all and/or part of the needle may for example be protected by a protective cap. The protective cap may remain on the needle when the syringe is supplied and/or installed into an injector. For example, the medicine container may optionally include a cylindrical barrel rigidly attached to a needle. In some embodiments, a plunger may slide axially along the inside of the barrel to discharge a medicine payload. For example, the medicine may be discharged through the hollow needle. The protruding tip of the needle may be oriented at an angle to the axis of the barrel.

An aspect ratio of the base may be defined as the ratio of the length of the longest axis of the base to the shortest axis. Optionally the axis ratio may range between 1 to 1.5 and/or 1.5 to 2 and/or between 2 to 3 and/or greater than 3. In some embodiments, the height of the injector may range between half the length of the short axis of the base to the length of the short axis of the base and/or between the length of the short axis of the base to twice the length of the short axis of the base and/or greater than the twice length of the short axis of the base. The height of the injector may supply leverage for pivoting the adhesive off the skin of a patient after use.

In some embodiments, the force to insert the needle to the skin of a patient may range for example between 0.02 to 0.2 N and/or between 0.2 and 0.5 N and/or between 0.5 to 5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, drug delivery device may include an auto-injector. The auto-injector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism (for example a needle retraction mechanism) may be sensitive to the force. For example the mechanism may include a snap that gives way at 70 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 2.5 and 15 mm. The torque to power injection may range for example between 0.2 and 1.0 N*cm. The trigger torque (the torque at which the needle safeguarding is triggered) may range for example between to 0.5 to 2 and/or from 2 to 7 and/or from 7 to 10N*cm.

During injection, the linear movement of a plunger may range for example between 10-50 mm. The length of movement of the plunger may vary for example with the volume of medicine to be injected that may range for example between 0.5 to 3 ml.

In some embodiments, a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments a time of discharge may range may depend on the fill volume and/or viscosity For example the expected injection speeds may be Injection speed depend on viscosity, for example for viscosity ranging from 1 cp to 15 cp the expected injection rage may range between 30 to 70 sec/1 ml, for example for viscosity ranging from 15 cp to 60 cp the expected injection rate may range between 35 to 60 sec/ml for viscosity above 60 cp the expected injection rate may range between 53 to 67 sec/1 ml. The maximum and/or minimum expected injection time may for example be the maximum and/or minimum allowed fill volume divided by an injection rate.

For example an expected time of discharge may range for example between 24 to 78 seconds (for example for between 0.8 and 1.2 ml of fluid having a viscosity ranging between 1 to 15 cp) and/or between 36 to 68 seconds (for example for between 1.2 and 1.7 ml of fluid having a viscosity ranging between 1 to 15 cp) and/or between 51 to 92 seconds (for example for between 1.7 and 2.3 ml of fluid having a viscosity between 1 to 15 cp) and/or between 70 to 150 seconds (for example for 2.0 to 2.5 ml of fluid having a viscosity of between 15 and 70 cp) and/or between 120 seconds and 3 minutes for larger volumes and/or viscosities. In some embodiments injection times may be longer. The length of the injection time may be determined by considerations other than viscosity and/or volume.

In some embodiments the reservoir may have a length ranging for example between 20 and 72 and/or 72 and 78 mm and/or 78 and 80 mm and/or 80 and 200 mm. In some embodiments an internal cylindrical space of a reservoir may have an average width ranging for example between 1 and 3 mm and/or 3 and 10 and/or 10 and 15 mm and/or 15 and 25 mm and/or 25 and 50 mm. Optionally a reservoir may have a circular cross section such that width is the diameter of the circle. In some embodiments an extension may have a straight end portion with a length ranging for example between 1 and 3 mm or 3 and 7 mm or 7 and 8 or 8 and 10 mm or 10 and 15 mm or 15 and 50 mm. In some embodiments the exposed straight portion of a needle may have a length ranging for example between 1 and 5 mm or 5 and 7 mm or 7 and 10 mm or 10 and 20 mm.

In some embodiments an extension may have a sealing ring for a needle cap. The sealing ring may have a length ranging for example between 0.1 and 0.6 mm or 0.6 and 1 mm or 1 and 2.5 mm or 2.5 and 3 mm or 3 and 6 mm or 6 and 15 mm. In some embodiments a sealing ring may have an internal cavity with a length ranging for example between 0.5 and 1.5 mm/or 1.5 and 2.5 mm or 2.5 and 5 mm or 5 and 10 mm.

In some embodiments the sealing ring may have an external average width which may also be an average outer diameter ranging for example between 1 and 7 mm or 7 and 5 mm or 5 and 10 mm or 10 and 20 mm. In some embodiments the sealing ring may have an internal average width which also may be an average inner diameter ranging for example between 1 and 3 mm or 3 and 7 mm or 7 and 10 mm or 10 and 18 mm. In some embodiments, the extension may have a neck (not including the sealing ring) with an average width which may be an average diameter ranging for example between 1 and 3 mm or 3 and 7 mm or 7 and 8 mm or 8 and 16 mm. Optionally the neck may have a non-uniform cross section (for example an I beam and/or cross shaped cross section) and/or a tapered cross section.

For a non-uniform cross section an average outer width may be defined as the width of the smallest oval that can enclose the neck averaged over the length of the neck. In some embodiments a fluid path between the extension and a reservoir cavity may include a 27 gauge needle or a needle ranging between 25 and 30 gauge or a needle ranging between 20 and 25 gauge or a needle ranging between 30 and 32 gauge. In some embodiments a needle protruding from an extension may include a 27 gauge needle or a needle ranging between 25 and 30 gauge or a needle ranging between 20 and 25 gauge or a needle ranging between 30 and 32 gauge.

It is expected that during the life of a patent maturing from this application many relevant technologies and/or materials will be developed and the scope of the terms are intended to include all such new technologies and materials a priori.

As used herein the terms "about", "approximately" and "substantially" refer to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 7, from 1 to 5, from 2 to 7, from 2 to 6, from 3 to 6 etc., as well as individual numbers within that range, for example, 1, 2, 3, 7, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A cartridge comprising:
    a barrel defining:
        a reservoir for receiving a substance therein;
        a proximal end that is open;
        a distal end that opposes the proximal end; and
        a longitudinal central axis extending from the distal end to the proximal end; and
    an arm projecting distally from the distal end of the barrel and having a portion that is bent at a fixed angle relative to the longitudinal central axis of the barrel, the arm being in fluid communication with the reservoir and defining a fluid path between the reservoir and the arm,
    wherein the arm comprises an injection needle in continuous fluid communication with the reservoir and defining a portion of the fluid path, the injection needle having a beveled terminal needle tip defining a distally facing opening, and
    wherein the arm projects from the distal end of the barrel at a location offset from the longitudinal central axis so as to define a space between the longitudinal central axis and the arm where the arm and the distal end of the barrel attach.

2. The cartridge of claim 1, wherein the arm is bent toward a bottom side of the barrel.

3. The cartridge of claim 2, wherein the arm includes a first portion projecting from the distal end of the barrel in a direction parallel with the longitudinal central axis, and the portion that is bent is a second portion defining an axis oriented at the fixed angle of between 30 to 150 degrees with respect to the longitudinal central axis.

4. The cartridge of claim 1, wherein the injection needle includes a portion that is bent and coincides with the portion that is bent of the arm at the fixed angle.

5. The cartridge of claim 1, wherein the arm and the barrel define a monolithic structure.

6. The cartridge of claim 1, wherein the longitudinal central axis defines a vertical central plane extending through the longitudinal central axis in a direction from a top side to a bottom side of the reservoir, and wherein the vertical central plane extends through a center of the arm.

7. The cartridge of claim 1, wherein the arm projects from the distal end of the barrel at a location positioned above the longitudinal central axis of the barrel.

8. The cartridge of claim 1, wherein the injection needle extends through an entirety of the arm.

9. The cartridge of claim 1, wherein a terminal end of the injection needle extends beyond a terminal end of the arm.

10. The cartridge of claim 1, wherein the reservoir is prefilled with the sub stance.

11. The cartridge of claim 1, wherein the reservoir is formed from a polymer.

12. The cartridge of claim 1, further comprising a needle cap configured to attach to the reservoir and to enclose the arm.

* * * * *